United States Patent
Chen et al.

(10) Patent No.: US 10,734,116 B2
(45) Date of Patent: Aug. 4, 2020

(54) REMOTE CLOUD BASED MEDICAL IMAGE SHARING AND RENDERING SEMI-AUTOMATED OR FULLY AUTOMATED NETWORK AND/OR WEB-BASED, 3D AND/OR 4D IMAGING OF ANATOMY FOR TRAINING, REHEARSING AND/OR CONDUCTING MEDICAL PROCEDURES, USING MULTIPLE STANDARD X-RAY AND/OR OTHER IMAGING PROJECTIONS, WITHOUT A NEED FOR SPECIAL HARDWARE AND/OR SYSTEMS AND/OR PRE-PROCESSING/ANALYSIS OF A CAPTURED IMAGE DATA

(71) Applicant: Quantant Technology Inc., Greenwood Village, CO (US)

(72) Inventors: Yuanming Chen, Greenwood Village, CO (US); Zhen Wang, Tianjin (CN); Sunhwa Jung, Centennial, CO (US)

(73) Assignee: QUANTANT TECHNOLOGY, INC., Greenwood Village, CO (US)

( * ) Notice: Subject to any disclaimer, the term of this patent is extended or adjusted under 35 U.S.C. 154(b) by 1315 days.

(21) Appl. No.: 14/823,821

(22) Filed: Aug. 11, 2015

(65) Prior Publication Data
US 2015/0347682 A1   Dec. 3, 2015

Related U.S. Application Data

(63) Continuation-in-part of application No. 13/633,811, filed on Oct. 2, 2012, now Pat. No. 9,105,200.
(Continued)

(51) Int. Cl.
*G06K 9/00* (2006.01)
*G16H 50/30* (2018.01)
(Continued)

(52) U.S. Cl.
CPC ............ *G16H 50/30* (2018.01); *G06T 15/08* (2013.01); *G09B 23/28* (2013.01); *G16H 30/40* (2018.01); *G16H 50/20* (2018.01); *G16H 80/00* (2018.01)

(58) Field of Classification Search
None
See application file for complete search history.

(56) References Cited

U.S. PATENT DOCUMENTS 5,584,701 A   12/1996  Lampotang et al.
5,791,907 A   8/1998   Ramshaw et al.
(Continued)

FOREIGN PATENT DOCUMENTS

WO   1999059106 A1   11/1999

OTHER PUBLICATIONS

International Search Report and Written Opinion of the International Searching Authority, Application No. PCT/US2016/041606 issued by the USPTO, Alexandria, Virginia, dated Sep. 28, 2016.
(Continued)

*Primary Examiner* — Atiba O Fitzpatrick
(74) *Attorney, Agent, or Firm* — Peter B. Scull; HDC IP Law LLP

(57) ABSTRACT

Systems, methods and software are provided that include a cloud, internet, and/or browser, application, or server based medical image sharing method and system that shares at least one 2D image data file through an internet browser that can generate rotatable and manipulatable 3D and/or 4D images by additional users without additional computer software, plug-ins, or hardware, to render 3D and 4D medical images for remote collaborative analysis, discussion, and/or diagnoses and that simulate or facilitate imaging of medical procedures for purposes of optimized performance, simulation, training and/or accreditation; as well as
(Continued)

generating 3D and/or 4D imaging from 2 or more 2D images and/or projections for such use as semi-automated and/or fully automated, network and/or web-based, 3D and/or 4D imaging.

9 Claims, 21 Drawing Sheets

Related U.S. Application Data

(60) Provisional application No. 62/191,233, filed on Jul. 10, 2015, provisional application No. 61/542,866, filed on Oct. 4, 2011.

(51) Int. Cl.
  *G06T 15/08* (2011.01)
  *G16H 50/20* (2018.01)
  *G09B 23/28* (2006.01)
  *G16H 80/00* (2018.01)
  *G16H 30/40* (2018.01)

(56) References Cited

U.S. PATENT DOCUMENTS

| | | | |
|---|---|---|---|
| 6,024,576 A | 2/2000 | Bevirt et al. |
| 6,047,080 A | 4/2000 | Chen et al. |
| 6,088,020 A | 7/2000 | Mor |
| 6,113,395 A | 9/2000 | Hon |
| 6,193,519 B1 | 2/2001 | Eggert et al. |
| 6,267,599 B1 | 7/2001 | Bailey |
| 6,375,471 B1 | 4/2002 | Wendlandt et al. |
| 6,470,302 B1 | 10/2002 | Cunningham et al. |
| 6,538,634 B1 | 3/2003 | Chui et al. |
| 6,628,977 B2 | 9/2003 | Graumann et al. |
| 6,654,000 B2 | 11/2003 | Rosenberg et al. |
| 6,912,265 B2 | 6/2005 | Hebecker et al. |
| 6,929,481 B1 | 8/2005 | Alexander et al. |
| 7,010,080 B2 | 3/2006 | Mitschke et al. |
| 7,120,283 B2 | 10/2006 | Thieret et al. |
| 7,129,946 B2 | 10/2006 | Ditt et al. |
| 7,234,937 B2 | 6/2007 | Sachdeva et al. |
| 7,249,951 B2 | 7/2007 | Bevirt et al. |
| 7,249,952 B2 | 7/2007 | Ranta et al. |
| 7,315,605 B2 | 1/2008 | Boese et al. |
| 7,327,872 B2 | 2/2008 | Vaillant et al. |
| 7,349,832 B2 | 3/2008 | Anderson |
| 7,404,716 B2 | 7/2008 | Gregorio et al. |
| 7,519,414 B2 | 4/2009 | Mitschke et al. |
| 7,599,730 B2 | 10/2009 | Hunter et al. |
| 7,653,229 B2 | 1/2010 | Kaufhold et al. |
| 7,689,019 B2 | 3/2010 | Boese et al. |
| 7,756,567 B2 | 7/2010 | Kuduvalli et al. |
| 7,761,136 B2 | 7/2010 | Ohishi et al. |
| 7,862,340 B2 | 1/2011 | Chen et al. |
| 7,991,105 B2 | 8/2011 | Mielekamp et al. |
| 8,004,524 B2 | 8/2011 | Deinzer |
| 8,311,791 B1* | 11/2012 | Avisar ................. G09B 23/28 |
| | | | 703/11 |
| 2002/0168618 A1 | 11/2002 | Anderson et al. |
| 2003/0015207 A1 | 1/2003 | Herold et al. |
| 2003/0068607 A1 | 4/2003 | Gregorio et al. |
| 2004/0009459 A1 | 1/2004 | Anderson et al. |
| 2004/0034550 A1 | 2/2004 | Menschik et al. |
| 2004/0076940 A1 | 4/2004 | Alexander et al. |
| 2004/0152970 A1 | 8/2004 | Hunter et al. |
| 2005/0214726 A1 | 9/2005 | Feygin et al. |
| 2006/0008786 A1 | 1/2006 | Feygin et al. |
| 2006/0184652 A1 | 8/2006 | Teodosiu et al. |
| 2006/0241413 A1 | 10/2006 | Boese et al. |
| 2007/0106750 A1 | 5/2007 | Moore |
| 2008/0243886 A1 | 10/2008 | Oosawa et al. |
| 2009/0018808 A1 | 1/2009 | Bronstein et al. |
| 2009/0177454 A1 | 7/2009 | Bronstein et al. |
| 2009/0219289 A1 | 9/2009 | Kalvin |
| 2010/0014740 A1 | 1/2010 | Movassaghi et al. |
| 2011/0085637 A1 | 4/2011 | Boese et al. |
| 2011/0243407 A1 | 10/2011 | Sofka |
| 2013/0085774 A1 | 4/2013 | Chen et al. |
| 2014/0277678 A1 | 9/2014 | Vesto |
| 2015/0172681 A1 | 6/2015 | Kim et al. |

OTHER PUBLICATIONS

Notification Concerning Transmittal of International Preliminary Report on Patentability for Application No. PCT/US2016/041606 issued by the International Bureau of WIPO, Geneva, Switzerland dated Jan. 25, 2018 which includes: the International Preliminary Report on Patentability dated Jan. 16, 2018 with the Written Opinion of the International Searching Authority, Application No. PCT/US2016/041606 issued by the USPTO, Alexandria, Virginia, dated Sep. 28, 2016.

* cited by examiner

REMOTE CLOUD BASED MEDICAL IMAGE SHARING AND RENDERING SEMI-AUTOMATED OR FULLY AUTOMATED NETWORK AND/OR WEB-BASED, 3D AND/OR 4D IMAGING OF ANATOMY FOR TRAINING, REHEARSING AND/OR CONDUCTING MEDICAL PROCEDURES, USING MULTIPLE STANDARD X-RAY AND/OR OTHER IMAGING PROJECTIONS, WITHOUT A NEED FOR SPECIAL HARDWARE AND/OR SYSTEMS AND/OR PRE-PROCESSING/ANALYSIS OF A CAPTURED IMAGE DATA

FIELD OF INVENTION

Aspects of the present invention relate generally to systems that store, share, render, simulate and/or facilitate imaging of medical procedures for purposes of optimized performance, simulation, training and/or accreditation. More particularly, aspects of the invention relate to a system, apparatus and/or subsystems for generating 3D and/or 4D imaging from 2 or more 2D images and/or projections for use in performing, simulating, training, and/or facilitating medical-access procedures.

BACKGROUND OF INVENTION

Medical practitioners, such as military medics, civilian emergency-medical personnel, nurses, and/or physicians, routinely perform medical and/or medical and/or vascular-access procedures (e.g., intravenous insertion, central venous line placement and/or peripherally-inserted central catheter, etc). It is desirable for a practitioner to be proficient at performing these procedures since a proficient practitioner is less likely to injure a patient and/or is almost certain to reduce a patient's level of discomfort.

Becoming proficient in medical and/or medical and/or vascular-access procedures requires practice. In fact, a certification and/or re-certification requirements of some states mandate a minimal number of needle sticks, etc., per year per provider. Historically, medical practitioners practiced needle-based procedures on live volunteers. More recently, simulation techniques and/or devices have been developed to provide training in medical and/or vascular-access procedures optionally without a use of live volunteers.

Some medical and/or vascular-access simulation systems that are in background publications include an interface device and/or a data processing system. To practice a medical and/or vascular-access procedure, a user manipulates an "instrument," which extends from a device and/or serves as a catheter-needle.

Potentiometers and/or encoders within an interface device track a motion and/or position of an instrument and/or relay this information to a data processing system. A data processing system performs a simulation of a structure and/or substructure of human anatomy, and/or determines an effect of an instrument's motion on a the anatomy. Simulated results are displayed by a data processing system. Using a motion information from an interface device, a data processing system also generates a control signal that controls a force-feedback system that is coupled to an instrument. A force-feedback system generates various resistive and/or reactive forces that are intended to simulate a forces that are experienced by a medical practitioner during an actual medical and/or vascular-access procedure. A user senses these forces during manipulation of an instrument.

Although some systems in background publications have an ability to simulate medical procedures like percutaneous coronary interventions (PCI), they are of limited value in assisting the medical professionals to prepare for their upcoming procedures since those systems don't have the capability to rapidly build a simulation based on the incoming patient's unique anatomy. Without the ability to build patient-specific simulations rapidly, those systems cannot provide decision support during mission-critical procedures like cardiac catheterization. As a result, physicians relies mostly on subjective pattern recognition and subjective quantification of key features to diagnose and treat patients.

The inability of prior medical and/or vascular-access simulation systems to realistically simulate a medical and/or vascular-access procedure for incoming patients limits their usefulness as training and/or accreditation tools.

There are currently many drawbacks of traditional medical image sharing approaches, including limitations on image where sharing is based on transferring original image files (e.g. DICOM files). For example, methods can include direct transfer of the image files, storage and/or archiving of the files on internal or external servers, that can be accessed by authorized users, but are limited to viewing the image files on a computer or mobile device. However, many medical images (e.g., CT scans) are saved as very large files that can be difficult or not possible for practical online transfer and/or storage, and/or which require the use of specialized servers, software, hardware, and/or connection of the imaging devices themselves. Additionally, various security and encryption systems also limit the availability or prevent access to such medical images.

Thus there are problems with accessibility and/or needed capabilities and associated costs for medical and other health professionals to have access to medical images which can be important for one or more of diagnosis, prognosis, treatment, or evaluation of patients.

Additionally, there is a need for online access by patients to healthcare professionals as an alternative to patients traveling to healthcare professionals, which can involve long and/or costly travel and lodging for patients to visit healthcare professionals that they can need to consult with for their medical and/or healthcare needs. Alternatively or additionally, patients can need to consult with several healthcare professionals simultaneously or in a coordinated manner, and online access would provide a solutions to these and other related or unrelated healthcare issues, which would include the transfer and review and/or analysis of medical images associated with one or more patients.

Furthermore, all medical personnel working at actual medical sites can recognize that when opinions are exchanged via documents, problems with communication can occur in the exchange of opinions based only on documents and also it take a long time to transfer opinions. Accordingly, a need arises to enable remote collaborative diagnoses to be easily made.

Accordingly, there is a need to provide solutions to the above problems that could allow easy, low cost, and/or more universal access to medical images for use by healthcare professionals and patients.

SUMMARY OF INVENTION

The present invention optionally relates to systems, apparatus, software, IT systems, and/or subsystems, for imaging and/or simulating medical-access procedures systems using semi-automated and/or fully automated, network and/or web-based 3D and/or 4D imaging of anatomy for training, rehearsing and/or conducting medical procedures, using multiple (e.g., >2 and/or >3) standard x-ray and/or other imaging projections without a need for special hardware and/or systems (e.g., rotational runs) and/or pre-processing/analysis of a captured image data.

The present invention optionally relates, in general, to remote collaborative medical or other image sharing and, more particularly, to a remote method and system using a cloud, internet, and/or browser, application, or server based medical image sharing scheme, which are capable of sharing and rendering (in 2D, 3D, or 4D) medical images for remote collaborative analysis, discussion, and/or diagnoses, without or optionally with the use of browser, application, or server based or computer based 2D, 3D, and 4D rendering. Disclosed are a cloud, internet, and/or browser, application, or server based medical image sharing method and system that shares at least one 2D image data file through an internet browser that can generate real time, user controlled, rotatable and manipulatable 3D and/or 4D images by additional users without additional computer software, plug-ins, or hardware, to render 3D and 4D medical images for remote collaborative analysis, discussion, and/or diagnoses.

Medical Image Sharing is a term for the electronic exchange of medical images between hospitals, physicians and patients. A typical architecture for a medical image sharing platform optionally includes transmitting data from a system installed directly on the hospital network and behind the firewall, to and from an outside entity. Some of the standard architectural pieces involved include:

Data transmission is the physical transfer of data through a communication channel, such as wires, wireless technologies or physical media. The most common use case for image sharing would be transmitting the image files using the cloud, allowing for instant access and exchange with anyone, anywhere. A Virtual private network (VPN) can be set up to enable exchange, but this is typically requires more to maintain for the facilities involved.

Data Compression is used to help facilitate the exchange of large files by encoding using smaller bits than the original version. This process helps reduce the resources being used and improves the transmission capabilities.

Security: One widely utilized security tool is TSL/SSL, or Transport Layer Security. The Transport Layer Security (TLS)/Secure Sockets Layer (SSLv3) is used to secure electronic communications. TLS/SSLv3 helps to secure transmitted data using encryption. TLS/SSLv3 authenticates clients to prove the identities of parties engaged in secure communication, as well as authenticates browser, application, or servers. The TLS/SSLv3 security protocol can protect against data disclosure, masquerade attacks, bucket brigade attacks, rollback attacks, and replay attacks.

Data Centers: A Data center is used to house computer systems and associated pieces. The main use of these facilities in medical image sharing is to provide backup. The infrastructure commonly optionally includes redundant power, redundant generators, redundant Internet connections, redundant firewalls, redundant network switches, and redundant storage. This is a vital piece to ensure that medical images are safe and secure in the cloud.

Accordingly, the present invention optionally provides deployment models (public vs. private), allowing users to optimize browser, application, or server configurations based on user requirements. The present invention provides one and/or more of a following: physicians and/or other medical practitioners performing one and/or more aspects of aspects of the invention can (i) assess a risks and/or difficulties of medical imaging for medical procedures for specific patient; (ii) to choose appropriate patients for a procedure and/or take actions to reduce a risks of complications and/or failure.

As a non-limiting example, aspects of the invention can be used for angiographic image analysis including 3D models to better plan and/or execute percutaneous coronary interventions (PCI) in a safe and/or effective manner. Physicians and/or hospitals can monitor their PCI services, benchmark their results against best practices in a country, and/or identify areas of improvement. Professional societies, government agencies, and/or medical device and/or pharmaceutical companies can monitor a size and/or characteristics of PCI care that is rapidly becoming a medical service costing billions of dollars and/or impacting millions of patients. A wealth of data gathered from aspects of the invention using an internet and/or other data storage, collection and/or use for such medical data and/or imaging can facilitate a use aspects of an invention for many uses, including but not limited to, training courses, clinical trials in devices and/or pharmaceuticals, other medical research, and/or a development of improved medical imaging and/or PCI products.

The present invention can provide and/or accomplish these benefits in different aspects, e.g., but not limited to, patient-specific decision-support system including an 3D and/or 4D image analysis service delivered at a point of care and/or structured to enhance a physician's judgment and/or experience and/or improve patient outcomes. An aspect of the present invention also provides data banks, data systems, and/or data analysis, e.g., data banks combining medical imaging data elements with comprehensive clinical data into a next generation registry. An aspect of the present invention further can provide sophisticated but user-friendly internet, server, and/or cloud-based IT platforms (e.g. cloud computing and/or database infrastructure) for collection of data, advanced image analysis, distribution of results, and/or professional development of physicians.

The present invention can provide and/or establish services that can be distributed locally, regionally, country by country, and/or internationally to improve, standardize, and/or optimize clinical practices, improve patient outcome, enhance healthcare quality and/or safety, and/or maximize a benefits of medical procedures and/or related medical imaging to patients. A present invention's systems, methods, software, IT and/or other embodiment services can be constructed to be sensitive to a culture, people, and/or health care system of a specific country.

An illustrative embodiment of aspects of the invention is a simulation system that provides patient-specific decision support and realistic training and/or practice for performing medical and/or vascular-access procedures without using human subjects Unlike most prior-art simulation systems, some embodiments of a present system provide a realistic, three-dimensional simulation derived directly from the patient's medical images (e.g. patient's 2D angiographic images). Since the patient-specific model accurately describes the real patient anatomy (e.g., human heart, vasculature, etc.), the simulation helps medical professionals to rehearse a medical procedure as if the simulated procedure were an actual procedure.

Background publications, such as U.S. patent application Ser. No. 12/224,314, filed by Ran Bronstein et al from Simbionix Ltd, Jan. 13, 2008 (entirely incorporated herein by reference), describes a preoperative surgical simulation method that receives 3D patient images for generating 3D anatomy model of the patient. The 3D medical image in this method is claimed to be a member of the following group: computerized tomography (CT) scan images, magnetic resonance imager (MRI) scan images, ultrasound scan images, and positron emission tomography (PET)-CT scan images. The medical simulation system in our present invention can process not only 3D patient images, but also 2D angiographic images. The value of building 3D patient models from 2D images is significant since common procedures like PCI are predominantly performed with 2D image guidance (e.g. X-ray), not with 3D imaging guidance (e.g. CT, MRI). For example, coronary angiography with X-ray image guidance remains the gold standard in the diagnosis and treatment of coronary artery disease, and over 2 million PCI procedures with 2D image guidance are performed in the US each year. All known background publications don't address the challenge of building 3D simulations with 2D patient images for the purpose of providing patient-specific support.

Other known background publications related to building medical simulation systems, such as U.S. Pat. No. 7,862,340 issued on Jan. 4, 2011, U.S. Pat. No. 7,308,831 issued on Dec. 18, 2007 and U.S. patent Ser. No. 10/538,005 issued on Aug. 9, 2011 (all and each of the above entirely incorporated herein by reference), are based on predefined patient models. Some of those pre-defined models are constructed using 3D modeling software, i.e. from scratch using anatomy books, video clips, etc. as references only. Other pre-defined models are reconstructed from real patient data, a process that often takes days or months to complete, and a collection of pre-defined patient models are stored in databases before the simulation system becomes operational. During the operation mode, the system simulates an image-guided procedure according to a virtual model selected by the user.

One or more aspects of the present invention address this challenge, e.g., by incorporating real patient data in the procedure room to assist clinical professionals to achieve better patient outcomes. An illustrative embodiment of a medical and/or vascular-access simulator includes a data-processing system and/or an interface device, a latter referred to herein as a "haptics device". A unique aspect of the invention is that data-processing system is web-enabled, allowing medical professionals at different geological locations to upload patient-specific data (e.g. DICOM images) to a cloud server and receive patient-specific decision support at any time. A network of web-enabled simulation systems located across a country can provide a cost-effective platform for professional societies, government agencies, and medical device and pharmaceutical companies to standardize clinical practices, and to optimize procedure successes.

An illustrative embodiment of aspects of the cloud server of the invention comprises of a collection of services to support the simulator network, including, but not limited to, Anatomy Reconstruction Cloud Service, Procedure Simulation Cloud Service and Patient Record Cloud Service (FIG. 1).

An illustrative embodiment of aspects of the invention comprises: providing a three-dimensional model of at least a portion of an anatomy, wherein a three-dimensional model describes at least a portion of a blood vessel; providing a three-dimensional model of a medical instrument; and/or generating a force-feedback profile based on an interaction of a model of anatomy and/or a model of a medical instrument. Some configurations of aspects of the invention therefore provide a method for reconstructing a volumetric image of an object. A method includes obtaining a 2D image dataset of an object corresponding to a relevant anatomical region for imaging for medical procedures, wherein a 2D image dataset can includes a plurality of projection radiographs of an imaged object obtained at similar and/or different angles.

A method also optionally includes utilizing a 2D image dataset and/or additional information about an object to minimize a selected energy function and/or functions to jointly satisfy and/or arbitrate among a selected set of constraints. A 3D volumetric image representative of an imaged object is thereby obtained through a use of image analysis that can include one and/or more algorithms selected from one and/or more of projection, composition and/or extraction algorithms that convert 2 and/or more and/or 3 and/or more 2D images to 3D and/or 4D images.

Also, some configurations of aspects of the invention provide a method for reconstructing a volumetric image of an object, in which a projection dataset of an object is acquired and/or a projection radiographs are preprocessed to produce quantitative projections that can include one and/or more algorithms selected from one and/or more of projection, composition and/or extraction algorithms that convert 2 and/or more and/or 3 and/or more 2D images to 3D and/or 4D images. In a quantitative projections, a pixel intensities in each quantitative projection correspond to an amount of material each x-ray passed through in its path from an x-ray source to a detector pixel. A method further includes performing an initial reconstruction, and/or choosing an energy definition to minimize, wherein an energy definition includes a term that constrains a reconstructed volumetric image to an N-ary and/or approximately N-ary composition of material classes (where N-ary indicates that each voxel is one of N material classes).

In yet other aspects, aspects of the invention provides a method for reconstructing a volumetric image of a part of anatomy relevant for treatment and/or surgery through a use of image analysis that can include one and/or more algorithms selected from one and/or more of projection, composition and/or extraction algorithms that convert 2 and/or more and/or 3 and/or more 2D images to 3D and/or 4D images. A method includes acquiring a 2D image dataset that includes a set of projection radiographs from a same and/or different projection angles. A geometry of a three-dimensional volume that contains part of anatomy relevant for treatment and/or surgery is estimated to produce an air/tissue volumetric image of an imaged part of anatomy relevant for treatment and/or surgery, and/or thereby a volumetric image of a part of anatomy relevant for treatment and/or surgery. Radiation path lengths through part of anatomy relevant for treatment and/or surgery are determined for each projection radiograph in a 2D image dataset. A method further includes using a determined radiation path lengths and/or 2D image dataset to estimate a percentage and/or amount of equivalent part of anatomy relevant for treatment and/or surgery for each projection radiograph, so that a estimate thereby produces a set of quantitative projections, that can include one and/or more algorithms selected from one and/or more of projection, composition and/or extraction algorithms that convert 2 and/or more and/or 3 and/or more 2D images to 3D and/or 4D images. In addition, a method includes determining an overall percentage equivalent tissue for a plurality of x-ray projection radiographs using a quantitative projections, and/or using a set of quantitative projections to estimate volumetric intensities in a part of anatomy relevant for treatment and/or surgery. An estimated volumetric image intensities are utilized to determine an N-ary and/or almost N-ary volumetric image of a part of anatomy relevant for treatment and/or surgery, wherein at least most voxels of a volumetric image are labeled as one of a member of a set of tissues including any tissue or vessel and/or equivalent tissue.

In yet another aspect, aspects of the invention provides an apparatus for producing a reconstructed volumetric image of an object. An apparatus includes a radiation source, a detector, an image processor and/or a computer. An image processor is not necessarily a separate component from a computer. An apparatus is configured to obtain a 2D image dataset of an object. An apparatus is further configured to utilize a 2D image dataset and/or additional information about an object to minimize a selected energy function and/or functions to jointly satisfy and/or arbitrate among a selected set of constraints. In so doing, a volumetric image is obtained in which each voxel is assigned a specific component material class, through a use of image analysis that can include one and/or more algorithms selected from one and/or more of projection, composition and/or extraction algorithms that convert 2 and/or more and/or 3 and/or more 2D images to 3D and/or 4D images.

In yet another configuration, aspects of the invention provides an apparatus for producing a volumetric image of an object. An apparatus includes a radiation source, a detector, an image processor and/or a computer. An image processor is not necessarily a separate component from a computer. An apparatus is configured to acquire a 2D image dataset of an object and/or preprocess a 2D image dataset to produce quantitative projections. An apparatus is further configured to perform a 3D and/or 4D image reconstruction. An initial reconstructed volumetric image may be used to choose an energy definition to minimize, wherein an energy definition includes a term that constrains a reconstructed volume to an N-ary and/or approximately N-ary composition.

In yet other aspects, aspects of the invention provides an apparatus for producing a reconstructed volumetric image of a part of anatomy relevant for treatment and/or surgery. An apparatus includes a radiation source, a detector, an image processor and/or a computer, although an image processor is not necessarily a separate component from a computer. A apparatus is configured to acquire a 2D image dataset including a set of projection radiographs of a part of anatomy relevant for treatment and/or surgery from a same and/or different projection angle s, and/or estimate a geometry of a three-dimensional volume that contains part of anatomy relevant for treatment and/or surgery to produce an air/tissue volumetric image of an imaged part of anatomy relevant for treatment and/or surgery, and/or thereby a volumetric image of a part of anatomy relevant for treatment and/or surgery. Radiation path lengths through a part of anatomy relevant for treatment and/or surgery are determined for each projection radiograph in a 2D image dataset, and/or determined radiation path lengths and/or a 2D image dataset are used to estimate a percentage and/or amount of equivalent part of anatomy relevant for treatment and/or surgery composition for each projection radiograph. An apparatus thereby produces a set of quantitative projection estimates. An apparatus is further configured to determine an overall percentage tissue for a plurality of x-ray projection radiographs using a quantitative projections and/or to use a set of quantitative projections to estimate volumetric image intensities in a part of anatomy relevant for treatment and/or surgery. An apparatus is also configured to utilize a estimated volumetric image intensities to determine an N-ary and/or almost N-ary reconstruction of a volumetric image of a part of anatomy relevant for treatment and/or surgery. At least most voxels of a volumetric image are labeled as one and/or another member of a set of tissues including any tissue or vessel and/or tissue.

It will be appreciated that configurations of aspects of the invention are able to generate volumetric images that provide three-dimensional localized quantitative tissue characteristics and/or classification in addition to qualitative information about three-dimensional location, shape, and/or extent of structures provided by various known types of medical imaging, e.g., but not limited to, x-rays, CAT scans, PET scans, MRI, and/or other known methods, e.g., but not limited to, tomosynthesis.

Quantitative information incorporated into three-dimensional volumetric images in various configurations of aspects of the invention adds significant diagnostic value to a reconstructed volume while also providing collateral constraints to aid in management of reconstruction artifacts. Furthermore, in some medical applications, a reconstructed three-dimensional volumetric image of an imaged part of anatomy relevant for treatment and/or surgery and/or other structure can be expressed in terms of its constituent tissue types. As a result, reconstructed volumetric images are completely independent of an X-ray technique used to acquire a corresponding 2D image dataset. X-ray technique-independent volumes can be used for making comparisons between volumes reconstructed from datasets acquired on different dates, for example.

Some of configurations of aspects of the invention are not limited to part of anatomy relevant for treatment and/or surgery image reconstruction and/or to medical applications in general, but rather can be used for quantitative reconstruction of an image of any object having a plurality of constituent material classes.

The present invention also has been made to solve one or more of the above or other problems in this area and an object of the present invention is to provide a remote and/or web-based collaborative image review, rendering, and/or diagnosis method and system using a cloud, internet, and/or browser, application, or server based medical image sharing scheme, which is capable of sharing medical images, thereby facilitating remote collaborative diagnoses.

The invention optionally provides a browser based 2D image sharing and 3D or 4D rendering and display method, comprising:

transferring, on a computer data network browser, application, or server and through a peer to peer (PTP) or public cloud network or transfer protocol or file attachment, at least one first 2D medical image computer data file to at least one data storage device provided as part of at least one first mobile device or personal computer of at least one first user;

accessing by the at least one first user the at least one first 2D image computer data file in a browser on the first mobile device or personal computer; and rendering on at least one first visual display connected to or included in the at least one first mobile device or personal computer, as controlled in real time by the first user accessing through the browser, at least one real time and manipulatable 3D or 4D image generated from the at least one first 2D image, which at least 3D or 4D image can be shared and viewed on at least one second visual display via at least one second browser by at least one second user accessing the 2D, 3D, or 4D image on the second browser displayed on at least one second users' at least one second mobile device or personal computer.

Methodology of acquiring 2D images can optionally include using X-rays and/or other imaging projections (e.g., but not limited to, CT, MRI, Ultrasound, and the like) to generate 3D/4D imaging. The optional alternative approaches of acquiring those 2D images can include one or more of the following: acquiring medical imaging data stored in a picture archiving and communication system (PACS). A common format of medical imaging data is DICOM, a standard for handling, storing, printing, and transmitting information in medical imaging. This format is widely used to store different types of images; acquiring medical imaging data retrieved through laser scanning or other surface scanning methods (e.g., but not limited to, LED, blue light, and the like). Surface scanning is a very common approach in dental industry where hand-held scanner retrieves 2D images. Those 2D scanner data can be reconstructed into 3D models using methods as described herein or as known in the art;

acquiring medical imaging data encoded in a standard 2D format (e.g., but not limited to, JPEG, PNG, BMP, TIFF, RAW, and the like), which can be generated or provided using known methods and/or devices, e.g., but not limited to cameras, and devices comprising cameras, such as digital or film cameras, computers, mobile devices such as smart phones or tablets, can be used to capture 2D medical images;

acquiring medical imaging data encoded in a standard video format (e.g. mp4, AVI, H264, VP8, VP9, WMV, and the like), where videos are a series of 2D images, and thus can used to provide such 2D or 3D images and reconstructed into 3D or 4D models using 3D reconstruction methods as described herein, and which can be generated or provided using known methods and/or devices, e.g., but not limited to cameras, and devices comprising cameras, such as digital or film cameras, computers, mobile devices such as smart phones or tablets.

acquiring medical imaging data of the aforementioned types (DICOM, scanner, standard images and videos) that are stored on external devices, including but not limited to, flash drive, DVD, hard disk, or cloud storages like Dropbox and OneDrive.

Methodology of transmitting 2D/3D/4D imaging can optionally include one or more of transmitting 2D/3D/4D medical imaging using network and/or web-based approach so that training, rehearsing and/or conducting medical procedures can be performed without need for one or more of special hardware and/or systems and/or pre-processing/analysis of a captured image data. The detailed approaches of transmitting those 2D/3D/4D medical imaging are optionally as disclosed herein, such as but not limited to: where the 2D/3D/4D imaging can be viewed by users BEFORE the transmission starts without the need for special hardware and/or systems;

the sender may not need to view images before the transmission starts; or the sender can do one or more of collecting medical imaging data and sending those files through a network and/or web to a receiving party, where the receiving party does now not require according to the invention having any special or additional software, hardware or other tools to decode and visualize those files, but can do so according to the invention by using a browser or similar interface provided on a computer; and in medical training/rehearing scenarios, the present invention optionally provided wherein the sender can view medical imaging data BEFORE the transmission starts since the sender is the most likely party to PRODUCE the 2D/3D/4D medical training/rehearsing contents using reconstruction techniques outlined in the original patent;

In order to allow users to view 2D/3D/4D medical image data BEFORE the transmission starts, a JavaScript library such as, but not limited to, quantantShare.JS can be used to decode medical image data in various formats, including but not limited to DICOM, scanner, standard image and video formats, as known in the art. Since this library is developed in JavaScript, a programming language that is supported on all web browsers, optionally according to the invention, a sender of medical image contents can view 2D/3D/4D medical image data on any internet-enabled devices or computers without the need to install any extra plug-in.

The 2D/3D/4D imaging can thus optionally be modified by users according to the invention BEFORE the transmission starts without the need for special hardware and/or systems.

For example, in medical training/rehearing scenarios, it is also optionally provided according to the invention that the sender can modify medical imaging data BEFORE the transmission starts since the sender is the most likely party to PRODUCE the 2D/3D/4D medical training/rehearsing contents using reconstruction techniques outlined in the original patent. Non limiting examples of the modifications that quantantShare.JS library or similar system can support include one or more of:

Removing the protected or private patient information from the original medical image data (e.g. DICOM, scanner, standard image and video formats) BEFORE the transmission starts in order to optionally produce training/rehearing contents that are compliant to HIPPA laws;

Removing 2D/3D/4D datasets from the original medical image data (e.g. DICOM, scanner, standard image and video formats) that are optionally considered not relevant to the training/rehearing contents BEFORE the transmission starts in order to improve transmission efficiency;

Adding annotations to 2D/3D/4D medical imaging data BEFORE the transmission starts.

Adjusting visual effects of 2D/3D/4D medical imaging data BEFORE the transmission starts. For example, the sender can adjust window/level parameters when opening DICOM files in a browser BEFORE the transmission starts;

Creating 3D/4D simulation models based on original medical image data (e.g. DICOM, scanner, standard image and video formats) BEFORE the transmission starts using the 3D reconstruction capability described in the original patent.

For example, the inventions allow the sender to modify the sizes or even relative positions of 3D objects for creating training scenarios like "aligning a medical device against a body part", or "deciding implant dimensions and orientations". The quantantShare.JS library has built-in support for image measurement and object manipulation to make it easy to create realistic simulation scenarios.

The invention optionally provides wherein the at least one first 2D medical image computer data file is stored and rendered on said into said 3D or 4D real time and manipulatable image display using the first or second browser without further processing by additional software or browser plugin on the first or second users' first or second mobile device or personal computer.

The invention optionally provides wherein the at least one first 2D medical image computer data file comprises, is decoded from, or is generated from, a DICOM-format medical image file.

The invention optionally provides wherein the at least one first 2D medical image computer data file is stored on non-transitory memory of a device, computer, PACS, browser, application, or server, or cloud storage location prior to said transferring step.

The invention optionally provides wherein the decoded DICOM-format medical image file format does not preserve the original resolution of the DICOM data and optionally includes partial DICOM data or annotation data and wherein the decoded DICOM-format medical image file is less than 50, 40, 30, 20, 10, or 5% of the file size of the original un-decoded DICOM-format medical image file.

The invention optionally provides wherein the first or second user is logged as a registered user of the computer data network browser, application, or server.

The invention optionally provides wherein the DICOM-format medical image file is preprocessed in a JavaScript™-based library as locally-opened DICOM data prior to said transferring step, wherein protected or private patient information is removed from the DICOM-format medical image file.

The invention optionally provides wherein the protected or private patient information is PHI BEFORE data in the DICOM-format medical image file, to protect confidential or private patient information, and wherein the patient information removal is completed without any extra private data removal processing software.

The invention optionally provides wherein the mobile device comprises preinstalled JavaScript™-based library software in non-transitory computer readable media that enables said visual display to render said 3D or 4D image data from multiple 2D medical image computer data files simultaneously.

The invention optionally provides wherein the 2D medical image computer data file are 2D x-ray image files and said rendering generates 3D and 4D x-ray images that are rotatable on said at least one first or second visual displays.

The invention optionally provides wherein said at least one first or second visual display further displays at least one of the at least one first or second mobile device or personal computer's device: entry point, entry direction, type, 3D mesh, image anatomy 3D mesh, physics attributes, rendered image analytic data, or rendering related data.

The invention optionally provides wherein the rendered 3D or 4D image data file formats include at least one selected from OBJ formats, 3D printer formats, CAD software file formats, Point Cloud formats, and any other 3D/4D imaging format.

The invention optionally provides wherein the 3D or 4D image displays of the at least one first and second users are synchronized.

The invention optionally further comprises providing at least one of an annotation, text, and voice information between the first and second users that is transmitted to the other user's visual display in real time as inputted by the first or second user via the first or second browser.

The invention optionally provides wherein the transferring of the at least one 2D medical image computer data file further optionally includes searching for a plurality of second users with whom the 2D, 3D, or 4D medical image will be shared, based on user information data previously stored via the first browser by the first user.

The invention optionally further comprises one or more of the following or any portion thereof:
(a) manipulating 3D bone models & 3D implant models to determine ideal procedure plans or to perform simulations for training purposes either without the server or with the server;
(b) blending CT images and 3D surface scanning data to determine ideal procedure plans or to perform simulations for training purposes either without the server or with the server;
(c) blending CT images and 2D photos from a patient to determine ideal procedure plans or to perform simulations for training purposes either without the server or with the server;
(d) tracking bone movement trajectories based on CT/MRI/X-Ray images either without the server or with the server;
(e) acquiring 2D videos to reconstruct 3D tooth models: the reconstruction could be accomplished either without the server or with the server;
(f) aggregating images from multiple imaging modalities (e.g. 2D X-ray, 3D surface scanning data, 3D CT, 4D simulations, etc.) into a single view inside a browser 2D stitching & deformation of facial images with or without the server;
(g) measuring, annotating, pixel manipulating or simulation of 2D/3D/4D images with or without the server;
(h) comparing and/or image blending of pre and post procedural 2D/3D/4D images with or without the server;
(j) editing and simulation against 2D/3D/4D images with or without the server.

The invention optionally provides non-transitory computer-readable medium containing executable program instructions executed by a processor that stores a program for executing a cloud, internet, and/or browser, application, or server based medical image sharing method, comprising:
program instructions that transfer, on a computer data network browser, application, or server and through a peer to peer (PTP) or public cloud network or transfer protocol or file attachment, at least one first 2D medical image computer data file to at least one data storage device provided as part of at least one first mobile device or personal computer of at least one first user;
program instructions that provide access by the at least one first user the at least one first 2D image computer data file in a browser on the first mobile device or personal computer; and
program instructions that provide rendering on at least one first visual display connected to or included in the at least one first mobile device or personal computer, as controlled in real time by the first user accessing through the browser, at least one real time and manipulatable 3D or 4D image generated from the at least one first 2D image, which at least 3D or 4D image can be shared and viewed on at least one second visual display via at least one second browser by at least one second user accessing the 2D, 3D, or 4D image on the second browser displayed on at least one second users' at least one second mobile device or personal computer.

The invention optionally provides a cloud, internet, and/or browser, application, or server based medical image sharing system, comprising a processor configured to:
transfer, on a computer data network browser, application, or server and through a peer to peer (PTP) or public cloud network or transfer protocol or file attachment, at least one first 2D medical image computer data file to at least one data storage device provided as part of at least one first mobile device or personal computer of at least one first user;

access by the at least one first user the at least one first 2D image computer data file in a browser on the first mobile device or personal computer; and render on at least one first visual display connected to or included in the at least one first mobile device or personal computer, as controlled in real time by the first user accessing through the browser, at least one real time and manipulatable 3D or 4D image generated from the at least one first 2D image, which at least 3D or 4D image can be shared and viewed on at least one second visual display via at least one second browser by at least one second user accessing the 2D, 3D, or 4D image on the second browser displayed on at least one second users' at least one second mobile device or personal computer.

Still another optionally object of the present invention is to provide a web or cloud bases user interface that enables a plurality of users participating in a collaborative diagnosis in a remote environment to conveniently share the visual display rendering of medical and other images, such as expansion, 2D, 3D or 4D rendering, of a medical image displayed to the users in common, annotation, the selection of a medical image of interest from a set of various medical images, switching between a plurality of medical images displayed at the same time, 3-dimensional (3D) or 4-dimensional (4D) rendering, the results of additional processing, such as a computer aided diagnosis (CAD), and/or the like, which has unexpectedly been discovered to be possible using at least online computation and/or vector based rendering of such images of a mobile device or computer, with or without the use of additional computational hardware and/or software, such that, as a non-limiting example, any user can access and render images using PTP or other types of direct online communication that optionally provides rendering computation and display using only the mobile device or personal computer of the user, such as the browser and operating software of the mobile device or personal computer.

Still another object of the present invention is to provide a remote collaborative diagnosis method and system using a cloud, internet, and/or browser, application, or server based medical image sharing scheme, which are capable of reducing or eliminating data traffic between users and improving the security of medical images.

More specifically, an optional object of the invention is to provide a remote collaborative image display, analysis, diagnosis, and/or sharing method and system using a cloud, internet, and/or browser, application, or server based medical image sharing scheme, which optionally provides for 3D and/or 4D rendering of the image from one, two, or three or more 2D images using only the browsers or operating hardware and/or software of the user's mobile device or personal computer, optionally without the need for additional browser, application, or server, computer, and/or software calculation, rendering, and/or visual display computation and/or algorithms.

In accordance with an aspect of the present invention, there is provided a browser based 2D image sharing and 3D or 4D rendering and display system and/or method, comprising one or more of:

providing, by a processor, at least one first 2D medical image requested by a first user on a mobile device or personal computer;

receiving, through a peer to peer (PTP), VPN, or publicly available network, browser based, transfer of the at least one first 2D image data file; and rendering on a visual display connected to the mobile device or personal computer, as controlled in real time by the first user accessing through the browser, the at least one real time 3D or 4D image generated from the at least one first 2D image, which at least 3D or 4D image can be shared and viewed by at least one second user accessing the 2D, 3D, or 4D image on the at least one second users' mobile device or personal computer.

The cloud, internet, and/or browser, application, or server based medical image sharing method can further include receiving information about sharing (medical image sharing), wherein the information about sharing can be set by the first user, which belongs to information related to the first medical image; providing the first medical image can include providing the first medical image and the set information about sharing to the second user.

The cloud, internet, and/or browser, application, or server based medical image sharing method can further include, if at least one of an annotation, text, and voice information is received from any one of the first and second users, providing the received information to the other user so that the received information can be shared with the other user.

Providing the first medical image can include searching for information about a user group requested by the first user from information about one or more user groups, and providing the retrieved information about the user group to the first user; and receiving the information about the second user can include receiving information about the second user selected by the first user from among a plurality of users included in the retrieved information about the user group.

Providing the first medical image can include searching for a plurality of users with whom the first medical image will be shared based on user information previously stored by the first user, and providing the plurality of retrieved users to the first user along with the first medical image; and receiving the information about the second user can include receiving information about the second user selected by the first user from among the plurality of users.

Providing the first medical image can include providing information about a link to the first medical image to the second user, and providing the first medical image to the second user.

In accordance with another aspect of the present invention, there is provided a cloud, internet, and/or browser, application, or server based medical image sharing system, including a sending unit configured to provide a first medical image requested by a first user of a first user to the first user; a reception unit configured to receive information about a second user with whom the first medical image will be shared by the first user; a sharing control unit configured to control the sending unit to provide the first medical image to a second user of the second user based on the information about the second user; and an image processing unit configured to, when a user input related to an operation of the first medical image is received from any one of the first and second users, process the first medical image based on the received user input, and generate a second medical image related to the first medical image; wherein the sharing control unit controls the sending unit to provide the generated second medical image to the first and second users.

DESCRIPTION

Figure 1:
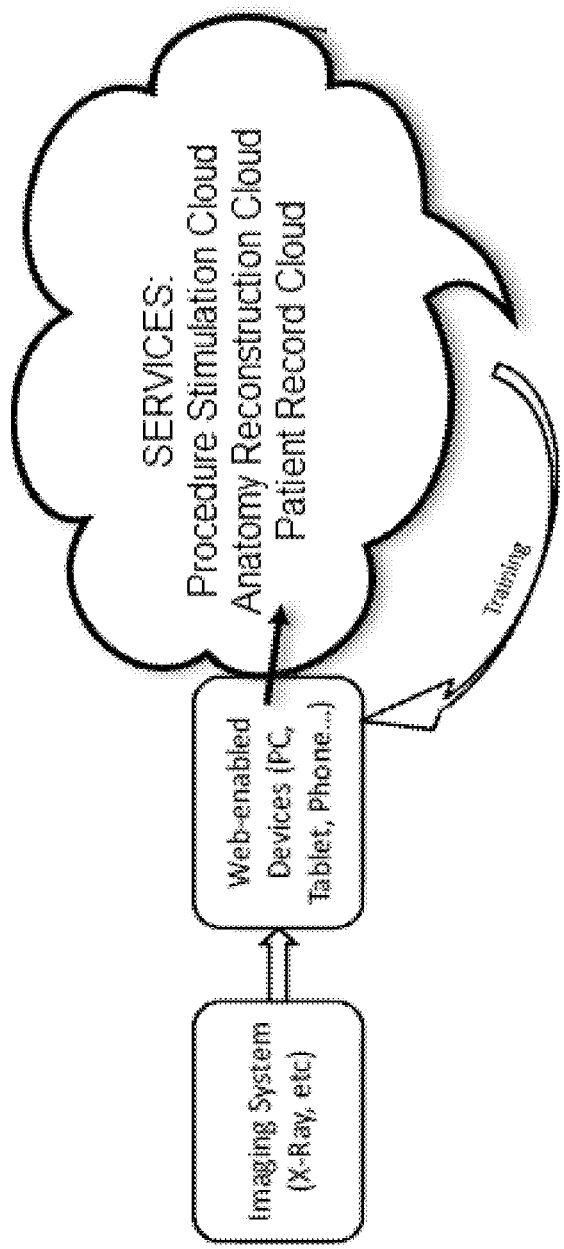
FIG. 1 is a flow diagram representing a non-limiting example of a projection algorithm that can be used in an invention that uses ray tracing method to construct one 3D grid for each angiogram (in other words, each 2D image is projected to a 3D volume). Each projection takes into account an original anatomical image as well as a detector (e.g., a C-ARM) location information. A ray tracing method can make corrections to a projection results when annotation data is present.

Hereinafter, embodiments of the present invention will be described in detail with reference to the accompanying drawings. Reference now should be made to the elements of drawings, in which the same reference numerals are used throughout the different drawings to designate the same elements. In the following description, detailed descriptions of known elements or functions that can unnecessarily make the gist of the present invention obscure will be omitted.

The present invention relates to systems, apparatus, software, IT systems, and/or subsystems, for imaging and/or simulating medical-access procedures systems using semi-automated and/or fully automated, network and/or web-based 3D and/or 4D imaging of anatomy for training, rehearsing and/or conducting medical procedures, using multiple (e.g., >2 and/or >3) standard x-ray and/or other imaging projections without a need for special hardware and/or systems (e.g., rotational runs) and/or pre-processing/analysis of a captured image data.

The present invention provides one and/or more of a following: physicians and/or other medical practitioners performing one and/or more aspects of aspects of the invention can (i) a assess a risks and/or difficulties of medical imaging for medical procedures for specific patient (ii) to choose appropriate patients for a procedure and/or take actions to reduce a risks of complications and/or failure.

As a non-limiting example, aspects of the invention can be used for angiographic image analysis including 3D models to better plan and/or execute percutaneous coronary interventions (PCI) in a safe and/or effective manner. Physicians and/or hospitals can monitor their PCI services, benchmark their results against best practices in a country, and/or identify areas of improvement. Professional societies, government agencies, and/or medical device and/or pharmaceutical companies can monitor a size and/or characteristics of PCI care that is rapidly becoming a medical service costing billions of dollars and/or impacting millions of patients. A wealth of data gathered from aspects of the invention using an internet and/or other data storage, collection and/or use for such medical data and/or imaging can facilitate a use aspects of an invention for many uses, including but not limited to, training courses, clinical trials in devices and/or pharmaceuticals, other medical research, and/or a development of improved medical imaging and/or PCI products.

The present invention can provide and/or accomplish these benefits in different aspects, e.g., but not limited to, patient-specific decision-support system including an 3D and/or 4D image analysis service delivered at a point of care and/or structured to enhance a physician's judgment and/or experience and/or improve patient outcomes. An aspect of the present invention also provides data banks, data systems, and/or data analysis, e.g., data banks combining medical imaging data elements with comprehensive clinical data into a next generation registry. An aspect of the present invention further can provide sophisticated but user-friendly internet, server, and/or cloud-based IT platforms (e.g., cloud computing and/or database infrastructure) for collection of data, advanced image analysis, distribution of results, and/r professional development of physicians.

The present invention can provide and/or establish services that can be distributed locally, regionally, country by country, and/or internationally to improve, standardize, and/or optimize clinical practices, improve patient outcome, enhance healthcare quality and/or safety, and/or maximize a benefits of medical imaging, including, but not limited to, PCI and/or related medical imaging to patients. A present invention's systems, methods, software, IT and/or other embodiment services can be constructed to be sensitive to a culture, people, and/or health care system of a specific country.

An illustrative embodiment of aspects of the invention is a simulation system that provides patient-specific decision support and realistic training and/or practice for performing medical and/or vascular-access procedures without using human subjects Unlike most prior-art simulation systems, some embodiments of a present system provide a realistic, three-dimensional simulation derived directly from the patient's medical images (e.g. patient's 2D angiographic images).

The invention optionally provides a browser based 2D image sharing and 3D or 4D rendering and display method, comprising:

transferring, on a computer data network browser, application, or server and through a peer to peer (PTP) or public cloud network or transfer protocol or file attachment, at least one first 2D medical image computer data file to at least one data storage device provided as part of at least one first mobile device or personal computer of at least one first user;

accessing by the at least one first user the at least one first 2D image computer data file in a browser on the first mobile device or personal computer; and rendering on at least one first visual display connected to or included in the at least one first mobile device or personal computer, as controlled in real time by the first user accessing through the browser, at least one real time and manipulatable 3D or 4D image generated from the at least one first 2D image, which at least 3D or 4D image can be shared and viewed on at least one second visual display via at least one second browser by at least one second user accessing the 2D, 3D, or 4D image on the second browser displayed on at least one second users' at least one second mobile device or personal computer.

The invention optionally further comprises one or more of the following or any portion thereof:

(a) manipulating 3D bone models & 3D implant models to determine ideal procedure plans or to perform simulations for training purposes either without the server or with the server;

(b) blending CT images and 3D surface scanning data to determine ideal procedure plans or to perform simulations for training purposes either without the server or with the server;

(c) blending CT images and 2D photos from a patient to determine ideal procedure plans or to perform simulations for training purposes either without the server or with the server;

(d) tracking bone movement trajectories based on CT/MRI/X-Ray images either without the server or with the server;

(e) acquiring 2D videos to reconstruct 3D tooth models: the reconstruction could be accomplished either without the server or with the server;

(f) aggregating images from multiple imaging modalities (e.g. 2D X-ray, 3D surface scanning data, 3D CT, 4D simulations, etc) into a single view inside a browser 2D stitching & deformation of facial images with or without the server;

(g) measuring, annotating, pixel manipulating or simulation of 2D/3D/4D images with or without the server;

(h) comparing and/or image blending of pre and post procedural 2D/3D/4D images with or without the server;

(i) editing and simulation against 2D/3D/4D images with or without the server.

The invention optionally provides wherein the at least one first 2D medical image computer data file is stored and rendered on said into said 3D or 4D real time and manipulatable image display using the first or second browser without further processing by additional software or browser plugin on the first or second users' first or second mobile device or personal computer.

The invention optionally provides wherein the at least one first 2D medical image computer data file comprises, is decoded from, or is generated from, a DICOM-format medical image file.

The invention optionally provides wherein the at least one first 2D medical image computer data file is stored on non-transitory memory of a device, computer, PACS, browser, application, or server, or cloud storage location prior to said transferring step.

The invention optionally provides wherein the decoded DICOM-format medical image file format does not preserve the original resolution of the DICOM data and optionally includes partial DICOM data or annotation data and wherein the decoded DICOM-format medical image file is less than 50, 40, 30, 20, 10, or 5% of the file size of the original un-decoded DICOM-format medical image file.

The invention optionally provides wherein the first or second user is logged as a registered user of the computer data network browser, application, or server.

The invention optionally provides wherein the DICOM-format medical image file is preprocessed in a JavaScript™-based library as locally-opened DICOM data prior to said transferring step, wherein protected or private patient information is removed from the DICOM-format medical image file.

The invention optionally provides wherein the protected or private patient information is PHI BEFORE data in the DICOM-format medical image file, to protect confidential or private patient information, and wherein the patient information removal is completed without any extra private data removal processing software.

The invention optionally provides wherein the mobile device comprises preinstalled JavaScript™-based library software in non-transitory computer readable media that enables said visual display to render said 3D or 4D image data from multiple 2D medical image computer data files simultaneously.

The invention optionally provides wherein the 2D medical image computer data file are 2D x-ray image files and said rendering generates 3D and 4D x-ray images that are rotatable on said at least one first or second visual displays.

The invention optionally provides wherein said at least one first or second visual display further displays at least one of the at least one first or second mobile device or personal computer's device: entry point, entry direction, type, 3D mesh, image anatomy 3D mesh, physics attributes, rendered image analytic data, or rendering related data.

The invention optionally provides wherein the rendered 3D or 4D image data file formats include at least one selected from OBJ formats, 3D printer formats, CAD software file formats, Point Cloud formats, and any other 3D/4D imaging format. The invention optionally provides wherein the 3D or 4D image displays of the at least one first and second users are synchronized.

The invention optionally further comprises providing at least one of an annotation, text, and voice information between the first and second users that is transmitted to the other user's visual display in real time as inputted by the first or second user via the first or second browser.

The invention optionally provides wherein the transferring of the at least one 2D medical image computer data file further optionally includes searching for a plurality of second users with whom the 2D, 3D, or 4D medical image will be shared, based on user information data previously stored via the first browser by the first user.

Referring to FIG. 1, the Anatomy Reconstruction Cloud Service and the Patient Simulation Cloud Service are essential to the process of converting 2D images to 3D/4D images, and the distributions of 3D/4D images to the end users:

Anatomy Reconstruction Cloud Service receives multiple standard 2D x-ray and/or other radiation or sound imaging projections uploaded by medical professionals. The most common format for image storage is digital imaging and communications in medicine (DICOM). Upon receiving the raw patient data, the Anatomy Reconstruction Cloud Service can launch a series of algorithms, including projection algorithm, composition algorithm and extraction algorithm (FIG. 10) to build volumetric & polygonal mesh representation of the patient 3D model. The mesh-based 3D model is then sent back to the user for real-time display, since mesh format is typically much smaller than its volumetric equivalent, allowing for more efficient data transmission of 3D models back to the user. Common formats for the mesh-based 3D model are OBJ, COLLADA and X3D format.

It should be noted that the Anatomy Reconstruction Cloud Service can also be used to generate 4D models. The inputs to the cloud server will be a series of x-ray 2D images from multiple viewing angles, each series depicting a certain organ during a certain time period. In such an embodiment, a collection of mesh-based 3D models will be produced, each representing the patient anatomy at a certain time frame. 3D/4D mesh models are then displayed on each simulation system with the support of Anatomy Reconstruction Client Module, a software module that can be distributed to the simulation systems through different mechanisms. For example, Anatomy Reconstruction Client Module can be deployed to run inside a web browser, or be installed as a standalone application on the simulation system.

For simulation systems equipped with advanced graphics display card, the Anatomy Reconstruction Client Module can render not only 3D/4D mesh models, but also the volumetric representation of the patient 3D model, a format that carries more visualization details than the 3D/4D mesh format. The 3D images will be rendered on at least one image display devices, including using 3D projectors in a class room setting to allow users to watch and interact with 3D/4D models in an immersive environment, not unlike watching a 3D movie in a movie theater.

FIG. 1 is a flow diagram representing a non-limiting example of a projection algorithm that can be used in an invention that uses ray tracing method to construct one 3D grid for each angiogram (in other words, each 2D image is projected to a 3D volume). Each projection takes into account an original anatomical image as well as a detector (e.g., a C-ARM) location information. A ray tracing method will make corrections to a projection results when annotation data is present.

When performing the projection operation, a rotational matrix is constructed for each C-ARM position. This matrix is calculated by conducting multiplication operation with three matrices that represent pitch, roll and yaw rotations of the C-ARM. The resulting rotational matrix is then applied to evaluate each pixels on the 2D X-ray image, converting each 2D point to a 3D ray in the world space.

Figure 2:
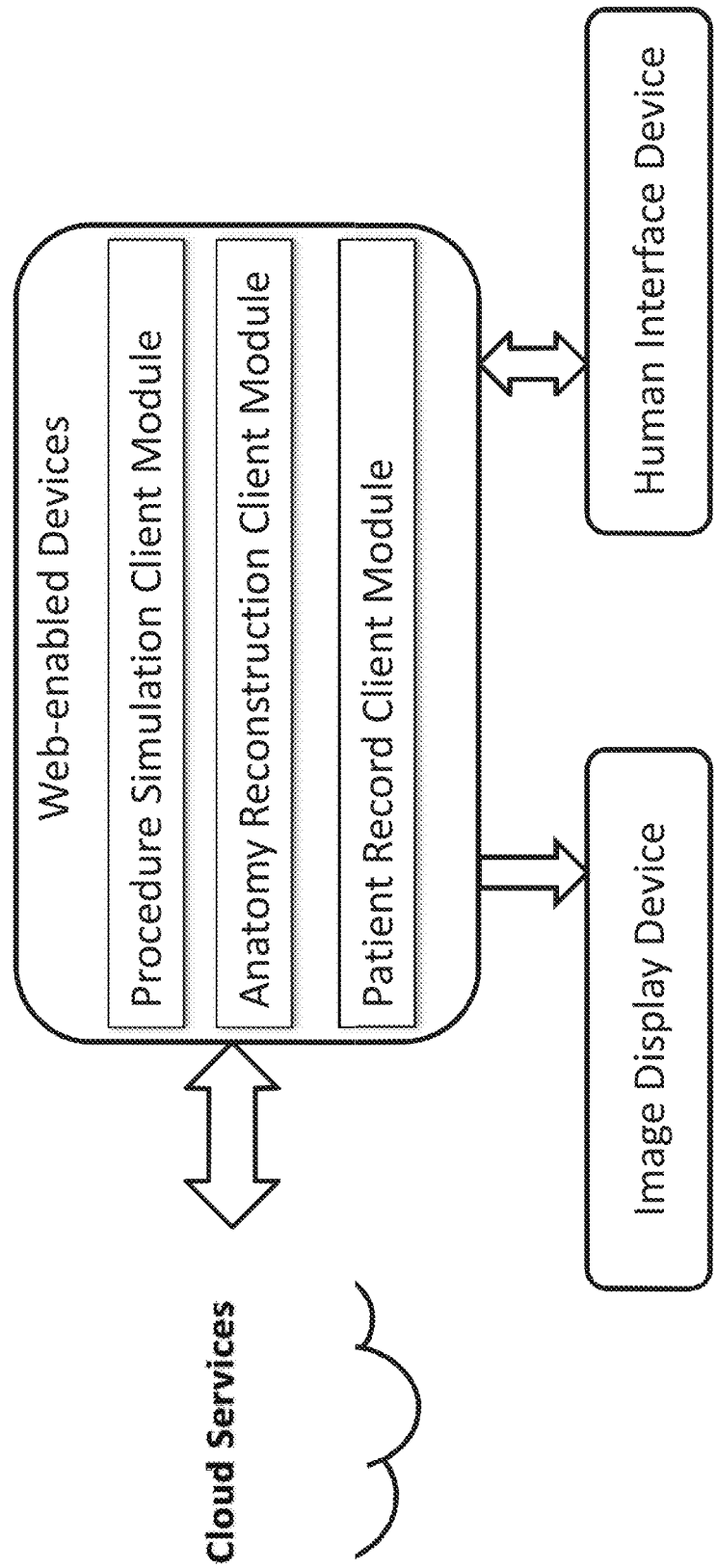
FIG. 2 is a flow diagram representing a non-limiting example of a composition algorithm that can be used in aspects of the invention that combines all "projection grids" into one. An inputs to a composition algorithm are 3D "projection grids" constructed from a previous step. Each grid represents a single 2D angiogram and/or other anatomical, image. Each grid cell now stores a collection of color information retrieved those "projection grids."

FIG. 2 is a flow diagram representing a non-limiting example of a composition algorithm that can be used in aspects of the invention that combines all "projection grids" into one. An inputs to a composition algorithm are 3D "projection grids" constructed from a previous step. Each grid represents a single 2D angiogram and/or other anatomical, image. Each grid cell now stores a collection of color information retrieved those "projection grids."

A main step of the composition algorithm involves evaluating errors introduced by the projection algorithm. The errors are often a result of random motion patterns of the C-ARMs, X-ray scatter effects or mismatches of heart cycles among different projection images. In order to correct the error, epipolar constraints are applied to compute the ioscenter offset, allowing feature points on multiple projections to be aligned correctly.

Figure 3:
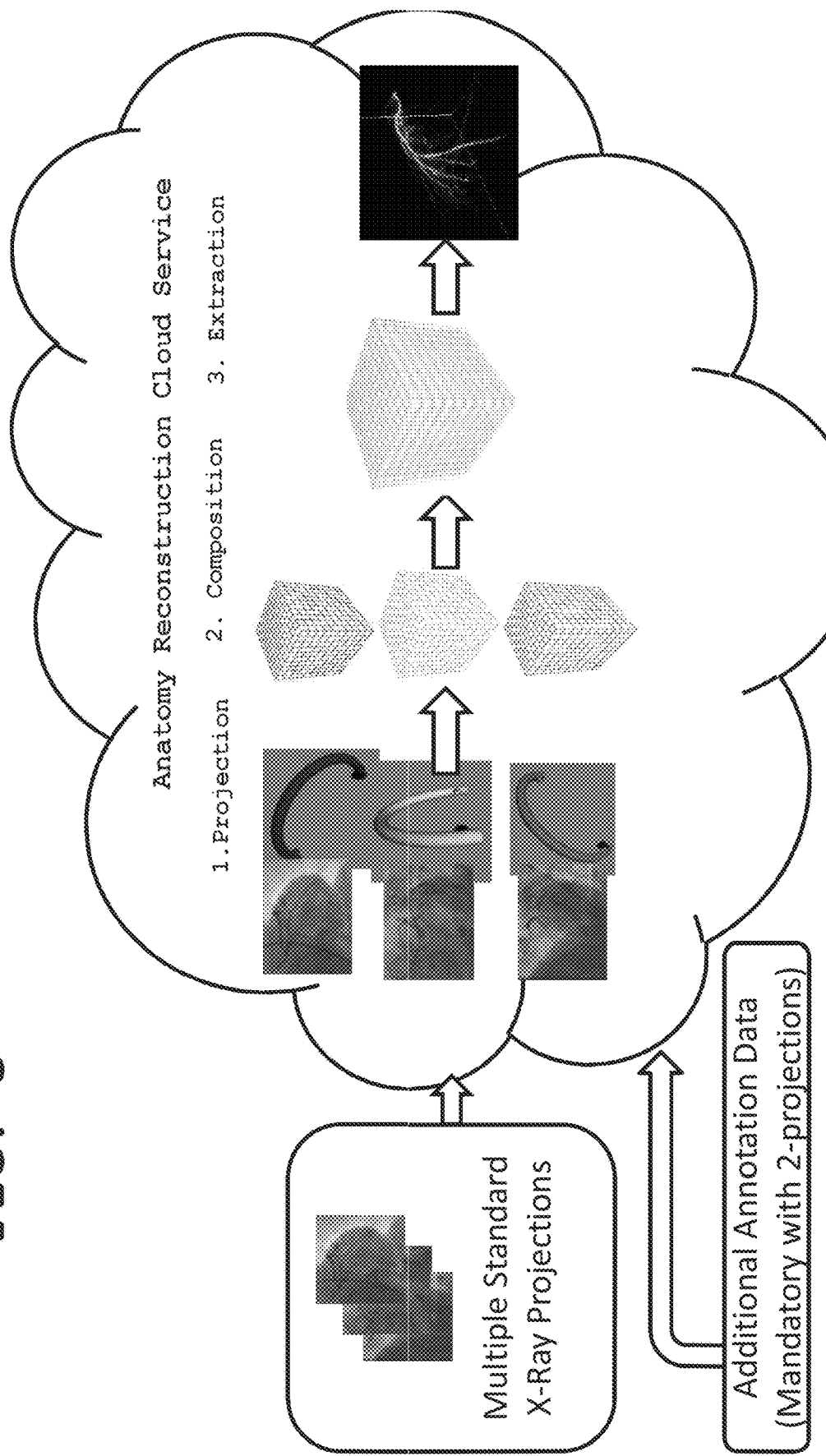
FIG. 3 is a flow diagram representing a non-limiting example of an extraction algorithm that can be used in aspects of the invention, that evaluates each grid cell's colors to determine its likelihood of being part of a valid anatomical structure, e.g., but not limited to, a valid blood vessel. Using spatial statistics and/or image processing techniques, a subset of grid cells and/or other anatomical structure can be identified as validated anatomical structures, e.g., but not limited to, blood vessels. A polygonal mesh of an isosurface can be constructed from an identified grid cells and/or other anatomical structure using surface extraction algorithms. An input to a composition algorithm is a consolidated 3D grid output from a previous step.

FIG. 3 is a flow diagram representing a non-limiting example of an extraction algorithm that can be used in aspects of the invention, that evaluates each grid cell's colors to determine its likelihood of being part of a valid anatomical structure, e.g., but not limited to, a valid blood vessel. Using spatial statistics and/or image processing techniques, an energy minimization function is applied to all grid cells, and a subset of grid cells and/or other anatomical structure can be identified as validated anatomical structures, e.g., but not limited to, blood vessels. A polygonal mesh of an isosurface can be constructed from an identified grid cells and/or other anatomical structure using surface extraction algorithms. An input to a composition algorithm is a consolidated 3D grid output from a previous step.

Energy functional minimization approaches have been considered for a wide array of multidimensional processing and/or information extraction tasks, including edge-preserving smoothing volumetric reconstruction, general image restoration, image in-painting, curve evolution, and/or segmentation, among others. These individual applications each have specific energy formulations which define a properties of a resulting processed fields (any image and/or 3D volumetric image, e.g., is a field).

Many known energy definitions are intended for processing of observations which are already reconstructed data (slices, images, and/or full 3D volumetric images). These energies, although not image reconstruction energies specifically, are important because they can be tied into an overall conglomerate energy, as defined below. Specific energy definitions with more and/or less limited scope of application are known and/or have been proposed for a number of different reasons, and/or include a number of different terms with different properties. By contrast, some configurations of aspects of the invention consolidate these terms into an overall conglomerate energy functional that has properties that are a function of all such terms, and/or at least of a plurality of specific energy definitions. For example, reconstruction algorithms previously have not been derived from material class decomposition constraints. Generally reconstruction algorithms have not been derived from an energy which contained at least one term that enforced an "N-ary" decomposition of an imaged volume— that is, a minimizer of an energy functional is an "N-ary" volumetric image.

The present invention introduces a new energy functional minimization scheme, which takes into account of vesselness of all 2D images for each 3D grid cell, the similarity of grayness of all 2D images for each 3D grid cell, and smoothness of vessel centerlines. Once the 3D volumetric image has been constructed, a marching cube algorithm will be applied to derive a polygonal mesh from the grid cells.

Background publications, such as U.S. Pat. No. 7,991,105, issued Aug. 2, 2011 (entirely incorporated herein by reference), builds 3D volumetric images based on special hardware and/or systems (e.g., rotational runs). Other 3D reconstruction methods, such as U.S. Pat. No. 6,047,080 issued on Apr. 4, 2000 (entirely incorporated herein by reference), are based on two standard views with a manual annotation process. The present invention uses multiple (e.g., >2 and/or >3) standard 2D x-ray and/or other radiation or sound imaging projections without a need for special hardware and/or systems (e.g., rotational runs) and/or pre-processing/analysis of a captured image data. When only two x-ray projections are available, the present invention still requires mandatory annotation data Unlike U.S. Pat. No. 6,047,080, the present invention involves a much simpler annotation process without the need of specifying vessel diameters for each annotation point due to the aforementioned energy functional minimization scheme.

Procedure Simulation Cloud Service enables medical professionals to perform interactive training based on real patient data. During the simulation training session, the Procedure Simulation Cloud Service also actively monitors the performance of trainees. Using the metrics gathered overtime, additional services such as hospital accreditation can be offered.

The Procedure Simulation Cloud Service receives inputs from haptics devices that are connected to each medical simulator. The cloud service offers a programming interface (API) which allow different types of motion detectors and force feedback devices to communicate with the cloud server. This programming interface enables a wide varieties of hardware platforms and simulators to consume the procedure simulation cloud service, a service that is based on real patient data and physics-based modeling of interactions between virtual medical devices and patient 3D models. As an example, touch-based tablets or even Kinect controller could serve as a motion detector to allow physicians to insert catheters or to deploy stents using touch gestures. Similarly, a high-fidelity endovascular simulator could also be connected to the cloud platform, allowing medical professionals to manipulate real medical equipment in performing online-based simulations with real-time force feedbacks.

Background publications, such as U.S. patent Ser. No. 9/800,104 issued on May 25, 2004 (entirely incorporated herein by reference), describes a simulation method and system based on distributive processing model used for training and educating healthcare teams. It allows multiple participants for individual team member roles at various connected simulation workstations. Those systems access pre-determined data from knowledge repository, and web is primarily used for data storage, not for computation of interactions between virtual medical devices and patient 3D models. A unique aspect of the present invention is that all input devices are accessing real patient data on the cloud server, including 3D/4D patient data reconstructed directly from 2D angiographic images. In addition, the Procedure Simulation Cloud Service conducts intensive computation on the cloud server, taking full advantage of the scalability and vast computing resources offered by modern cloud technologies.

Background publications, such as U.S. patent Ser. No. 10/860,707 issued on Apr. 14, 2009 and U.S. Pat. No. 7,991,105 issued Aug. 2, 2011 (each entirely incorporated herein by reference), described methods of constructing and visualization of 3D images based on 2D projection images. Those systems didn't address the need of performing simulation procedures on the patient-specific 3D models before the actual operation. It should be noted that these procedures involve delicate and coordinated hand movements, and how to move surgical instruments inside the patient anatomy successfully is a major challenge: a mistake in this difficult environment can be dangerous. Our present invention enables medical professionals to realistically interact with the virtual patient in a safe environment, and even perform the simulation with peers or mentors in a remote location.

The aforementioned programming interface allows wildly different motion devices to communicate with the Procedure Simulation Cloud Service. An illustrative embodiment of a haptics device provides a physical interface for performing medical and/or vascular-access procedures. More particularly, a user inserts an end effector, which is representative of a medical instrument (e.g., a needle, catheter, etc.) into a base of a haptics device and/or manipulates it to simulate needle insertion, cannulation, etc. In some embodiments, a simulator is capable of sensing an orientation of an end effector. For example, in some embodiments in which an end effector is a needle and/or catheter and/or both, a simulator is capable of sensing a orientation of a beveled end of a needle and/or catheter.

In accordance with an illustrative embodiment, a haptics-device base includes a receiver that receives an end effector when inserted into a haptics-device base. In some embodiments, a receiver provides one linear degree of freedom and/or two, independent, rotational degrees of freedom (i.e., pitch and/or yaw). In an illustrative embodiment, a linear degree of freedom enables a user to advance an end effector into a haptics-device base. This mimics an insertion of a needle and/or catheter into a patient's arm. A rotational degrees of freedom enable a user to move an engaged end effector up and/or down and/or left and/or right. This mimics a freedom of movement that a user has during an actual medical and/or vascular-access procedure.

Sensors within a haptics-device base monitor a motion and/or position of an end effector (e.g., by measuring an insertion displacement and/or pitch and/or yaw angles of a receiver, etc.). A sensors generate signals indicative of a monitored activity and/or transmit a signals to a data processing system.

The web-enabled data processing system processes an information acquired by a sensors. In conjunction with (i) a model of a medical instrument, such as a needle/catheter, and/or (ii) an anatomical model of at least a portion of an anatomy (e.g., human arm, etc.), a data processing system determines a effects (e.g., deformation, entry into a vein, etc.) of a user's manipulation of a needle/catheter on a surface and/or subsurface features of a body part on which a simulated medical and/or vascular-access procedure is being performed. Effects of a modeling are displayed by a simulator. An effects include, for example, a three-dimensional rendering of a body part of interest, a visual indication of a position of a needle/catheter relative to a body part, and/or a visual indication of how a needle/catheter affects that body part.

Furthermore, in some embodiments, using an anatomical model and/or an information obtained from a sensors, the web-enabled data processing system determines a various resistive forces that would arise if a user were manipulating a needle and/or catheter through an actual anatomy (e.g., blood vessels, etc.). A data processing system determines a resistive forces to simulate penetration and/or contact with various surface and/or subsurface features of human anatomy (e.g., a skin, a vein, harder structures such as ligaments, bones, etc.) a resistance advantageously varies with insertion displacement and/or a pitch and/or yaw of an end effector because a resistance is determined based on an interaction of a medical instrument model and/or an anatomical model. Resistance that would be experienced by a user manipulating an actual needle/catheter through an actual anatomy is represented by a force-feedback profile. A force-feedback profile, in accordance with an illustrative embodiment of aspects of the invention, is based on an interaction of a medical instrument model and/or an anatomical model. In some embodiments, a force-feedback model is based on a puncture strengths and/or stiffness of a various surface and/or subsurface features of a human anatomy, as represented by an anatomy model.

A web-enabled data processing system provides control signals that are based on a force-feedback profile to a haptics device. A haptics device uses a control signals to generate a resistance experienced by a user of a simulation system.

In some embodiments, a web-enabled data processing system also tracks a progress of a haptics device user during a simulated procedure. Steps taken by a user are compared against a set of rules that are stored in a web-enabled data processing system. An assessment comprises critical points and/or non-critical points. A simulator displays an assessment results when a user completes a simulated procedure.

Patient Record Cloud Service

Many countries have put in place registry system (e.g. National Cardiovascular Data Registry by American College of Cardiology) because it is broadly recognized that they can be valuable. But almost all the existing registries can have one or more the following limitations:

They provide one or more aspects of lack of clinical decision support.

They provide one or more aspects of lack of incorporation of medical images.

They are usually voluntarily used and physician engagement is often weak.

They often have shortcomings, such as but not limited to, one or more of use paper records, require retrospective review of medical records, are cumbersome and difficult to input data, and have a limited IT backbone that is suboptimal.

The data may be incomplete and error prone.

The quality of care assessments using benchmarking comes back to the physicians and hospitals as a report card but lacks guidance as to how to improve outcomes and reduce complications.

The data in the registry are often not used for other purposes. Business opportunities as well as some research initiatives are lost.

There is no standardization among countries that have a registry. Data are not interchangeable, comparable, or amenable to understanding important difference in patients around the world.

The present invention can provide in one or more aspects a Patient Record Cloud Service which incorporate patient medical images as well as the reconstructed 3D/4D models into data repositories. When a user uploads a collection of patient images to the cloud server, the raw patient images as well as the reconstructed 3D/4D data will be stored in the data repositories. With sufficient number of uploaded patient data, the Patient Record Cloud Service will be a potent research tool that permits focused analysis of clinical treatments, procedures, and outcomes of patients treated with medical procedures. Additionally, data collected can also be analyzed to assess compliance with clinical guideline recommendations, to assist in medical decision-making, to guide in-room procedures, and to assess the appropriateness of medical care provided for patients.

Figure 9:
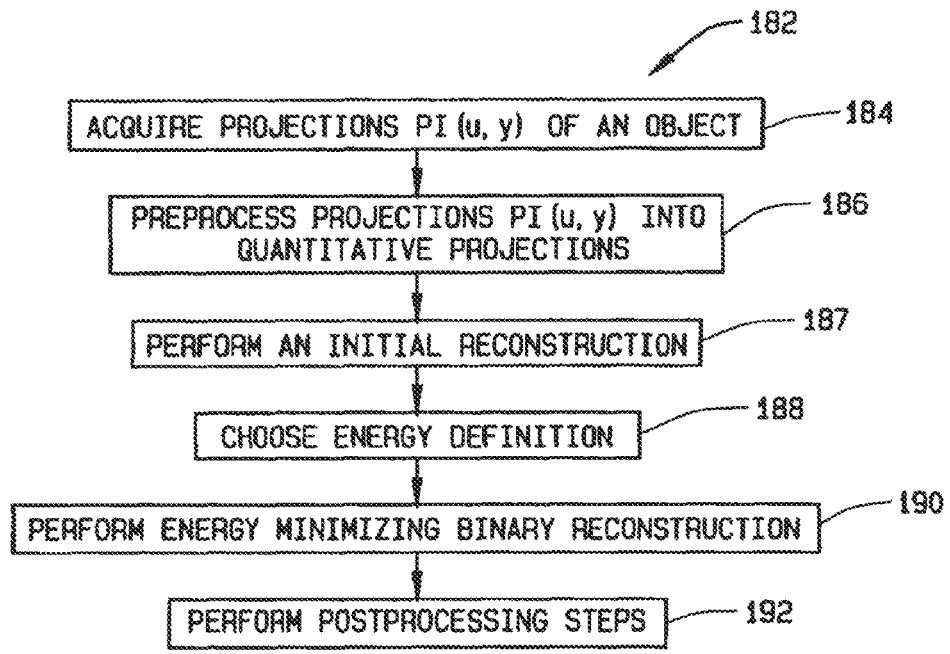
FIG. 9 is a flowchart illustrating yet another configuration of a volumetric image reconstruction method of aspects of the invention.

As used herein, a term "quantitative projections" refers to processed versions, qi (u,v), shown as 118 in FIG. 9, of a 2D image dataset, pi(u,v), shown as 102 in FIG. 9. A result of a processing is a set of projection radiographs, qi(u,v), where each pixel intensity in each projection radiograph indicates a percentage and/or amount (line integral, for example) of a material class along a ray corresponding to that pixel.

As used herein, a term "reprojections" refers to a projections obtained by applying a projection operator to an intermediate volumetric image in a reconstruction algorithm, where a projection geometry used in a computation of a reprojections is identical to a projection geometry that was used to acquire a corresponding original projection radiograph pi(u,v). For instance, Q(x,y,z) and/or B(x,y,z) may be "reprojected" to produce ri(u,v).

The terms "three dimensional (3D) volume" and/or "volumetric image" refer to a reconstructed 3D image of an object composed of voxels, which, in some of a examples herein, is a part of anatomy relevant for treatment and/or surgery. Volumetric images used herein include AT(x,y,z), Q(x,y,z), ΔQ(x,y,z), MC(x,y,z), and/or B(x,y,z). In some development, a variable, v, may indicate a continuous volumetric counterpart to any of a voxelized volumes, AT(x,y,z), Q(x,y,z), ΔQ(x,y,z), MC(x,y,z), and/or B(x,y,z).

A term "part of anatomy relevant for treatment and/or surgery" and/or "air-tissue volumetric image" refers to a three dimensional space occupied by an imaged part of anatomy relevant for treatment and/or surgery (as distinguished from a space occupied by a air around a part of anatomy relevant for treatment and/or surgery). This concept translates correspondingly to other imaged objects as well. An air-tissue volumetric image is denoted AT(x,y,z) herein.

A term "intermediate volumetric image" and/or "quantitative volumetric image" refers to any intermediate 3D representation of an imaged object. It may be a reconstructed volumetric image of material classes and/or a volumetric image of continuous-valued voxel intensities. An intermediate volumetric image is denoted Q(x,y,z). If it is a first such intermediate volumetric image in a reconstruction algorithm used for, e.g., deriving volumetric image statistics, it is called an "initial volumetric image"; an initial volumetric image is denoted Q0(x,y,z). Sometimes a volumetric update to an intermediate volumetric image is computed; these updates are denoted ΔQ(x,y,z).

A term "N-ary volumetric image" refers to any 3D representation of an imaged object in which each voxel assumes a value which is an intensity within a single material class, and/or a label corresponding to a single material class. An "approximately N-ary volumetric image" is similarly defined, but relaxes a constraint that all voxel values correspond to specific material classes, and/or allows a small fraction of a voxel values in a volumetric image to assume values that do not correspond to a material class. Both of these types of volumetric images are denoted B(x,y,z).

The term "reconstruction" refers to a process of creating a 3D volume (volumetric image) from a set of projection images. A "reconstruction algorithm" may comprise one and/or more reconstruction steps, which may each be applied in isolation and/or in concert with other reconstruction steps. A reconstruction algorithm may also iterate any number of reconstruction steps in any appropriate order.

Digital radiation analysis, e.g., but not limited to, tomosynthesis, is a three-dimensional imaging technique in which typically only a few, e.g., 3 to twenty, projection radiographs are acquired at varying radiation source focal spot positions with respect to an imaged object and/or a radiation detector. In many configurations, a radiation tube is an x-ray tube and/or a radiation detector is, correspondingly, an x-ray detector. For simplicity, only x-ray imaging configurations are discussed herein, but configurations of aspects of the invention are not limited to a use of a particular type of radiation. One configuration of digital tomosynthesis for mammography is described by Niklason, et al. in U.S. Pat. No. 5,872,828, entirely incorporated herein by reference.

Figure 4:
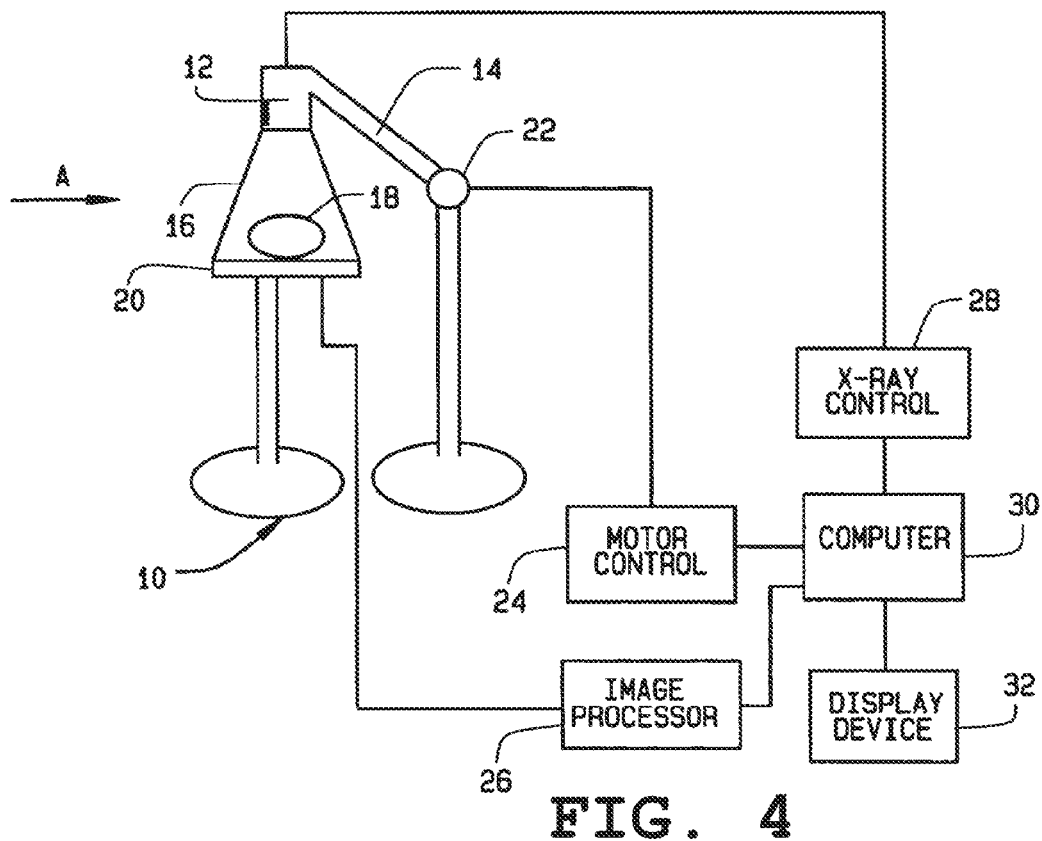
FIG. 4 is a block diagram representative of some configurations of an imaging system of aspects of the invention.

For example, and/or referring to FIG. 4, some configurations of digital imaging systems 10 of aspects of the invention comprise an x-ray tube 12 on a gantry arm 14. X-ray tube 12 projects radiation 16 towards an object 18 disposed between x-ray tube 12 and/or a detector array 20, which is used to acquire projection radiographs. Gantry arm 14 can remain stationary, provide sections, and/or rotate about a pivot point 22 to enable a plurality of projection radiographs to be obtained using different focal spot positions of x-ray tube 12. Digital imaging system 10 in some configurations also comprises a motor controller 24 to rotate gantry arm 14 around stationary and/or pivot point 22 and/or an image acquisition and/or processing device 26 that receives and/or processes a acquired projection radiographs. Also provided in some configurations is an x-ray controller 28 to control an operation of x-ray tube 12. An entire apparatus 10 in some configurations is under control of a computer 30 which is responsive to operator input, and/or a display device 32 and/or a printer may be provided in some configurations to display and/or print processed images of object 18. Although not shown in FIG. 4, archival mass and/or removable storage and/or a network connection to a public and/or private network may also be provided for acquired data and/or images. In various configurations, software and/or firmware is provided to configure computer 30 and/or image acquisition and/or processing device 26 to control motor controller 24, x-ray tube 12, detector array 20, display device 32, and/or display device 32 to acquire projection images of an object 18 (for example, a part of anatomy relevant for treatment and/or surgery) and/or to configure computer 30 and/or image acquisition and/or processing device 26 to perform procedures described below for reconstructing volumetric images and/or displaying a reconstructed volumetric images on display device 32 and/or elsewhere. In some configurations, a reconstructed volumetric images can be stored in a memory (not shown) and/or displayed at a later time.

Figure 5:
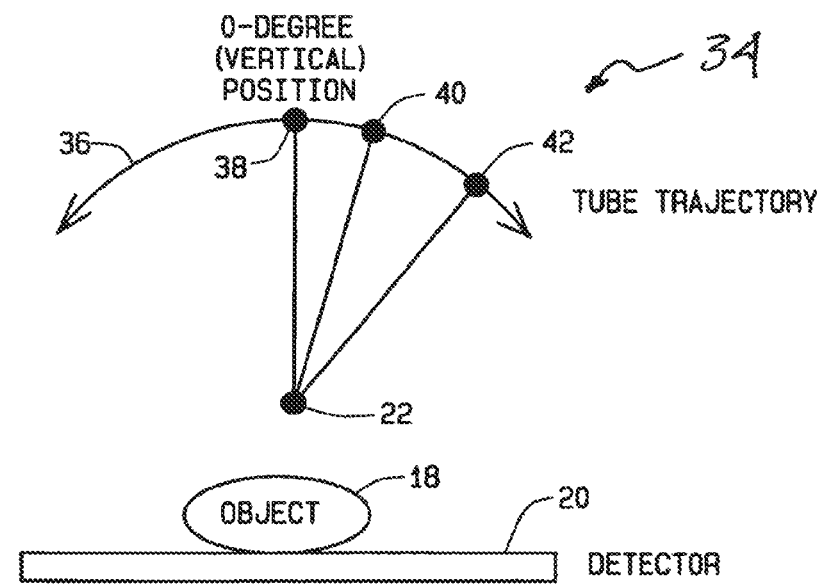
FIG. 5 is an illustration of system geometry of various configurations of imaging systems represented by FIG. 4.
Figure 8:
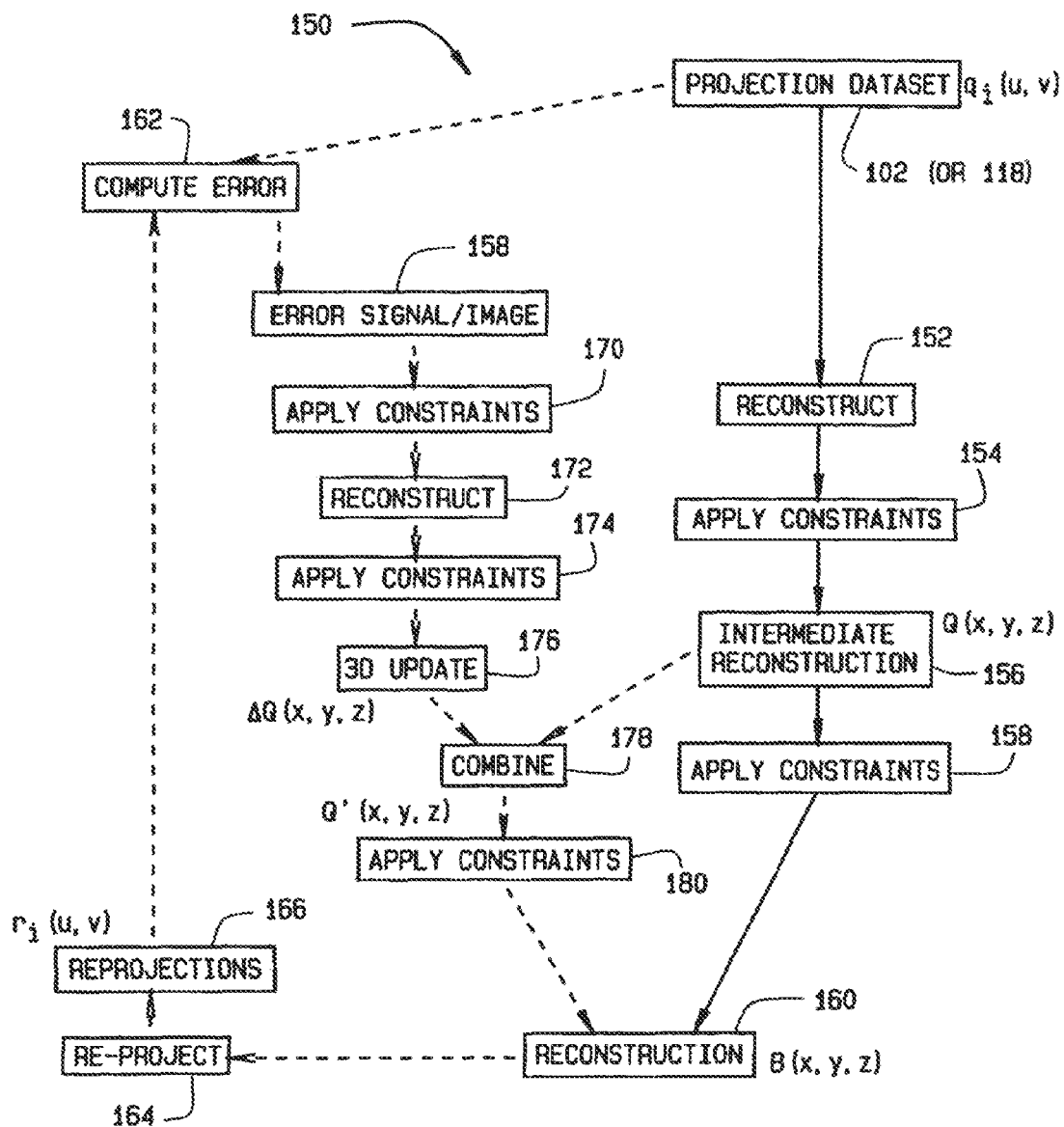
FIG. 8 is a flowchart illustrating a configuration of aspects of the invention in which an algorithmic reconstruction is used.

A nominal geometry 34 of imaging system 10 of FIG. 4 for part of anatomy relevant for treatment and/or surgery imaging is illustrated in FIG. 5. As viewed from arrow in FIG. 5, radiation detector 20 and/or imaged object 18 (in this configuration, a part of anatomy relevant for treatment and/or surgery) are assumed to be stationary, while x-ray tube 12 attached to gantry arm 14 can be stationary, can provide serial sections, and/or rotates around pivot point 22 along a trajectory 36 to acquire projection images from different views. In FIG. 8, three focal spot positions are shown from which projection images can be obtained, namely, focal spot position 38, focal spot position 40, and/or focal spot position 42. More typically, however, two and/or more projection radiographs are acquired at varying positions, not all of which are separately represented in FIG. 3,6.

In some configurations of imaging system 10, as shown in FIGS. 4 and 5 gantry pivot point 22 is located above detector 20, and/or a distance from focal spot 38 (and/or other focal spots) to pivot point 22 is optimized for one and/or more of stationary, provide sections, and/or rotational sections, as projected into one and/or more planes, e.g., as shown in FIG. 8. A sectional and/or angular range of gantry arm 14 can include 0 degrees, and/or for rotational sections, e.g., from −25° to +25° degrees, including using 0 degrees for regular radiation 2D imaging, relative to a vertical position of gantry arm 14, exemplified in FIG. 8 by focal spot position 38. Other configurations may include, for example, a moving detector, multiple detectors, multiple x-ray sources, and/or so forth. In some configurations, 2 and/or more (e.g., 2 and/or 3 and/or more) 2D projection radiographs are acquired, for x-ray tube 12 positions covering a sectional and/or angular range (including using 0 degrees for non-rotation images) of gantry arm 14, in 1-15° increments, e.g., 5 degrees. This set projection radiographs is referred to herein as a 2D image dataset. Using a 2D image dataset, image processor 26 and/or computer 30 can reconstruct a volumetric image representative of a 3D characteristics and/or structure within a full three-dimensional volume of imaged object 18 using an appropriate reconstruction algorithms, e.g., through a use of image analysis that can include one and/or more algorithms selected from one and/or more of projection, composition and/or extraction algorithms that convert 2 and/or more and/or 3 and/or more 2D images to 3D and/or 4D images. Image processor 26 and/or computer 30 are not necessarily separate components. Various different reconstruction algorithms are known and/or as described herein. These known reconstruction algorithms have different performance characteristics related to image quality (e.g., contrast, artifacts and/or noise) and/or to computational requirements (e.g., memory, speed). See, for example, Kak, et al., "Principles of Computerized Tomographic Imaging," IEEE Press, 1988.

Configurations of aspects of the invention for quantitative volumetric and/or 4D image reconstruction are not limited to an imaging system geometry as described in FIG. 8. In particular, quantitative radiation image reconstruction configurations of aspects of the invention can be used in other, more general situations, where a goal is to reconstruct quantitative three-dimensional information about an imaged object from relatively few projection radiographs. More particularly, in some configurations of aspects of the invention, various reconstruction algorithms known in a art can be used to estimate an initial three-dimensional volumetric image 112 and/or 124 in FIG. 6, for example, that is then further processed and/or iteratively updated according to aspects of the invention.

A part of anatomy relevant for treatment and/or surgery consists almost entirely of two distinct material classes of tissues, namely any tissue or vessel and/or glandular-like tissue (i.e., radiographically equivalent to fibrotisue). A very small fraction of a part of anatomy relevant for treatment and/or surgery may consist of calcium salts in very small quantities, usually termed "target tissue component or vessel and/or medical device or treatment." Although configurations of aspects of the invention are described herein that deal with all three types of part of anatomy relevant for treatment and/or surgery, some configurations focus on fatty and/or glandular-like tissues. These two tissues have distinct x-ray attenuation spectra, making it possible, in one embodiment, to compute a quantitative projection image by decomposing a part of anatomy relevant for treatment and/or surgery x-ray projection radiograph into relative amounts of fatty and/or glandular-like tissue at each image pixel. Such a decomposition is made possible using additional information, which, in some configurations, includes system 10 calibration data, part of anatomy relevant for treatment and/or surgery thickness, and/or x-ray technique information. Cancerous lesions have attenuation properties that are very similar to normal tissue, and/or which can therefore be accommodated with a two-tissue configuration, wherein a lesions appear glandular-like. On a other hand, target tissue component or vessel and/or medical device or treatment represent an exception to a two tissue composition assumption in that target tissue component or vessel and/or medical device or treatment include highly attenuating material (namely, calcium salts) having very different radiographic properties than either fatty and/or other soft tissue. However, because target tissue component or vessel and/or medical device or treatment are typically very small, covering only a few pixels in a projection image, their effect on quantitative imaging is very limited. Further, specific methods have been developed to detect and/or compensate for local "outliers" caused by target tissue component or vessel and/or medical device or treatment, as known in a art and/or as described herein.

Figure 6:
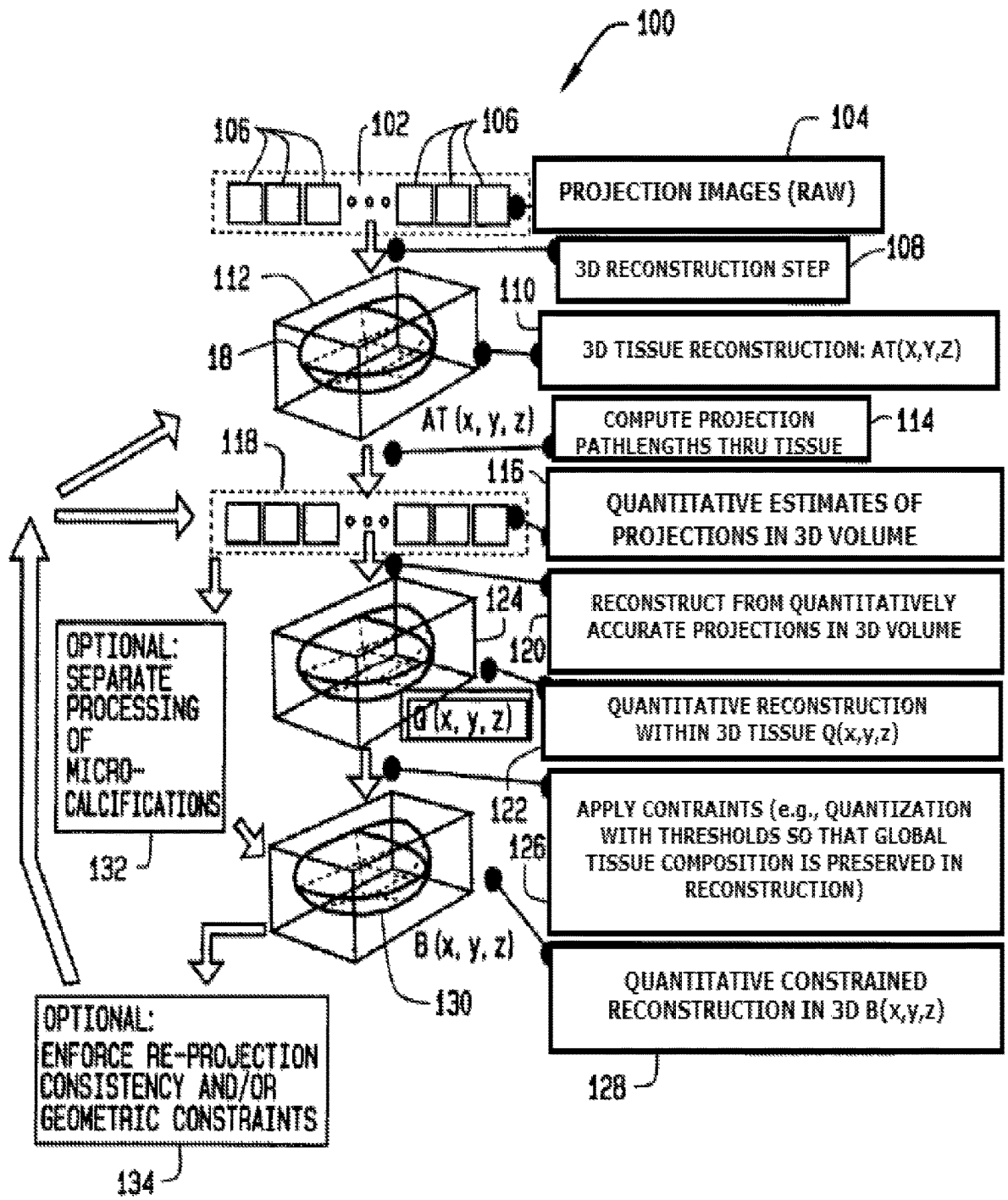
FIG. 6 is a combination flowchart and/or pictorial diagram of steps and/or intermediate results in a configuration of aspects of the invention in which a volumetric image containing quantitative composition estimates of three-dimensional part of anatomy relevant for treatment and/or surgery volumes are reconstructed.

In configurations of aspects of the invention, e.g., as shown in FIG. 4-6, prior knowledge about object 18 (e.g., for a part of anatomy relevant for treatment and/or surgery as object 18, a underlying anatomy and/or its x-ray properties, maybe in combination with other, additional information described herein below and/or as known in a art) is used to arrive at a reconstructed volumetric image that quantitatively reflects a actual composition of object 18 in terms of a specified set of material classes assumed and/or hypothesized to comprise most of a volume of object 18, as well as positional information, which can further include positional information about medical instruments and/or treatments. A volumetric image that is a output of a reconstruction is referred to as either "essentially N-ary" and/or "approximately N-ary." By "essentially N-ary" and/or "approximately N-ary" (and/or other similarly qualified "N-ary" volumetric images), it is meant that most of a voxel values in a reconstructed volumetric image correspond to exactly one of a set of a selected number N (where N is two and/or more) material classes assumed and/or hypothesized to comprise most of a volume of object 18. A smaller portion of a reconstructed volumetric image of a object may and/or may not be labeled as one and/or a small number of other hypothesized material classes that comprise a remaining part of a volume of object 18. If all of a composition of a reconstructed volumetric image of a object is represented by voxels exclusively from a set of N material classes, a construction is referred to as "strictly N-ary." An "N-ary volumetric image" with no other qualifications includes within its scope both approximately N-ary volumetric images and/or strictly N-ary volumetric images. For N=2, a volumetric image is called "binary".

In some configurations and/or referring to flow chart 100 of FIG. 6, a method useful for reconstructing quantitative three-dimensional volumetric images of objects (e.g., part of anatomy relevant for treatment and/or surgery) comprises a plurality of steps, some of which are optional and/or some of which may be satisfactorily performed using any of a plurality of different methods. It is also not necessary in all configurations of aspects of the invention to perform all of a steps of flow chart 100 in an exact sequence shown in FIG. 9. A technical effect of apparatus 10 (or other apparatus configurations of aspects of the invention) is achieved by a user operating an apparatus to acquire, at 104, a 2D image dataset 102 that comprises a set of projection radiographs 106 of an object 18, such as a part of anatomy relevant for treatment and/or surgery, from a same and/or different projection angle s and/or sections and/or reconstructing a volumetric image of an imaged object from a projection images.

The result of a decomposition of a projection radiograph image, into its fatty and/or glandular-like, and/or other soft and/or hard tissue components, is a new image and/or set of images for each x-ray projection radiograph. A new image and/or set of images, for example, capture one and/or more of a position, percent tissue and/or an associated height of a tissue. These new images are referred to as quantitative projections. This approach to quantitative projection imaging is described by Kaufhold et al., "A calibration approach to tissue composition estimation in digital mammography," Med. Phys. 29(8), August 2002, pp. 1867-1880. See also published U.S. patent applications Ser. Nos. 2003/0072417, "Method and/or apparatus for calibrating an image system," and/or 2003/0072409, "Methods and/or apparatus for estimating a material composition of an imaged object," which are entirely incorporated herein by reference.

In some configurations, a projection images that are part of a 2D image dataset 102 are, and/or are assumed to be, scatter-free and/or have had appropriate corrections made for imaging physics and/or acquisition electronics. Such scatter correction, imaging physics corrections, and/or corrections for imaging electronics are described elsewhere. For example, see Gonzalez Trotter, et al., "Scatter Correction in Tomosynthesis Imaging for Mammography," 6th International Workshop on Digital Mammography, 2002, and/or Gonzalez Trotter, et al. "Thickness-dependent scatter correction algorithm for digital mammography," SPIE, as well as U.S. Pat. No. 6,633,626, "Methods and/or apparatus for correcting scatter," and/or U.S. Patent Application Publication No. 2003/021507, "Scatter correction method for non-stationary x-ray acquisitions" (each entirely incorporated herein by reference).

Additional information that may be provided as a result of processing of a 2D data set using various algorithms, e.g., projection, composition and/or extraction, relevant 3D and/or 4D volumetric images are provided, including real time positioning of both tissue to be treated, as well as associated medical devices and/or treatments. A decomposition and/or other suitable processing of a projection images includes an indicator of a part of anatomy relevant for treatment and/or surgery region, an indicator for a part of anatomy relevant for treatment and/or surgery edge, and/or summary composition statistics. More specifically, a part of anatomy relevant for treatment and/or surgery is an image region in which a part of anatomy relevant for treatment and/or surgery is oriented with a detector 20, such that x-rays pass through tissue relevant for imaging. A part of anatomy relevant for treatment and/or surgery edge is a contour in a projection images defined by a part of anatomy relevant for treatment and/or surgery.

A part of anatomy relevant for treatment and/or surgery edge is a boundary of a region of a projection radiograph in which x-ray beam 16 as shown in FIG. 4 passes through some amount of tissue. Indicators for part of anatomy relevant for treatment and/or surgery region, and/or part of anatomy relevant for treatment and/or surgery edge, are essentially curves separating two image regions from each other. These indicators can be generated in a form of an image, and/or any other appropriate form. From a decomposition of a projection radiograph, other additional parameters can be computed. For example, a composition "summary statistics" include useful global information about a part of anatomy relevant for treatment and/or surgery, such as overall part of anatomy relevant for treatment and/or surgery composition.

Thus, in at least some configurations, but not necessarily all configurations, "pre-processing so that processed projection images are quantitative" is related to determination steps concerning a line-integral of an attenuation coefficient, and/or a composition along a ray. In some configurations, analytical expressions rather than calibration curves are used to perform these steps.

In one configuration of aspects of the invention, a generation of quantitative projection images from a 2D image dataset follows a similar procedure as for a standard two-dimensional quantitative composition estimation for standard mammograms discussed above, and/or an image include a same information as in standard projection imaging. However, in processing 2D image datasets, a system geometry change from view to view can be taken into account.

In some configurations, a part of anatomy relevant for treatment and/or surgery thickness and/or 2D image dataset 102 as shown in FIG. 6 are input to a quantitative reconstruction at 104. 2D image data is assumed to be scatter-free and/or appropriately corrected for imaging physics and/or acquisition electronics effects. In some other configurations, an image are normalized such that, for each pixel, an average attenuation along a path of a corresponding ray of radiation is indicated, with reference to an assumed object 18 of a fixed thickness, corresponding to a part of anatomy relevant for treatment and/or surgery thickness. An indicator of a projected edge of an imaged part of anatomy relevant for treatment and/or surgery, and/or an indicator for a part of anatomy relevant for treatment and/or surgery region may also be provided. A global part of anatomy relevant for treatment and/or surgery composition metric for at least one of an image in 2D image dataset 102 may be provided, as well as other "summary statistics." Furthermore, additional information about a part of anatomy relevant for treatment and/or surgery shape may be available through another sensor. For example, a camera (not shown in Figures) can be used to provide information about a shape of a part of anatomy relevant for treatment and/or surgery in a part of anatomy relevant for treatment and/or surgery region. This information may also be provided as additional input.

From 2D image dataset 102, as shown in FIG. 6, an estimate of a geometry of a three-dimensional volume that contains part of anatomy relevant for treatment and/or surgery (i.e., some amount of fatty and/or material) is determined at 108. This estimate is a description of a physical object shape and/or location in three dimensions, and/or is referred to as a Part of anatomy relevant for treatment and/or surgery volumetric image. This estimate produces an air/tissue volumetric image of an imaged volume at 110, $AT(x,y,z)$, where $AT(x,y,z)$ is "1" where $(x,y,z)$ coordinates are at a point "inside" a part of anatomy relevant for treatment and/or surgery (tissue), and/or $AT(x,y,z)$ is "0" where $(x,y,z)$ coordinates are at a point "outside" a part of anatomy relevant for treatment and/or surgery (air). AT can have other representations as well. For example, AT can be represented as a surface that separates part of anatomy relevant for treatment and/or surgery from a surrounding space and/or air. Either representation has substantially a same information with respect to a part of anatomy relevant for treatment and/or surgery, $AT(x,y,z)$. That is, a surface model for a part of anatomy relevant for treatment and/or surgery can be used to derive a volume, $AT(x,y,z)$, and/or $AT(x,y,z)$ can be used to derive a surface model of a part of anatomy relevant for treatment and/or surgery, i.e. A surface that separates space and/or air from a part of anatomy relevant for treatment and/or surgery. An air/tissue volumetric image 112 can be determined from a projection images, and/or from additional information (e.g., compression paddle readout, and/or additional sensor), and/or a combination thereof.

In some configurations, part of anatomy relevant for treatment and/or surgery, $AT(x,y,z)$, which is a model of a three-dimensional geometry of a surface of an imaged part of anatomy relevant for treatment and/or surgery, is reconstructed first for steps 108 and/or 110. This reconstruction may be accomplished, for example, by performing a preliminary three-dimensional reconstruction in conjunction with an N-ary quantization (e.g., (air, tissue) binary quantization). Reconstruction methods that incorporate information about a detected part of anatomy relevant for treatment and/or surgery edge (e.g., skinline) in at least one of an image in 2D image dataset 102 may be used for this purpose. Likewise, smoothness constraints for a 3D skinline may be incorporated into a N-ary volumetric image. If available, additional information about a part of anatomy relevant for treatment and/or surgery shape which may be available from some other sensor (a camera, e.g.) may also be used to constrain a N-ary volumetric image of a part of anatomy relevant for treatment and/or surgery. A part of anatomy relevant for treatment and/or surgery, and/or air/tissue volumetric image, $AT(x,y,z)$, is therefore a three-dimensional mask for a part of anatomy relevant for treatment and/or surgery that describes an interior and/or an exterior of a part of anatomy relevant for treatment and/or surgery.

The air/tissue reconstruction (or substitute methodology) is not required in all configurations of aspects of the invention. In some configurations, a reconstruction of a part of anatomy relevant for treatment and/or surgery at 108 and/or an interior structures of a part of anatomy relevant for treatment and/or surgery at 122 are performed simultaneously in a single processing step.

From air/tissue volumetric image 112, a x-ray path lengths through tissue (i.e., a path lengths through a volume defined by AT(x,y,z)) for each projection radiograph in a 2D image dataset are determined at 114. From these path lengths and/or 2D image dataset 106, an estimate of a percentage of part of anatomy relevant for treatment and/or surgery composition is determined at 116 for each projection radiograph. To convert 2D image dataset 102 into a quantitative percentage projection dataset 118, previously-acquired, and/or otherwise predetermined, calibration curves are used to estimate a relative amounts of individual tissue composing each pixel in each projection radiograph. A resulting images are referred to as quantitative projection estimates 118, and/or qi(u,v). That is, a quantitative percentage projection estimates are no longer simply intensities, but rather measured amounts of tissue along a ray corresponding to an x-ray incident on a pixel. Furthermore, from these quantitative percentage projection estimates, a summary statistic for a overall percentage tissue may be determined for a plurality of x-ray projection radiographs.

In yet another configuration, a preprocessing step is applied to 2D image dataset 102 that compensates for a effect of reduced tissue thickness near a skinline. This preprocessing step, referred to as "thickness compensation" for two-dimensional projection images, proceeds as though any tissue or vessel were added in a regions of reduced thickness so as to achieve a full thickness. This step circumvents a three-dimensional part of anatomy relevant for treatment and/or surgery reconstruction, and/or a quantitative reconstruction based on these preprocessed images will generally generate reliable tissue characteristic estimates at any location within a volume of an imaged part of anatomy relevant for treatment and/or surgery (i.e., a part of anatomy relevant for treatment and/or surgery). In other configurations, and/or in addition to thickness compensation, in a region in which x-rays do not pass through any part of anatomy relevant for treatment and/or surgery, a projection images are modified as though an x-rays and/or other radiation pass through a full thickness of any tissue or vessel.

In some configurations, quantitative projections 118 are obtained by first computing a projection ray path length through a part of anatomy relevant for treatment and/or surgery (i.e., a volume defined by a part of anatomy relevant for treatment and/or surgery AT(x,y,z)) for each pixel in each projection image, and/or then determining a quantitative projection using appropriate calibration curves for a corresponding tissue thickness. Also in some configurations, a part of anatomy relevant for treatment and/or surgery AT(x,y,z) determination at 108 and/or 110 is not determined first, but rather assumptions about a shape of a part of anatomy relevant for treatment and/or surgery in a region (e.g., a model of a thickness as a function of a distance from a skin line and/or a compressed thickness) are used to generate a quantitative projections directly. In these configurations, a determination of a part of anatomy relevant for treatment and/or surgery is not required for a generation of a quantitative projections 118. In other configurations, projection images 104 are normalized such that, for each pixel, an average attenuation is indicated. This average attenuation is referenced to a path length through a volume of constant thickness. A average attenuations are used directly as input for reconstruction at 120.

Using a set of quantitative projections 118, one step of a reconstruction algorithm may be used at 120 to estimate intensities in a part of anatomy relevant for treatment and/or surgery, i.e., inside a three-dimensional volume defined by AT(x,y,z). More particularly, a reconstructed intermediate volumetric image, Q(x,y,z), takes on non-zero values only where AT(x,y,z) is "1" at 122. This volumetric image, Q(x,y,z), referred to herein as a quantitative volumetric image of a part of anatomy relevant for treatment and/or surgery in a part of anatomy relevant for treatment and/or surgery, corresponds to intensity values (typically estimated attenuation values) inside a part of anatomy relevant for treatment and/or surgery estimate, AT(x,y,z) 124. Similarly, with known reconstruction algorithms, a quantitative volumetric image of a part of anatomy relevant for treatment and/or surgery in a part of anatomy relevant for treatment and/or surgery 124 takes on numerical intensity values between intensities which correspond to all and/or all any tissue or vessel for a given voxel, suggesting that at certain locations within a part of anatomy relevant for treatment and/or surgery, a structure is mixed. However, a part of anatomy is distinct. That is, ignoring partial volume effects, at any given (x,y,z) coordinate, an intensities in an N-ary volumetric image of an imaged part of anatomy relevant for treatment and/or surgery 130, for example, are either fatty and/or glandular. In various configurations of aspects of the invention, a quantitative volumetric image is configured to reflect that fact. Thus, in some configurations of aspects of the invention, an N-ary voxel constraint is applied at 126 to a quantitative volumetric image, Q(x,y,z) so that a volumetric image at any voxel is, for example, either fatty and/or tissue. For example, a volumetric image is an N-ary volumetric image that labels tissue "2" and/or any tissue or vessel "1" at every voxel in a volumetric image, rather than labeling voxels as a mixture of material classes corresponding to mixtures of tissue. To arrive at an N-ary volumetric image from a quantitative volumetric image, in some configurations of aspects of the invention, a plurality of constraints are applied to a reconstructed volume at 126. A constraint set, for example, can include a plurality of models that constrain an anatomical morphology, intensities, and/or summary statistics of a quantitative volumetric image determined at 122. An individual constraints and/or a constraint set is discussed in more detail herein below, and/or in combination with what is known in an art. At step 128, a constraint set is used to map a continuous voxel intensities in a volumetric image to intensities of a constrained (e.g., essentially N-ary) quantitative reconstructed volume 130. A separate processing step 132 may be used to separately generate a three-dimensional volumetric image of target tissue component or vessel and/or medical device or treatment contained in a part of anatomy relevant for treatment and/or surgery. This additional information in some configurations is injected into N-ary reconstructed volume 130 of a part of anatomy relevant for treatment and/or surgery. In some configurations of aspects of the invention, N-ary quantitative reconstructed volume 130 is checked at 134 for consistency against a data (e.g., a quantitative percentage projection estimates), itself, which represents another constraint. This consistency check can be used to update AT(x,y,z), a part of anatomy relevant for treatment and/or surgery estimate 124, and/or to iteratively update a reconstructed quantitative volumetric image in a part of anatomy relevant for treatment and/or surgery, Q(x,y,z), as indicated by a arrows in FIG. 6.

Figure 10:
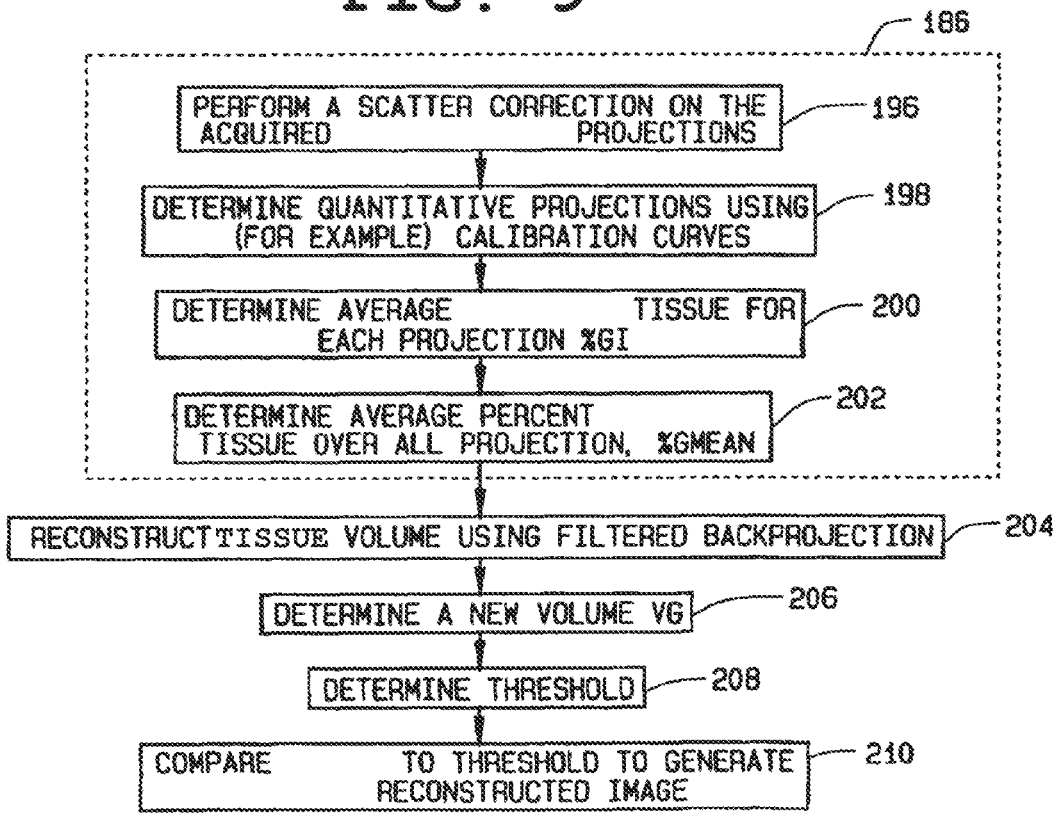
FIG. 10 is a flow chart representing configurations of aspects of the invention in which a scatter correction is performed on acquired image projections.

Referring to a details of step 186 provided in a flow chart of FIG. 9-10, in some configurations, a scatter correction is performed at 196 on an acquired projections. Quantitative projections (e.g., but not limited to, percentage vs. percentage fat) are determined at 198 using calibration curves. Composition summary statistics may be computed. Specifically, an average percent tissue for each projection, % Gi, is determined at 200, and/or an average percent tissue over all projections, % Gmean, is determined at 202 in accordance with an expression which can be written as % Gmean=(% G1+% G2+% G3+ . . . +% Gn)/n. In other configurations, % Gi is determined for only a subset of a projection images, and/or only for a region of interest (ROI) within a projections. Neglecting boundary effects, an overall composition % Gi is constant across different projection images. Thus, a value from a single projection image can be used in some configurations. In yet another configuration, quantitative projections are obtained by using an analytic approach, which may be used in combination with a pre-processing step for scatter correction.

Figure 11:
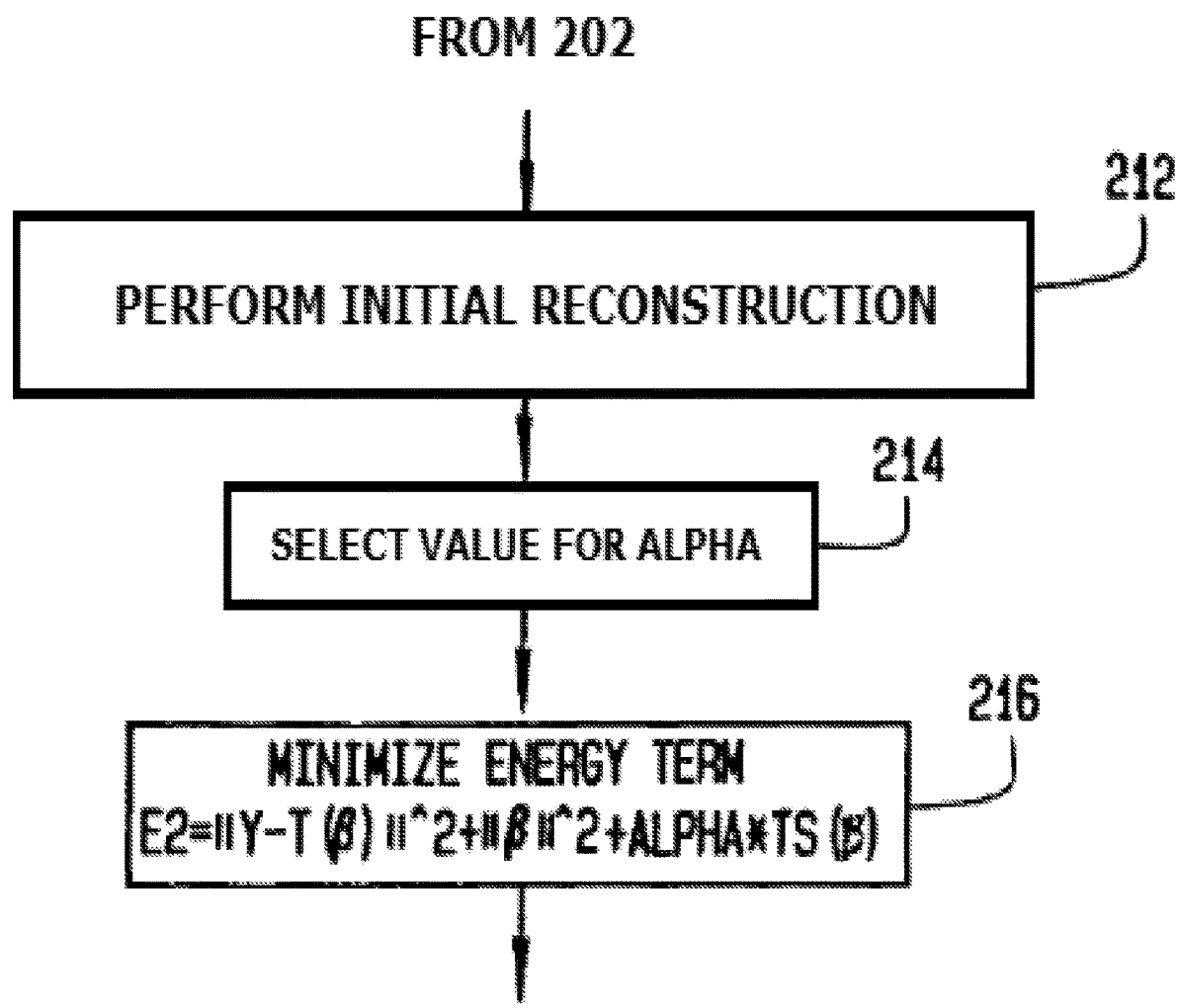
FIG. 11 is a flow chart representing a method of defining an energy minimization term, such as E2, and/or parameters of an energy minimization term that can be set using statistics gathered from an initial volumetric image.

In some configurations, and/or referring to FIG. 10, an initial estimate of a quantitative volumetric image of a part of anatomy relevant for treatment and/or surgery, Q, is reconstructed at 204, for example, via filtered back projection and/or some other reconstruction algorithm of a prior art, and/or using one and/or more algorithms described herein, e.g., projection, composition, and/or extraction. Using a suitable method, for example, thresholding and/or a method using a three-dimensional morphology, determine an updated air-tissue volumetric image, AT, from Q at 206. This determination is performed in some configurations by thresholding a volumetric image to separate voxels corresponding to tissue from voxels corresponding to air. From a distribution (e.g., histogram) of voxel intensities in Q that are also located within a part of anatomy relevant for treatment and/or surgery (i.e., where AT indicates that a voxel corresponds to tissue), a threshold TG is determined at 208 such that a number of voxels in Q (restricted to a space where AT indicates tissue) above a threshold divided by a total number of voxels in AT is % G mean/100. In some configurations, a threshold TG is determined as a function of a composition in a single projection, and/or a corresponding subvolume of a part of anatomy relevant for treatment and/or surgery AT that is projected onto a detector for that projection is used as a reference volume for a determination of that threshold. Then, voxel values in Q, for voxels that are located within a part of anatomy relevant for treatment and/or surgery AT, similarly, are compared to threshold TG at 210. Those above a threshold are assigned to 1, while those below it are assigned to zero. A resulting volumetric image is improved iteratively in some configurations, e.g., by using an approach similar to that shown in FIG. 11. These values 0 and/or 1 are examples of labels that can be used for a different material classes corresponding to any tissue or vessels and/or equivalent tissue, respectively. Other labels and/or values may also be used.

Thus, some configurations of aspects of the invention can comprise a method that uses a 2D image dataset 106 together with additional information (e.g., calibration curves, part of anatomy relevant for treatment and/or surgery thickness, and/or x-ray technique) to determine a three-dimensional and/or four dimensional volumetric image of an imaged volume. A reconstructed volumetric image of an imaged volume is represented as a set of voxels with distinct values and/or labels (e.g., air/background, any tissue or vessel, tissue, and/or calcification) that satisfy and/or arbitrate among a set of constraints, for example, re-projection consistency with a 2D image dataset. More specifically, when determining a projection image from a three-dimensional N-ary reconstructed volume dataset (maybe after an appropriate mapping from labels to quantitative values), for one of a projection geometries as used for a data acquisition, a resulting re-projection image is constrained to be essentially identical to a corresponding projection image in an original 2D image dataset.

In some configurations, it is not necessary to input quantitative 2D image data to a reconstruction algorithm. Instead, in some configurations, it is sufficient to have a good estimate of a corresponding relative linear attenuation coefficients of a different tissue types as information used to develop a constraint set. In some configurations, algorithms for reconstruction as described herein and/or known is applied to a quantitative 2D image dataset at 120 and/or 122 as one and/or more steps for reconstruction according to an invention. This step and/or steps of one and/or more reconstruction algorithms can use any suitable known reconstruction algorithm(s) that accept a 2D image dataset as input and/or uses a dataset to reconstruct an estimate of a volumetric image of an object that produced a projection images. In some configurations of aspects of the invention, a projections are two-dimensional projections and/or a volumetric image reconstructions are three-dimensional and/or four-dimensional reconstructions of an imaged part of anatomy relevant for treatment and/or surgery. In some configurations of aspects of the invention, one step of a reconstruction algorithm does not produce a volumetric image that corresponds to Q(x,y,z) and/or B(x,y,z), per se, but rather, incremental changes to these volumetric images, updates ΔQ(x,y,z) and/or ΔB(x,y,z). Some reconstruction methods, for example, filtered back projection, require a preprocessing step (e.g., filtering) before a three-dimensional dataset (volumetric image) is formed. Through this preprocessing step some constraints of a quantitative projection images (or quantitative percentage estimate 118) may be violated, and/or it may be useful in some configurations of aspects of the invention to correct for this type of inconsistency before performing a final reconstruction step. For example, in a filtered back projection reconstruction method, each projection image is first high-pass filtered and/or then backprojected. A filtering step can potentially introduce very high and/or very small values (greater than 100% and/or smaller than 100% fat). Some configurations of aspects of the invention therefore round and/or threshold these outliers to a nearest admissible value to improve a volumetric image. In some configurations, a reconstructed volumetric image is constrained to an interior of a part of anatomy relevant for treatment and/or surgery.

The volumetric images produced by a reconstruction algorithm may be constrained more generally to produce a "constrained volumetric image". Common to all constrained volumetric images in aspects of the invention is at least one constraint that enforces an N-ary and/or approximately N-ary material class decomposition in B(x,y,z). A constraints used to produce a constrained volumetric image may also include 1) constraints on a shapes of structures of specific material classes within a volumetric image, B(x,y,z); 2) constraints on a number of voxels corresponding to a specific material class in a volumetric image; and/or 3) constraints on a connectedness of materials within a volumetric image, B(x,y,z). An example of connectedness is, for example, a six and/or twenty-six connectedness of a sets of voxels of a same material class in a volumetric image, B(x,y,z).

In some configurations, a reconstruction step simultaneously reconstructs interior structures of a part of anatomy relevant for treatment and/or surgery (i.e., its three-dimensional shape and/or location). In these configurations, additional information, such as a part of anatomy relevant for treatment and/or surgery edge (projected skinline) as detected in 2D image dataset 106, can be used in a reconstruction. In some configurations, this additional information is used in conjunction with smoothness constraints and/or other constraints. This simultaneous reconstruction of a geometry and/or a three-dimensional interior part of anatomy relevant for treatment and/or surgery structure lends itself to an iterative update, as described below, in which at each step, an anatomy feature geometry as well as a reconstruction of a part of anatomy relevant for treatment and/or surgery is improved.

Some configurations of aspects of the invention do not use a reconstruction constraint to map a quantitative volumetric image to an approximately N-ary volumetric image, i.e., a output volumetric image B(x,y,z) is a same as an input volumetric image Q(x,y,z).

In some configurations, an initial volumetric image 124 of an object is iteratively improved, by applying subsequent processing steps to an initial volumetric image 124. At any iteration, either no constraints at all and/or a plurality of constraints such as those described below are applied in some configurations. Some constraints can be more useful than others at specific points in a quantitative reconstruction. However, in configurations in which constraints are applied, a constraint and/or constraints comprise at least one constraint selected from those that follow, and/or may depend on an application sought to be accomplished and/or a specific step and/or iteration in a configuration.

One useful reconstruction constraint is a constraint in a volumetric extent of a volume defined by an air/tissue volumetric image. This constraint may be an integral part of a reconstruction step, and/or it may be used as a separate constraint. This constraint may be incorporated jointly with another reconstruction step, such as joint estimation of Q(x,y,z) and/or AT(x,y,z), and/or it may be performed as a "masking" operation, where, for instance, a reconstruction step constrains B(x,y,z) and/or Q(x,y,z) to be "0" except where AT(x,y,z) is "1".

Another useful constraint is to quantize in such a way that a "constrained volumetric image" is produced, e.g., such that a composition (i.e., material class membership of voxel values) of a volumetric image B(x,y,z) matches a total percent summary statistic obtained from a quantitative projections. Both a volumetric extent as well as a material class membership constraint are specific constraints that can be used separately and/or together to improve a reconstructed volume. In general, a number of constraints can be combined into a constraint set. Even a projection images that are used as input for a reconstruction step can be viewed as constraints. A specific form of a "constraint set" which produces a "constrained reconstruction" may be any information and/or processing which injects additional information in a process of reconstruction from projections.

Some configurations of aspects of the invention enforce constraints by modifying a first (intermediate) volumetric image (initial volumetric image and/or intermediate volumetric image, for example) that was previously computed without being subject to a set of constraints. However, in some configurations, these constraints are built directly into a reconstruction step. In other configurations, a number of subsequent steps in a reconstruction algorithm may impose constraints on a reconstructed volume, wherein each step may impose one and/or a combination of two and/or more constraints in a reconstructed volume, and/or different steps may include different sets of constraints. Also, each step may only improve a degree to which a set of constraints is satisfied, and/or not strictly impose that constraint. In some cases, a formal definition of a reconstruction energy can be used to arbitrate among conflicting constraints.

Elements of such constraint sets can include, but are not limited to: Quantization of voxel intensities in a 3D volumetric image, wherein a threshold is chosen.

Methods to choose a threshold include, but are not limited to (a), (b) and/or (c) below:

Determining a threshold using first principles of imaging physics (for example, attenuation coefficients). For example, a threshold is chosen halfway between a target quantization values. In some configurations, for an intensity value, x, between an expected intensities for each of a "fat" and/or "glandular" tissues, a voxel is set to "fat" if x is less than ½("fat"+"glandular"), and/or to "glandular" otherwise;

Determining a summary statistic from at least one projection image, and/or using these summary statistics, choosing a threshold that matches a same summary statistic of a 3D volumetric image. A summary statistic can be any metric, which for example may include, but are not be limited to, a total percent summary statistic and/or a gray level integral in an attenuation value domain. For example, if a global composition of an imaged part of anatomy relevant for treatment and/or surgery was determined to be 40% glandular, then a threshold for quantization is chosen such that 40% of a candidate "fat" and/or "glandular" voxels are quantized to glandular. A proper threshold can be determined, for example, from a histogram of voxel values in a (non-quantized) volumetric image Q(x,y,z). Using more than one constraint of a similar nature allows accurate adjustment of several quantization thresholds (e.g., threshold air/any tissue or vessel, and/or threshold any tissue or vessel/tissue).

Re-projecting a previously reconstructed 3D volumetric image Q(x,y,z) at all acquisition angles and/or choosing one threshold that best matches summary statistics between original 2D image dataset 102 and/or re-projections of a reconstructed 3D volume.

Morphological constraints, such as size and/or shape of connected regions of voxels, that may require a 3D structures in a N-ary volumetric image to resemble more closely a anatomical properties of a real part of anatomy relevant for treatment and/or surgery. These constraints may include, but are not limited to, (a) and/or (b): Relabeling (for an intermediate quantized B(x,y,z)) and/or adjusting voxel intensities (for a non-quantized Q(x,y,z)) where isolated pixels and/or small groups of pixels differ from their background volumes in some neighborhood. For example, a single isolated voxel of tissue is not expected within a larger volume that is all any tissue or vessel. Other anatomical prior knowledge can be used to allow and/or disallow certain structures within a reconstructed volumetric image.

Some reconstruction threshold choices and/or relabeling choices may make certain structures too large and/or too small. These structures can be altered in intensity, size and/or shape characteristics by standard volume processing techniques, e.g., using mathematical morphology.

Constrained volumetric image 130, B(x,y,z), can take on a number of different forms depending on a particular constraint set applied to a quantitative volumetric image at 128 that produced it. In one configuration, each voxel is assigned a label based on material classes chosen in a constraint set. For example, for tissues, air, fat, and/or labels, a form of a volumetric image can be an indexed set of three labels. In configurations in which a volume containing any tissue or vessel is constrained to a part of anatomy relevant for treatment and/or surgery, AT(x,y,z), a form of B(x,y,z) can be an indexed set of only two values, fat and/or glandular. If target tissue component or vessel and/or medical device or treatment are included in B(x,y,z), there can be two, three, and/or four labels. For example, in one labeling scheme, if B(x,y,z) is already constrained to exist in only a part of anatomy relevant for treatment and/or surgery, a form of B(x,y,z) may comprise labels for only soft tissue (fat and/or glandular) and/or target tissue component or vessel and/or medical device or treatment. In other configurations, specific soft tissue distinctions are also designated within a part of anatomy relevant for treatment and/or surgery using labels that designate fat, glandular, and/or target tissue component or vessel and/or medical device or treatment. Some configurations use only labels, exclusively. For example, air, fat, and/or target tissue component or vessel and/or medical device or treatment labels are used in a single B(x,y,z) in some configurations. In some configurations, as an alternative to labels, specific distinct numerical values can be used to indicate constituent components of an imaged volume (e.g., one can use linear attenuation coefficients associated with a different tissue types for some fixed x-ray and/or radiation spectrum as indicators).

In some configurations, a constrained volumetric image 130, B(x,y,z), is a numerical mapping from Q(x,y,z) which produces a "fuzzy" numerical label associated with each tissue type. Such a "fuzzy" labeling allows intermediate tissue labeling in a volumetric image, which can capture partial volume effects, for example. In such a mapping, instead of forcing each voxel to take on one of a set of specific labels (or numerical values) associated with particular material classes, this constraint is relaxed and/or B(x,y,z) takes on voxel intensity values that are allowed to move "closer" to a numerical labels based on image properties. In this way, a voxel intensities in Q(x,y,z) are remapped to a scale related to a labels as described in (1) immediately above, but are actually another set of intensities. Thus, a voxel-values in B(x,y,z) do not correspond to a set of discrete labels, but rather a continuous-valued set of intensity values. For example, in some embodiments, a sets of intervals ((air, air+$\Delta_a$), (fat-$\Delta_f$, fat+$\Delta_f$), (glandular-$\Delta_g$, glandular+$\Delta_g$), (calc-$\Delta_c$, calc+$\Delta_c$)), define a allowable material classes in B(x,y,z). A value in Q(x,y,z) that lies between "fat+$\Delta_f$" and/or "glandular-$\Delta_g$" is rounded to a value either between "fat" and/or "fat+$\Delta_f$" and/or between "glandular" and/or "glandular-$\Delta_g$", depending on a material class constraints. A different value in Q(x,y,z) that lies between "fat-$\Delta_f$" and/or "fat+$\Delta_f$" might remain unchanged, depending on a material class constraints. Thus, mappings need not specifically map a numerical intensity value in Q to a label in B, but can be more broadly defined as a result of applying a material class constraints to Q.

Figure 7:
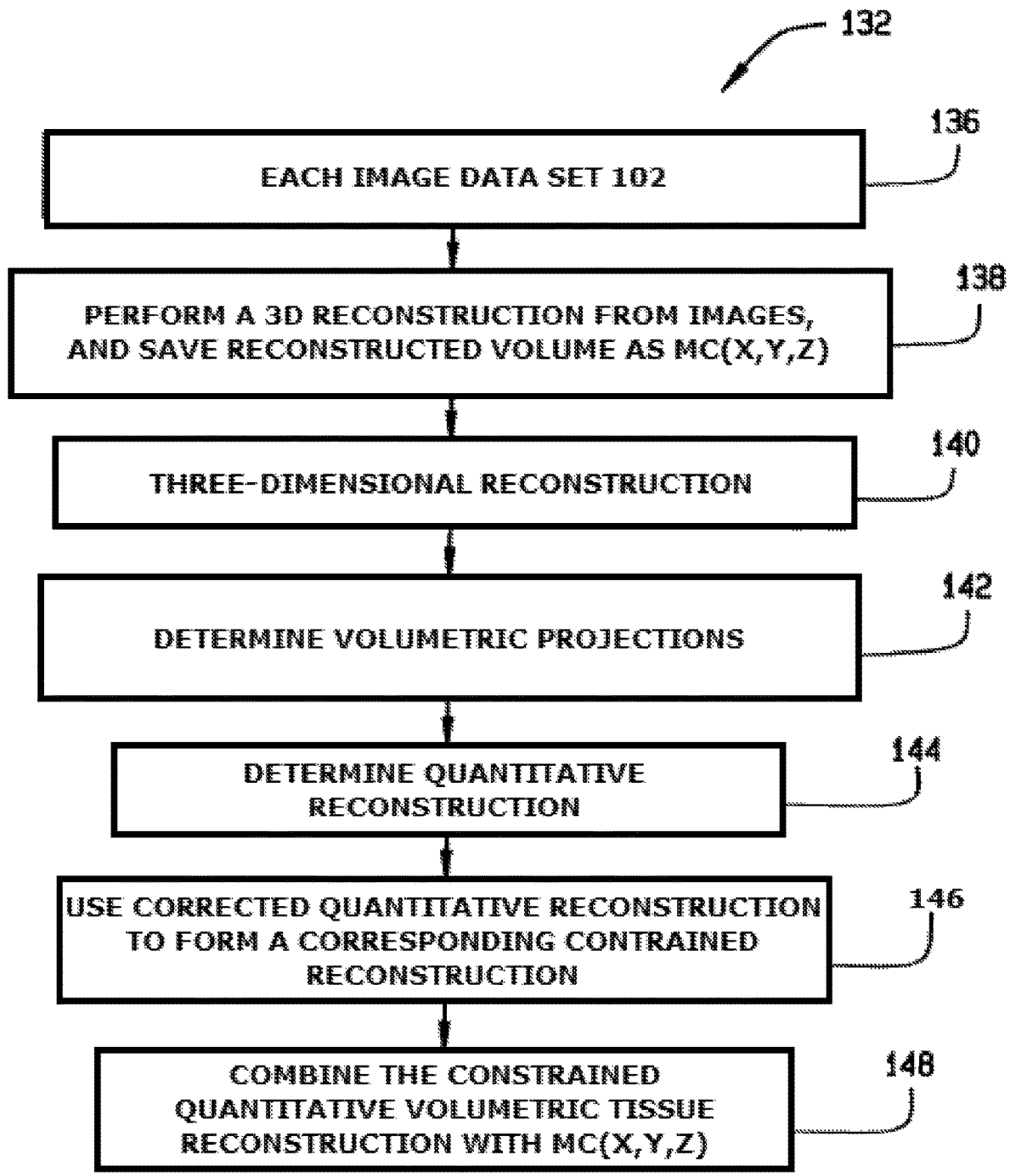
FIG. 7 is a flowchart illustrating a configuration of aspects of the invention useful for quantitative tissue reconstructions.

Because target tissue component or vessel and/or medical device or treatment represent exceptions to a two material class tissue composition model, where a two material classes are fat and/or tissue, e.g., in some configurations, they are processed separately, using known image processing techniques to detect target tissue component or vessel and/or medical device or treatment in a projection image dataset with a high degree of reliability. Once target tissue component or vessel and/or medical device or treatment are detected, they can be excluded from a reconstruction procedure and/or a subsequent quantization step and/or reconstructed separately. Three-dimensional tissue, medical device or treatment, information can then be inserted into a constrained reconstruction to recover a full quantitative volumetric image of an imaged part of anatomy relevant for treatment and/or surgery, as well as corresponding medical device/treatment. In some configurations and/or referring to FIG. 7, a separate processing of calcifications at 132 includes a following steps:

At 136, find and/or detect target tissue component or vessel and/or medical device or treatment in each image of 2D image dataset 102 (or quantitative percentage estimate 118).

At 138, perform a 3D reconstruction from a target tissue component or vessel and/or medical device or treatment detection images, and/or save this volumetric image as MC(x,y,z). MC has essentially a zero mean background and/or signal only at a locations of a target tissue component or vessel and/or medical device or treatment.

At 140, find individual target tissue component or vessel and/or medical device or treatment in a 3D volumetric image (i.e., in MC(x,y,z)).

At 142, determine locations at which a target tissue component or vessel and/or medical device or treatment in a volumetric image, MC(x,y,z), manifested themselves in projections (e.g., by re-projecting a 3D volumetric image MC(x,y,z)).

At 144, determine a target tissue component or vessel and/or medical device or treatment corrected quantitative volumetric image Q(x,y,z), e.g., by using one of a following methods (a) (b) and/or (c).

In determining a quantitative volumetric image 124 of a part of anatomy relevant for treatment and/or surgery, Q(x,y,z), at (x,y,z) coordinates that correspond to a location of target tissue component or vessel and/or medical device or treatment in at least one of a projection images, use only that subset of a quantitative projection radiographs, $q_i(u,v)$, that contain no target tissue component or vessel and/or medical device or treatment that would project to that particular (x,y,z) coordinate. Thus, in one step of a reconstruction algorithm, a projection radiographs that contain a target tissue component or vessel and/or medical device or treatment at (u,v) locations that map to a (x,y,z) location being reconstructed are disregarded.

Values in quantitative projection radiographs, $q_i(u,v)$, at (u,v) locations that coincide with a projected location of a target tissue component or vessel and/or medical device or treatment are replaced by an appropriate "calcification corrected" estimate based on neighboring pixel values, and/or a resulting adjusted $q_i(u,v)$ images are used as input for a quantitative reconstruction.

a size and/or x-ray attenuation characteristics of a reconstructed 3D calcifications (found in MC(x,y,z)) are used to correct a corresponding pixel values in a quantitative projection radiographs, $q_i(u,v)$, by "removing" a estimated contribution of a calcifications to a observed images, based on imaging physics. Again, a resulting images are used as input for a quantitative reconstruction. A result of this step is a target tissue component or vessel and/or medical device or treatment corrected quantitative 3D volume Q(x,y,z).

At 146, use a "corrected" target tissue component or vessel and/or medical device or treatment corrected quantitative volumetric image Q(x,y,z) to form a corresponding "constrained volumetric image", B(x,y,z).

At 148, to a constrained quantitative volumetric tissue image, B(x,y,z), combine MC(x,y,z) in an appropriate way.

In some configurations, a resulting volumetric image, B(x,y,z) (or Q(x,y,z)) is iteratively updated at 124 to enforce consistency with an input data, and/or other additional information and/or constraints. For example, a reconstructed volumetric image is re-projected, a re-projected images are compared with a original projection images, and/or a volumetric image is updated so that a deviation between original 2D image dataset and/or a re-projected dataset becomes smaller. This step can be repeated to achieve convergence to a solution that satisfies a re-projection consistency constraint. Furthermore, this iteration may include one and/or more separate steps to update a part of anatomy relevant for treatment and/or surgery, a quantitative volumetric image within a part of anatomy relevant for treatment and/or surgery, Q(x,y,z), and/or a constrained quantitative volumetric image, B(x,y,z), each separately and/or together. Some configurations perform a plurality of these improvement steps at each iteration step. In some configurations, an image used as input to a reconstruction process are updated at each step such that a reconstructed volumetric image based on an updated images is an "improved" volumetric image.

Enforcing consistency between a reconstructed volumetric image (either Q and/or B) and/or a acquired projection images may require a "re-projection" step in which a reconstructed volumetric image is used to produce one and/or more projection images. A reconstructed volumetric image is re-projected in some configurations so that a re-projections are directly comparable to an acquired projection images. A re-projection can be generalized into one that transforms a labeled volumetric image into one and/or more re-projections having pixel intensities that are continuous-valued so that they are comparable to a qi(u,v) projection radiograph dataset.

Determining an error signal for a consistency constraint may be as simple as subtracting images in a 2D image dataset from a set of re-projections on a pixelwise basis. However, other methods for determining an error signal for a set of acquired projections and/or re-projections can be used. A acquired projections are q (u,v). A re-projections at iteration j are $r_i(u,v))^{(j)}$ and/or $b_i(u,v)^{(j)}$. An error signal may be some function of a 2D image dataset (or some processed version thereof), as well as all a re-projections at every prior and/or current iteration. That is, a error signal can be:

$$\Xi_j = \Psi(\Xi_0(q(u,v)), \Xi_1(r_1(u,v)), \Xi_2(r_2(u,v)), \ldots, \Xi_j(r_j(u,v)), \Xi_{j+1}(b_1(u,v)), \Xi_{j+2}(b_2(u,v)), \ldots, \Xi_{2j}(b_j(u,v)))$$

For example, a $\Xi_i$ functions can be used to compute an error at specific regions of a projections and/or weight a errors at specified regions in a projection domain. This is useful because some regions of a re-projections and/or a quantitative projection radiographs themselves may contain differences that are irrelevant to a output volumetric image, B(x,y,z), 130 in FIG. 6, for example. A error function, $\Psi$, takes as inputs two sets of images in a projection domain and/or can be a difference of an image sets and/or a difference with a saturating non-linearity and/or some other nonlinear operation on an image sets. In general, $\Psi$ and/or $\Xi_i$ are functions that can depend on local neighborhoods of pixel intensities and/or global properties of a volumetric image, an acquired projections, and/or a re-projections.

In some configurations, determining a volumetric update to a volumetric image comprises reconstructing a volumetric image that corresponds to a difference between re-projected images and/or a original 2D image dataset 102, and/or adding this "volumetric update image" to a previously determined volumetric image, B(x,y,z) and/or Q(x,y,z), using an appropriate weighting. However, other combinations of reconstructed volumetric images and/or volumetric update images to volumetric images can be used. For example, some configurations combine a reconstructed volumetric image from a previous iteration and/or a "volumetric update image" using a nonlinear transformation. Such a nonlinear transformation can include multiplicative transformations, logarithmic transformations, saturating nonlinearities, and/or other transformations and/or nonlinear look up tables. Such a nonlinear transformation can be applied to either a previous iteration's volumetric image, a volumetric update image, both, and/or a combination, itself, can be remapped nonlinearly. A combination can include spatial filtration, wherein volumetric image voxel intensities are adjusted in accordance with local neighborhood and/or global reconstructed volumetric image properties.

In some configurations, and/or referring to FIG. 8, a variant of an algebraic reconstruction technique (ART) 150 can optionally be used for iterative updates. A technical effect of apparatus 10 (or of other configurations of aspects of the invention) is achieved by a user operating apparatus 10 to perform an initial reconstruction as indicated at 152, 154, 156, 158, and/or 160, from data set 102 (or quantitative percentage estimate 118). A result is constrained at 154 and/or 158 in some, but not all configurations. A volumetric image is re-projected at 164 and/or 166. An error is determined at 162 and/or 158 between re-projection 166 and/or original dataset 102 and/or 118. This error may be determined for one and/or more of a projection images. Some configurations apply an appropriate constraint set at 170 specific to this step and/or iteration. A volumetric update image 176 is reconstructed at 172 using an error signals. Volumetric correction image 176 is constrained at 174 with some constraint set specific to this step and/or iteration in some configurations. At 178, a volumetric correction image 176 is combined with a volumetric image 156 and/or 160 from a previous iteration. A existing volumetric image may be either a quantitative volumetric image, Q(x,y,z), 156 and/or a constrained volumetric image, B(x,y,z) 160. This combination is constrained at 180 in some configurations using a constraint set specific to this step and/or iteration. An iteration is stopped or, if necessary, another iteration is performed by continuing at step 164. A constraints that are utilized in this approach, can be appropriately chosen from a plurality of constraints explained above.

In some configurations of aspects of the invention, appropriate energy functional (or energy functions and/or energy terms) will assume a minimum for a volumetric images, B(x,y,z), that simultaneously satisfy, and/or arbitrate among, a number of simultaneous constraints. Typically each constraint in a considered constraint set corresponds to a specific term in an energy functional. This energy minimization interpretation leads to strategies and/or algorithms for volumetric image reconstruction that are fundamentally different from a reconstruction algorithm as described up to this point in aspects of the invention. In an implementation-specific approach (as it is described up to this point), where reconstruction steps are designed to satisfy individual constraints one (or few) at a time, variable means can be used to devise reconstruction algorithms consisting of steps that simultaneously satisfy and/or arbitrate among a many constraints desirable in a output volumetric image. Adjustments are made to avoid where one reconstruction step can undo and/or corrupt a desirable property from a previous step of a reconstruction algorithm. In configurations of aspects of the invention in which an energy functional is used to reconstruct a volumetric image, a reconstruction algorithm comprises a number of reconstruction steps (for example, iterations), where generally each step decreases a value of an energy functional by modifying a current estimate of a reconstructed volumetric image. In some configurations of aspects of the invention, optimization methods (coordinate descent, gradient descent, Newton's method, coordinate wise minimization, etc.) are used to find a volumetric image that best either simultaneously satisfies and/or arbitrates among a multiple constraints corresponding to terms of an energy functional. In other configurations, other strategies may be used, where a value of an energy functional does not necessarily decrease in each update step. This may be useful in situations where an energy functional has local minima.

In some configurations of aspects of the invention, and/or referring to flowchart 182 of FIG. 9, a technical effect of apparatus 10 (or another configuration of aspects of the invention) is achieved by a user operating an apparatus to reconstruct a volumetric image of an object, initially by acquiring projections pi(u,v) of an object at 184. In some configurations, projections pi(u,v) are preprocessed at 186 so that they are quantitative projections. A preprocessing may contain such steps as bad pixel correction, gain correction, scatter correction, and/or a correction to remap intensities to reflect a quantitative measure of composition, for example by making an intensities true line integrals free from corrupting physical effects. An initial reconstruction is performed at 187. Initial reconstruction 187 is performed in some configurations by computing Q(x,y,z) and/or B(x,y,z) from qi(u,v). From this Q(x,y,z) and/or B(x,y,z), an appropriate energy to minimize as well as parameters for a minimization may be chosen. An energy definition is chosen at 188 either (a) automatically in accordance with image information, (b) as a default energy, which may depend upon x-ray technique and/or part of anatomy relevant for treatment and/or surgery thickness and/or other similar physical parameters, and/or (c) by interaction with a user, such as by interactively choosing from a list of default energies, and/or (d) a combination of (a), (b), and/or (c). A energy definition at 188 includes at least one term that constrains a reconstructed volumetric image to a material class volumetric image, B(x,y,z), for example, such that every voxel in a material class volumetric image contains only one value (or label) corresponding to a single material class each. Parameters associated with an energy definition selection may also be chosen from an initial volumetric image Q(x,y,z) and/or B(x,y,z). An N-ary reconstruction is performed at 190 by estimating a volumetric image, B(x,y,z), that produces a smallest value of a reconstruction energy functional. This reconstruction can be performed using (a) optimization methods (b) energy computations over a random search of volumetric images, B(x,y,z), and/or (c) exhaustive search (which will produce an absolute minimum of an energy functional and/or an optimal volumetric image for an energy).

In one configuration of aspects of the invention, an energy functional contains a term which increases in value as a voxel intensities in a constrained volumetric image, B(x,y,z), differ from voxel intensities corresponding to a material classes in a hypothesized model of a part of anatomy relevant for treatment and/or surgery. In this case, an energy functional contains an N-ary material class enforcement term such that a value of a N-ary material class enforcement term is minimal when B(x,y,z) contains only a material classes in a hypothesized model of a part of anatomy relevant for treatment and/or surgery (e.g. A term achieves its minimum value when B(x,y,z) contains only labels that correspond exactly to one of a plurality of material class labels and/or B(x,y,z) contains only values that are elements of a material classes—for instance, a two material model may consist of a voxelwise and/or tissue material class labeling). An energy minimizing reconstruction algorithm 190 configured to enforce an N-ary, and/or approximately N-ary, material class volumetric image reconstruction will select a volumetric image, B(x,y,z), that, among candidate volumetric images, minimizes a reconstruction energy functional. That is, a output volumetric image, B(x,y,z), is an N-ary volumetric image. (In some configurations, a minor, but not necessarily preselected portion of a reconstructed volumetric image is permitted to correspond to one and/or a small number of other types of tissues.) Any necessary post-processing steps can be performed at 192, including iterating a reconstruction of steps 186, 188, and/or 190.

In some configurations of aspects of the invention, a difference between a % Gi estimates from a plurality of projection images qi(u,v) and/or reprojection images ri(u,v) from B(x,y,z) and/or some nominal % G for a volumetric image, B(x,y,z), is included in an energy functional to produce % G-consistent volumetric images from a projection dataset. Such a constraint may be incorporated into an energy functional as GC(B), where GC(B) is smallest where a % Gi estimates are aggregately closest to some nominal % G and/or representative % G, and/or where GC(B) is larger as a estimates of percent vary from a nominal estimate and/or amongst themselves. In some configurations a % G value for a current estimate of a volumetric image of an object is determined directly from B(x,y,z) (or Q(x,y,z)) without computing a corresponding re-projected images.

Energy functional minimization approaches have been considered for a wide array of multidimensional processing and/or information extraction tasks, including edge-preserving smoothing volumetric reconstruction, general image restoration, image in-painting, curve evolution, and/or segmentation, among others. These individual applications each have specific energy formulations which define a properties of a resulting processed fields (any image and/or 3D volumetric image, e.g., is a field). Many known energy definitions are intended for processing of observations which are already reconstructed data (slices, images, and/or full 3D volumetric images). These energies, although not image reconstruction energies specifically, are important because they can be tied into an overall conglomerate energy, as defined below. Specific energy definitions with more and/or less limited scope of application are known and/or have been proposed for a number of different reasons, and/or include a number of different terms with different properties. By contrast, some configurations of aspects of the invention consolidate these terms into an overall conglomerate energy functional that has properties that are a function of all such terms, and/or at least of a plurality of specific energy definitions. For example, reconstruction algorithms previously have not been derived from material class decomposition constraints. Generally reconstruction algorithms have not been derived from an energy which contained at least one term that enforced an "N-ary" decomposition of an imaged volume—that is, a minimizer of an energy functional is an "N-ary" volumetric image.

A straightforward energy minimization approach to solving an image reconstruction problems is a least squares solution. In this case, a squared error between projections of a volumetric image and/or a observed projection is minimized. This approach is often referred to as solving an unregularized "inverse problem" where an effect of "projecting" an imaged object is "inverted." This may also be referred to as minimizing a quadratic fidelity term (which represents an energy functional, and/or a term in a more complex energy functional). Although a closed form solution in a least squares sense can be achieved, unregularized solutions to inverse problems often suffer numerical instabilities (high condition number). In most volumetric imaging problems, especially limited angle image reconstruction problems, an unregularized solution (a volumetric image, for example) is (mathematically) not uniquely determined, which can lead to high spatial frequency artifacts. To mitigate numerical stability issues associated with a simple least squares energy, a side constraint can be added to an energy. This side constraint is termed a "regularizer". In most energy minimization methods for volumetric image reconstruction, suitable side constraints are determined so that a reconstruction enjoys desirable properties. Tikhonov proposed side constraints which were quadratic penalties on an actual values of a reconstructed field (A. N. Tikhonov, V. Y. Arsenin, "Solutions of Ill-posed Problems," Wiley, New York, 1977). Note that energy formulations of a reconstruction problem may lead to identical solutions to reconstruction algorithms already proposed. A Tikhonov energy definition above, for example, is minimized by a volumetric image produced by iterating an additive ART algorithm to convergence. For some applications, it is more appropriate to add a quadratic penalty on a derivative of a reconstructed field because although little may be known about an actual values a reconstructed field should take on, it may be known that a field should be smooth. (A. N. Tikhonov, V. Y. Arsenin, "Solutions of Ill-posed Problems," Wiley, New York, 1977) (all and each of the above entirely incorporated herein by reference).

Such approaches can be of limited value, however, because a quadratic penalty on a derivative rapidly removes edges from solutions (volumetric images, for example) (edge oversmoothing), which are often important sources of information in imagery. To mitigate a edge oversmoothing problem, Osher and/or Rudin proposed a Total Variation energy (S. Osher and/or L. Rudin, "Feature-oriented image enhancement using shock filters." SLAM journal of Numerical Analysis, 27(4):919-940, August, 1990), which is a sum of a quadratic fidelity term and/or a sum of absolute values of a derivative function (e.g., adjacent pixel/voxel differences). Total variation solutions often compare favorably to reconstructions where Tikhonov derivative side constraints are used. Still some investigators have gone further. Specifically, to smooth regions and/or still allow a formation of edges, a Mumford Shah energy functional includes an explicit estimate of a boundaries between regions (D. Mumford, J. Shah, "Boundary detection by minimizing functionals, I." In Proc. of an iEEE Conf. On Computer Vision and/or Pattern Recognition, pages 22-26, 1985) (All and each of the above entirely incorporated herein by reference).

Using this information, a Tikhonov derivative side constraint and/or a Total Variation energy can be minimized where a derivative penalty is relaxed where an edge is indicated by an auxiliary boundary field. Such approaches suffer numerical issues in their solution because a minimization requires a joint estimation of a reconstructed volumetric image (3D and/or 2D field, e.g.) and/or a segmenting curve (2D surface and/or ID curve, e.g.). To alleviate those numerical issues, other investigators reformulated a binary nature of a segmenting curve to be an auxiliary edge field (instead of a curve in space) (L. Ambrosio, V. M. Tortorelli, "On an approximation of free discontinuity problems," Bollettino Della Unione Matematican italiana, 6-B:105-123, 1992). This reformulation allowed faster solution methods such as coordinate descent on a joint set of fields. Other approaches to minimizing a variant of a Mumford Shah functional enforce a constraint of estimating a closed curve, which permits a use of fast numerical methods, such as level set methods, for a solution method (A. Tsai, A. Yezzi, A. S. Willsky, "Curve Evolution Implementation of a Mumford-Shah Functional for Image Segmentation, Denoising, Interpolation, and/or Magnification," IEEE Trans. On Image Proc., Vol 10, No. 8, August 2001). In addition to penalties on a spatial derivative of a reconstructed values, a reconstructed values may themselves be constrained to have a specific intensity distribution. For instance, values of a reconstructed volumetric image may be constrained to be samples of an intensity distribution defined by a Gaussian mixture model (W. M. Wells, W. E. L. Grimson, R Kikinis, "Adaptive Segmentation of MRI data." IEEE Trans. On Med. Imag., 15(4):429-442, August 1996). Still other energies incorporate terms which depend on a shapes of structures and/or their registration with corresponding images from other modalities and/or from a same modality with different acquisition parameters (T. F. Cootes, C. Beeston, G. J. Edwards, C. J. Taylor, "A Unified Framework for atlas matching using active appearance models" in A. Kuba, M. Smal, and/or A. Todd-Pokropek, editors, Lecture Notes in Computer Science 1613: Information Processing in Medical Imaging, volume 1613, pages 322-333. Springer Verlag, 1999). Such energies include terms which depend on relative locations of structures, an intensity dependence on relative location, and/or an expected curvature (or other shape/morphology descriptor) in different anatomical regions (all and each of the above entirely incorporated herein by reference).

Once an energy is defined, a reconstruction method can be considered as an optimization problem. There are well-known published methods for optimizing (finding minimizers of) energy functionals. These commonly include Newton and/or quasi-Newton methods which implement Hessian updates at each iteration of a minimization process. Davidon-Fletcher-Powell (DFP) and/or Broyden-Fletcher-Goldfarb-Shanno (BFGS) methods, among others, can be used in such a scenario. For energies which have as components, penalties which are absolute values of fields and/or auxiliary fields, parts of solution methods may be formed from linear programming approaches, such as simplex methods and/or Karmarkar's methods, e.g. A host of minimization approaches, such as coordinate descent, gradient descent, simulated annealing, among many other published and/or well-studied minimization and/or optimization methods, may be used for a minimization of any given energy.

Specifically, gradient descent methods update a plurality of independent variables in an energy at each step. A gradient descent method requires 1) an estimate of a local gradient of an energy functional computed at a current estimate of a field and/or 2) a line search in a direction of greatest descent of an energy gradient. To address a first requirement, a gradient of an energy at a given estimate of a field must be estimated; this can be accomplished using an analytic expression for a continuous and/or discrete version of a gradient of an energy, itself (Y. Saad, "Iterative Methods for Sparse Linear Systems." a PWS Series in Computer Science. PWS Publishing Company, a division of International Thomson Publishing, Inc., PWS Publishing Co. Boston, Mass., 1996), by numerically estimating a gradient from a observations (Matlab Optimization Toolbox Manual, http://www.mathworks.com/products/optimization/), and/or using stochastic methods (Viola, P. A., "Alignment by Maximization of Mutual Information", MIT AI Technical Report No. 1548, June, 1995). There are a host of line search algorithms in a published literature to address a second requirement. These line-search algorithms include linear searches, logarithmically spaced searches, and/or constant step size searches (W. H. Press, B. P. Flannery, S. A. Teukolsky, W. T. Vetterling, Numerical Recipes, Cambridge Univ. Press, Cambridge, UK (1986)) (all and each of the above entirely incorporated herein by reference).

Because a Tikhonov regularization energy is quadratic, its minimization in a reconstruction is linear. Thus, a Tikhonov regularized reconstruction can be solved using a linear equation solver, such as direct inversion, standard and/or preconditioned conjugate gradient, multigrid methods, and/or Monte Carlo methods. We will group these methods under an umbrella term, linear equation solvers. (A. N. Tikhonov, "Regularization of incorrectly posed problems," Soviet Math. Dokl, vol. 4, pp. 1035-1038, 1963) (All and each of the above entirely incorporated herein by reference).

The heat equation (as one example of an energy minimization problem) can be solved by convolving a observed field with a gaussian distribution of unit mass whose variance is proportional to a time a field's temperature has been "flowing". It is conceivable that convolution with some other kernel which is different from a gaussian distribution would lead to a solution to some other minimization problem. We will group all solution methods which can be solved by convolution under an umbrella term, convolution methods (Koenderink, J, a structure of images. Biol. Cybern. 50, 363-370, 1984) (all and each of the above entirely incorporated herein by reference).

Total variation-type energies, including Vogel's and/or Cetin's, can be minimized using half quadratic minimization and/or gradient descent techniques together (C. R. Vogel and/or M. E. Oman, "Fast, robust total variation-based reconstruction of noisy, blurred images," IEEE Trans. On Image Processing, vol. 7 no. 6, pp. 813-824, June 1998, "Feature-enhanced synthetic aperture radar image formation based on nonquadratic regularization," Müjdat Cetin and/or W. Clem Karl, IEEE Trans. Image Processing, vol. 10, no. 4, pp. 623-631, April 2001) (All and each of the above entirely incorporated herein by reference) The Wells EM adaptive segmentation energy, which includes terms that minimize an effect of a slowly varying additive field (the bias field) and/or terms that penalize a deviation in intensity value from a given intensity model distribution can be solved by interpreting an energy as proportional to a log likelihood function of a underlying probabilistic model for a field and/or then using expectation maximization methods to compute a maximum likelihood estimate of that field (Adaptive segmentation of MRI data. Wells W M, Kikinis R, Grimson W E L, Jolesz F. IEEE Transactions on Medical Imaging. 1996; 15:429-442) (all and each of the above entirely incorporated herein by reference).

Energies akin to Shah's and/or Yezzi's, which may include an explicit boundary term as an auxiliary field, can be minimized using modified level set methods as described by Sethian. (A. Tsai, A. Yezzi, and/or A. Willsky, "A curve evolution approach to smoothing and/or segmentation using a Mumford-Shah functional," Proc. IEEE Conf. On Computer Vision and/or Pattern Recognition, June 2000, T. Chan and/or L. Vese, "A level set algorithm for minimizing a Mumford-Shah functional in image processing," UCLA Technical Report, 2000) (All and each of the above entirely incorporated herein by reference).

In this approach, an edge strength function is minimized with respect to a reconstruction, and/or then fixing a reconstruction is minimized with respect to an edge strength function. In each step of a coordinate descent, a linear equation solver is used. (Energy Formulations of Medical Image Segmentations, Ph.D. Thesis, J. Kaufhold, Boston University College of Engineering, Aug. 11, 2000) (All and each of the above entirely incorporated herein by reference).

In other iterative approaches, an energy functional is not explicitly formulated, but a reconstructed volumetric image is assumed to be subject to certain additional constraints (which can alternatively also be formulated as explicit terms in an energy functional) Examples of these approaches include additive ART, and/or multiplicative ART (MART) (Verhoeven, D., Limited-Data Computed Tomography Algorithms for a Physical Sciences, Appl. Optics, vol. 32, no. 20, July 1993), which both aim at satisfying a re-projection constraint (i.e., they minimize a least squares fidelity term). These iterative methods can be combined with additional constraints, for example by alternating an ART iteration step with an additional update step that modifies a current estimate of a reconstructed volumetric image such that it satisfies an additional constraints. A similar type of approach can be used with other reconstruction methods, like Fourier based reconstruction (B. Claus, M. Yavuz, B. Opsahl-Ong, A Fourier Based Method for Optimal Reconstruction in Digital Tomosynthesis, GE GRC disclosure RD-27853, December 1999, patent filed June 2003), Matrix Inversion Tomosynthesis (MITS—Dobbins III, J. T., Matrix Inversion Tomosynthesis Improvements in Longitudinal X-Ray Slice Imaging, U.S. Pat. No. 4,903,204, filed December 1987), Direct ART (DART—B. Claus, A Non-Iterative Algebraic Reconstruction Technique for Tomosynthesis, GE GRC disclosure RD-30968, August 2002, patent filed September 2003), Generalized Filtered Back projection (GFBP—in Claus BEH, Eberhard J W, Thomas J A, Galbo C E, Pakenas W P, Muller S: Preference Study of Reconstructed Image Quality in Mammographic Tomosynthesis, IWDM 2002—Proc. 6$^{th}$ Intl. Workshop on Digital Mammography, Bremen, Germany, 2002, Springer 2003, also B. Claus, J. Eberhard, Generalized Filtered Back projection Reconstruction in Digital Tomosynthesis, GE GRC disclosure RD-29603, August 2001, patent filed April 2002), Filtered Back projection (FBP—Yavus, M., Edic, P. M., Ishaque, A., N., Patch, S. K., Method and/or Apparatus for Reconstructing Image data Acquired by a Tomosynthesis X-Ray Imaging System, U.S. Pat. No. 6,292,530 B1, Sep. 18, 2001) etc. by alternatingly applying steps of reconstruction, applying constraints to reconstructed volumetric image, re-projection and/or reconstruction of differences and/or update of reconstructed volumetric image (all and each of the above entirely incorporated herein by reference).

In known methods for a minimization of an energy functional and/or a representation of a data that is utilized in an implementation, a minimization is not worked on a continuous field, but rather on a discrete grid of points. More specifically, a field is defined on a regular lattice and/or computations are performed using values defined on a lattice. However, for discussion, it is often easier to illustrate similarities to prior art in a context of a continuous rather than a discrete formulation of a reconstruction energy.

A remote collaborative diagnosis method and system using a cloud, internet, and/or browser, application, or server based medical image sharing scheme according to an embodiment of the present invention will be described in detail below with reference to FIGS. 12-19.

Figure 12:
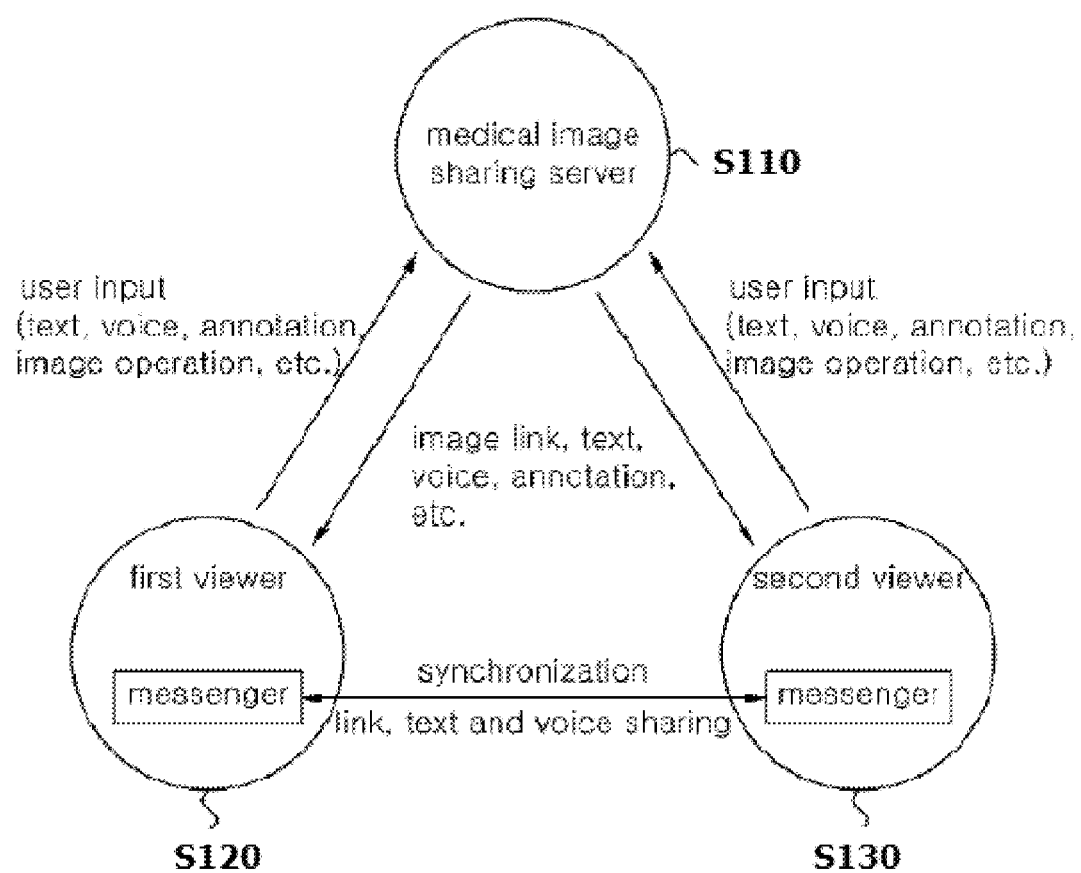
FIG. 12 is a diagram illustrating the configuration of a cloud, internet, and/or browser, application, or server based medical image sharing system according to an embodiment of the present invention.

FIG. 12 is a diagram illustrating the configuration of a cloud, internet, and/or browser, application, or server based medical image sharing and 3D/4D rendering system according to an embodiment of the present invention.

Referring to FIG. 12, the system according to the present invention optionally includes a medical image sharing and 3D/4D rendering browser, application, or server S110, a first user S120, and a second user S130. In the following detailed description of the present invention, for ease of description, the first user S120 is assumed to be the user of a user who requests medical image sharing and 3D/4D rendering (hereinafter referred to as the "first user"), and the second user S130 is assumed to be the user of a user who is connected to or selected by the user of the first user S120 (hereinafter referred to as the "second user").

The first user S120 optionally includes a messenger to communicate with the messenger of the second user S130 in order to make a collaborative diagnosis. The first user S120 requests and receives a medical image from the medical image sharing and 3D/4D rendering browser, application, or server S110, displays the medical image on a screen, selects a second user with whom the medical image will be shared when the medical image is to be shared in response to a request from the first user, and optionally provides information about a link to the medical image to be shared to the messenger of the second user S130 via its own messenger.

In this case, the first user of the first user S120 can receive information about a plurality of users from the medical image sharing and 3D/4D rendering browser, application, or server S110 and then select the second user based on the received information about a plurality of users. Alternatively, the first user of the first user S120 can select the second user from among the users of other messengers connected to its own messenger.

Furthermore, the first user can acquire information about a user group preset by the first user and then select the second user from among users included in the acquired information about the user group. In this case, the information about the user group can be stored in the first user S120, or can be stored in the medical image sharing and 3D/4D rendering browser, application, or server S110 and provided to the first user S120 in response to a request from the first user.

In this case, the first user can add, delete and change users included in the information about the user group using an interface provided in the first user S120 or messenger. The information about the user group set by the first user information about a basic group to which the first user belongs to, or information about a first group related to another department to which the first user does not belong. It will be apparent that the first user can select one of the information about a basic group and the information about a first group using the interface provided in the first user or messenger.

In this case, the first user S120 can perform a synchronization process required to share the medical image with the second user S130. Once the first user S120 has been synchronized with the second user S130, the first user S120 can provide the information about the link to the medical image to be shared (hereinafter referred to as the "sharing-target medical image") to the messenger of the second user S130, and can later share a sharing-target medical image in which a user operation input by the first or second user has been processed, text, voice, etc. via the medical image sharing and 3D/4D rendering browser, application, or server S110. It will be apparent that in some cases, information about links to a user operation, text, voice, etc. can be transmitted and received via the messengers and thus a sharing-target medical image in which a user operation input by the first or second user has been processed, text, voice, etc. can be shared.

In this case, the synchronization between the first and second users S120 and S130 can be synchronization between the messenger of the first user S120 and the messenger of the second user S130, or can be synchronization achieved via the medical image sharing and 3D/4D rendering browser, application, or server S110.

In the present invention, the first and second users S120 and S130 are described as receiving processing results attributable to the input of the first or second user, for example, a sharing-target medical image in which rotation, expansion, reduction or rendering has been processed in response to the image operation of a user, CAD results, an annotation, text, voice or the like, directly from the medical image sharing and 3D/4D rendering browser, application, or server S110.

It will be apparent that the first and second users S120 and S130 do not necessarily receive processing results attributable to user input directly from the medical image sharing and 3D/4D rendering browser, application, or server S110, but can receive information about a link to processing results from the medical image sharing and 3D/4D rendering browser, application, or server S110 and then receive the processed results via the information about a link.

When a user operation, an annotation, text, voice or like is input after the first user S120 has been synchronized with the second user S130, the first user S120 can provide the input information to the medical image sharing and 3D/4D rendering browser, application, or server S110, the medical image sharing and 3D/4D rendering browser, application, or server S110 optionally provides information about a related link to the two users, and thus the two users can share results attributable to the user input of any one user, thereby minimizing traffic between the two users.

It will be apparent that information about a link to results attributable to user input can be transmitted and received between the two users via the messengers. In this case, a user via which user input has been performed can receive information about a link to results attributable to the user input from the medical image sharing and 3D/4D rendering browser, application, or server S110, and can provide the information about a link to the other user.

That is, although the information about a link used in the detailed description of the invention can be generated by a user and transferred to the other user via the messengers, it can be generated by the medical image sharing and 3D/4D rendering browser, application, or server S110 and provided to individual users. Alternatively, any one user can receive information about a link generated by the medical image sharing and 3D/4D rendering browser, application, or server S110, and can provide it to the other user.

In this case, it will be apparent that in order to directly provide information about a link from the medical image sharing and 3D/4D rendering browser, application, or server S110 to the second user S130, the medical image sharing and 3D/4D rendering browser, application, or server S110 should acquire information about the second user of the second user in advance. This will be described in detail when the medical image sharing and 3D/4D rendering browser, application, or server S110 is described later.

The messenger provided in each user is a real-time remote collaborative diagnosis-enabled messenger. The messenger can a messenger specialized for the medical image sharing and 3D/4D rendering browser, application, or server S140, for example, a Picture Archival and Communication System (PACS), and can optionally include an interface constructed to share medical images.

In this case, the first user can set information about the sharing of a sharing-target medical image using a user interface provided in the messenger of the first user S120. The set information about the sharing can include the range of the sharing of sharing-target medical image-related information, a sharing-target medical image control method, operation control authority, etc. In this case, the sharing-target medical image-related information can include information about whether the second user can adjust and/or edit the sharing-target medical image, the ranges of adjustment and/or editing, whether CAD results, annotations, windowing, rendering, etc. are shared. Furthermore, the operation control authorities can include not only the authority to perform user input related to a sharing-target medical image but also the authority to perform annotation, windowing, and rendering. That is, the first user can set the range of information sharing related to a sharing-target medical image, access authority, operation control, etc. when a collaborative diagnosis is made.

The set information about the sharing of the sharing-target medical image can be transmitted to the medical image sharing and 3D/4D rendering browser, application, or server S110 using the user interface. The medical image sharing and 3D/4D rendering browser, application, or server S110 can transmit data to the second user while taking into consideration the information about the sharing.

The second user S130 is the user of the second user that communicates with the first user S120 in order to make a collaborative diagnosis. The second user S130 is requested to perform a collaborative diagnosis by the first user S120 via the messenger of the first user S120 and the messenger of the second user S130, accepts the request via the approval of the second user, performs a synchronization process, and then receives information about a link to a sharing-target medical image from the medial image sharing and 3D/4D rendering browser, application, or server S110, thereby receiving the sharing-target medical image corresponding to the information about a link from the medical image sharing and 3D/4D rendering browser, application, or server S110 and then displaying the sharing-target medical image on a screen.

The first user S120 can exchange information about links to a sharing-target medical image, an annotation, text, voice, etc. with the second user S130 via the messengers or medical image sharing and 3D/4D rendering browser, application, or server S110. The first and second users S120 and S130 can share the sharing-target medical image, the annotation, the text, the voice, etc. via the medical image sharing and 3D/4D rendering browser, application, or server S110 based on the exchanged information about links. It will be apparent that in the case of the second user S130, information to be shared and user input can be limited based on the information about the sharing of the sharing-target medical image set by the first user.

The medical image sharing and 3D/4D rendering browser, application, or server S110 is a browser, application, or server that enables the sharing of a medical image and medical image-related information so that the first and second users S120 and S130 can make a collaborative diagnosis. The medical image sharing and 3D/4D rendering browser, application, or server S110 optionally provides the sharing-target medical image requested by the first user of the first user S120 to the first user S120, receives information about the second user of the second user S130, optionally provides the sharing-target medical image (hereinafter referred to as the "first sharing-target medical image") to the second user S130, processes the first sharing-target medical image based on a user input entered by any one of the two users, generates a sharing-target medical image related to the results of processing of the first sharing-target medical image (hereinafter referred to as the "second sharing-target medical image"), and optionally provides the second sharing-target medical image to the first and second users S120 and S130.

In this case, the processing of the first sharing-target medical image can include an operation, such as rotation, expansion, or reduction, can include an operation of overlaying an annotation on a screen, and can include CAD results or rendering.

The medical image sharing and 3D/4D rendering browser, application, or server S110 can receive the information about the second user from any one of the first and second users S120 and S130. The time at which the information about the second user is received is the time at which the first and second users S120 and S130 are synchronized if synchronization is achieved via the messengers of the two users.

The time at which the information about the second user is received is the time at which the first user of the first user selects the second user if synchronization is achieved via the medical image sharing and 3D/4D rendering browser, application, or server S110.

The medical image sharing and 3D/4D rendering browser, application, or server S110 can search for a medical image requested by each of the users and then provide the medical image.

In the present invention, the medical image sharing and 3D/4D rendering browser, application, or server S110 can provide at least one medical image to two or more users to enable a collaborative diagnosis to be made, and can also provide at least one medical image generated through the processing of user input to the users. Furthermore, the medical image sharing and 3D/4D rendering browser, application, or server S110 can search for related users and provide information about the retrieved users to the first user S120 so that the first user S120 can easily select the second user.

As an example, the medical image sharing and 3D/4D rendering browser, application, or server S110 can search for a plurality of users corresponding to the characteristic information of the first sharing-target medical image from among previously stored users based on the characteristic information of the first sharing-target medical image requested by the first user S120, and can provide information about the plurality of retrieved users to the first user S120, thereby allowing the first user to select the second user along with whom a collaborative diagnosis will be made.

In this case, the characteristic information of a medical image can include the type of medical imaging apparatus that has captured the medical image, for example, a computerized tomography (CT) scanner, a magnetic resonance imaging (MRI) scanner, a positron emission tomography (PET) scanner or an X-ray machine, a captured bodily region, a region of interest in the medical image, a field related to the sharing-target medical image, etc.

As another example, the medical image sharing and 3D/4D rendering browser, application, or server S110 can search for a plurality of users corresponding to information about the first user from among previously stored users based on the information about the first user, and can provide the plurality of retrieved users to the first user S120, thereby enabling the first user to select the second user along with whom a collaborative diagnosis will be made.

In this case, the information about the first user can include the department, professional field (for example, specialized cancer treatment) and/or the like of the first user, and can also include all user information that can be applied in connection with a collaborative diagnosis.

If needed, the medical image sharing and 3D/4D rendering browser, application, or server S110 can search for a plurality of users from among previously stored users while taking into consideration the characteristic information of the first sharing-target medical image and information about the first user. As a still another example, the medical image sharing and 3D/4D rendering browser, application, or server S110 can store information about a plurality of groups including a plurality of users, and can provide information about a corresponding group requested by the first user to the first user, thereby enabling the first user to select the second user from among users included in the information about a corresponding group.

In this case, the information about a user group can be classified according to its professional field (a medical department), in which case the information about a user group optionally includes users in a corresponding field. Furthermore, the information about a user group can include information about a basic group set by the first user. The users included in the information about a basic group can be added, modified and/or deleted by the first user.

Furthermore, the medical image sharing and 3D/4D rendering browser, application, or server S110 can receive the information about sharing set by the first user from the first user S120, can store the received information about sharing together with the sharing-target medical image, and can provide both the information about sharing and the sharing-target medical image to the second user S130.

Furthermore, when at least one of annotation, text and voice information is received from any one of the two users, the medical image sharing and 3D/4D rendering browser, application, or server S110 can provide the received information to the other user, thereby enabling the two users to share the corresponding information.

In this case, although the medical image sharing and 3D/4D rendering browser, application, or server S110 can provide the corresponding information directly to the two users, the medical image sharing and 3D/4D rendering browser, application, or server S110 can provide information about a link to the corresponding information, thereby allowing the corresponding information to be provided to the two users via information about the link.

Moreover, the medical image sharing and 3D/4D rendering browser, application, or server S110 can store image and text result data attributable to a collaborative diagnosis, for example, a sharing-target medical image manipulated by user input, and/or an annotation, windowing and/or rendering input by the first or second user. This collaborative diagnosis result data can be stored in a database table that has been mapped to the corresponding image data. The medical image sharing and 3D/4D rendering browser, application, or server S110 can provide the collaborative diagnosis result data stored in the database table for reference when the corresponding image data is read in the future. It will be apparent that the collaborative diagnosis result data stored in the medical image sharing and 3D/4D rendering browser, application, or server S110 can be stored in response to a request from the first or second user who makes a collaborative diagnosis. Although it is preferable to store the collaborative diagnosis result data in response to a request from the first user who has requested a collaborative diagnosis, the present invention is not limited thereto. If the second user has the authority related to storage, the collaborative diagnosis result data can be stored in response to a request from the second user. The collaborative diagnosis result data stored in the medical image sharing and 3D/4D rendering browser, application, or server S110 can be updated by the first and second users who make the collaborative diagnosis. It is preferred that the collaborative diagnosis result data be updated by the first user who has requested the collaborative diagnosis.

As described above, the cloud, internet, and/or browser, application, or server based medical image sharing and 3D/4D rendering system according to the present invention enables a medical image to be shared between the users via the medical image sharing and 3D/4D rendering browser, application, or server in order to enable a collaborative diagnosis, thereby reducing traffic between the messengers, that is, between the users, improving the security of the medical image and the protection of private information, and also reducing the traffic of the medical image sharing and 3D/4D rendering browser, application, or server because a collaborative diagnosis is made via the messengers.

Although FIG. 12 illustrates that the first user of the first user requests a collaborative diagnosis, the second user of the second user accepts the request and thus a medical image is shared, the present invention is not limited thereto, and vice versa. Furthermore, after the first user and the second user have been synchronized with each other, a new medical image can be shared via the medical image sharing and 3D/4D rendering browser, application, or server in response to a request form the first or second user.

In FIG. 12, the embodiment in which the screen of the results of operations, for example, rotation, performed on an image being shared between users participating in a remote collaborative diagnosis is shared has been illustrated. However, it will be apparent that the spirit of the present invention is not limited to this embodiment. In another embodiment of the present invention, the results of operations, for example, expansion, reduction, the changing of direction (the changing of a view point), and rotation, performed on an image being shared between users participating in a remote collaborative diagnosis can be synchronized and shared. Furthermore, the annotation information of any one user related to a shared image can be displayed to other users in a synchronized state. When any one user has selected a medical image of interest from a set of various medical images, the results of the selection can be provided to other users. When a plurality of medical images is displayed, the results of switching between screens performed by any one user can be also provided to other users.

Meanwhile, an operation, such as the rotation, expansion or reduction of an image, performed in response to a request from a user, can be performed on 3D medical images obtained by 3D rendering, and can also be performed on two-dimensional (2D) medical images, such as CT and MRI tomographic slice images, sagittal, coronal and axial images, multi-planar reformatting (MPR) images, etc.

Furthermore, the results of additional processing performed in response to a request from any one user can be shared with other users. Examples of additional processing include 3D rendering, segmentation related to a Region of Interest (ROI), such as a tumor, and CAD results.

An operation, the display of an annotation, the selection of an image, the switching between screens, additional processing, and/or the like can be executed by the medical image sharing and 3D/4D rendering browser, application, or server S110 in response to a request from any one user. The results of the execution can be shared among the users of a plurality of users.

In this case, when an operation, the addition of an annotation, the selection of an image, a request for the switching between screens, or a request for additional processing is input by any one user via a user interface, the system according to the present invention can additionally provide a confirmation menu that is used to check whether to share the processing results of the request with other users. The confirmation menu can be selectively provided by taking into consideration factors, such as the processing cost of a user request, resources for the processing of the user request, and/or the processing time of the user request. That is, the confirmation menu that is used to check whether to share the processing results of the request with other users is provided if the user request occupies many resources or requires a long processing time, and the processing results of the request can be shared with other users without providing the confirmation menu if the user request can be immediately processed.

In contrast, the confirmation menu that is used to check whether to share the processing results of a user request with other users can be provided depending on whether a user request is closely related to the private information of a patient, rather than depending on the processing cost, resources and processing time of the user request. In this case, even for the same screen operation, whether to provide the confirmation menu can be determined depending on the type of lesion or organ that is related to a user request.

The operations between the first user S120, the second user S130 and the medical image sharing and 3D/4D rendering browser, application, or server S110 that constitute the system of the present invention will be described in greater detail with reference to FIGS. 14 and 15.

Figure 14:
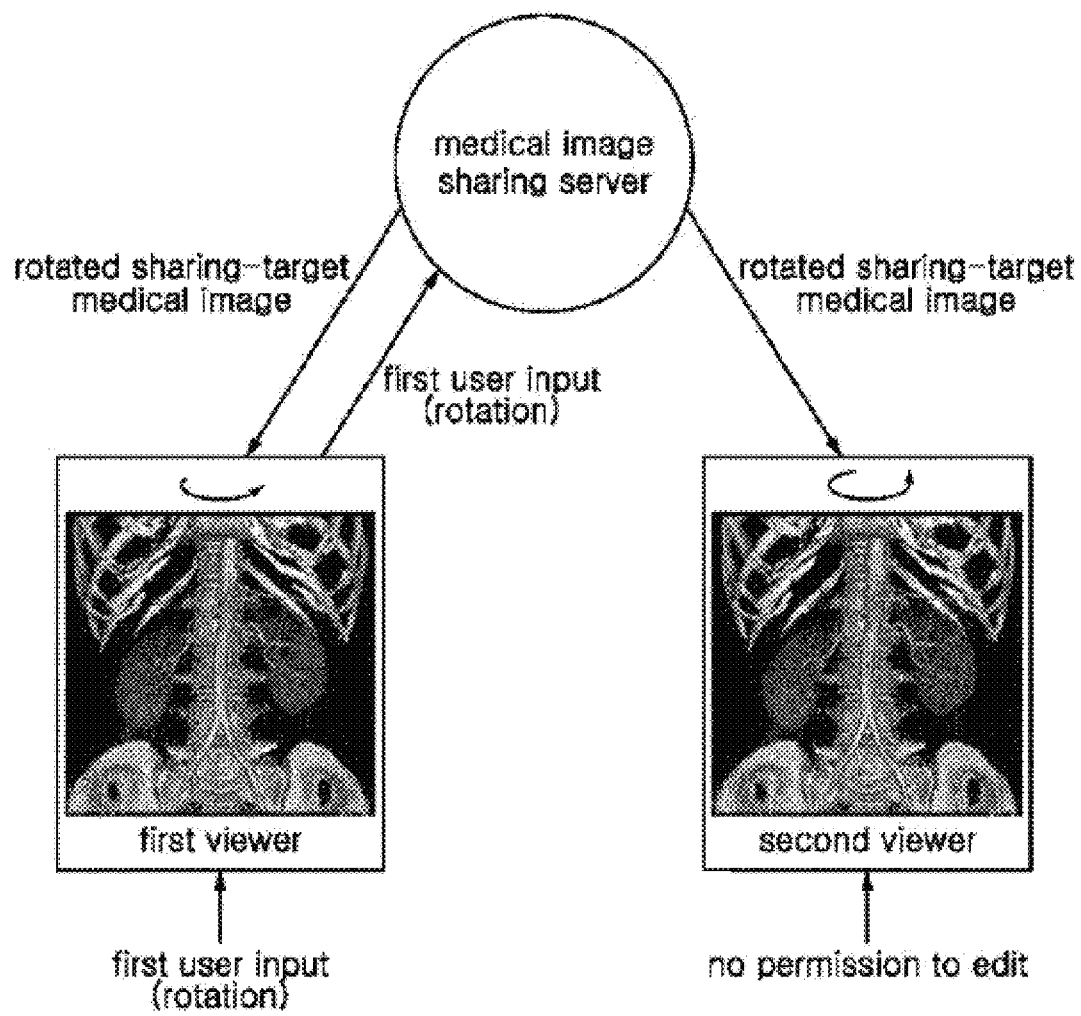
FIG. 14 is a diagram illustrating an example of controlling the medical image shared between the two viewers of FIG. 1.
Figure 15:
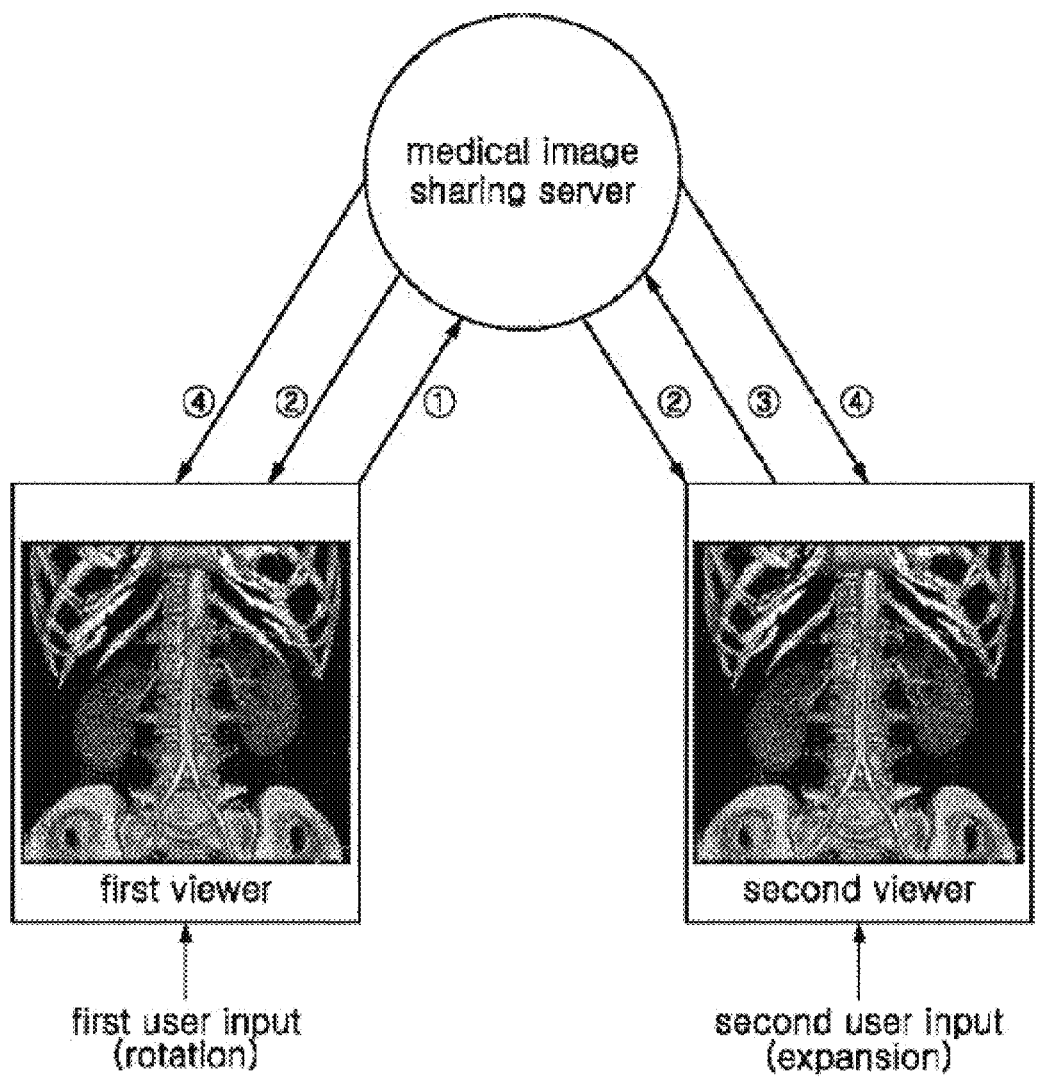
FIG. 15 is a diagram illustrating another example of controlling the medical image shared between the two viewers of FIG. 1.

FIGS. 14 and 15 are diagrams illustrating examples of controlling a medical image shared between two users. FIG. 14 illustrates an example in which a sharing-target medical image cannot be adjusted and edited via the second user. FIG. 15 illustrates an example in which a sharing-target medical image can be freely adjusted and edited via the first and second users.

In this case, information about whether or not a sharing-target medical image can be manipulated via the second user can be set by the first user of the first user.

(1) As shown in FIG. 12, if the first user has set a sharing-target medical image control method so that a counterparty, that is, the second user of the second user S120 cannot adjust and edit the sharing-target medical image, only an operation input by the first user of the first user S120 can influence the sharing-target medical image displayed on the second user S130, and the second user of the second user S130 cannot perform any operation on the sharing-target medical image. For example, as illustrated in FIG. 14, when the first user of the first user S120 performs an operation of rotating a sharing-target medical image, information about the rotation-related user operation is provided to the medical image sharing and 3D/4D rendering browser, application, or server S110, and the medical image sharing and 3D/4D rendering browser, application, or server S110 generates a rotated sharing-target medical image, that is, a second sharing-target medical image, by processing the rotation of the sharing-target medical image, that is, a first sharing-target medical image, and optionally provides the generated second sharing-target medical image to the first and second users S120 and S130, thereby enabling the rotated sharing-target medical image to be shared between the first and second users S120 and S130.

(2) If the first user has set a sharing-target medical image control method so that a counterparty, that is, the second user of the second user S130 can freely adjust (the field of view, angle, zoom-in and zoom-out of) a sharing-target medical image, an operation input by the first user of the first user S120 can influence the sharing-target medical image displayed on the second user S130, and an operation input by the second user of the second user S130 can influence the sharing-target medical image displayed on the first user S120. For example, as illustrated in FIG. 15, when the first user of the first user S120 performs an operation of rotating a sharing-target medical image, information about the rotation-related user operation "a" is provided to the medical image sharing and 3D/4D rendering browser, application, or server S110, the medical image sharing and 3D/4D rendering browser, application, or server S110 can generate a rotated sharing-target medical image, that is, a second sharing-target medical image, by processing the rotation of the sharing-target medical image, that is, a first sharing-target medical image, and can provide the generated second sharing-target medical image "b" to the first and second users S120 and S130, thereby enabling the rotated sharing-target medical image to be shared between the first and second users S120 and S130. In the same manner, when the second user of the second user S130 performs an operation of expanding a sharing-target medical image, information about the expansion-related user operation "c" is provided to the medical image sharing and 3D/4D rendering browser, application, or server S110, the medical image sharing and 3D/4D rendering browser, application, or server S110 can generate an expanded sharing-target medical image by processing the expansion of a currently shared sharing-target medical image, and can provide the expanded sharing-target medical image "d" to the first and second users S120 and S130, thereby enabling the expanded sharing-target medical image to be shared between the first and second users S120 and S130.

Figure 13:
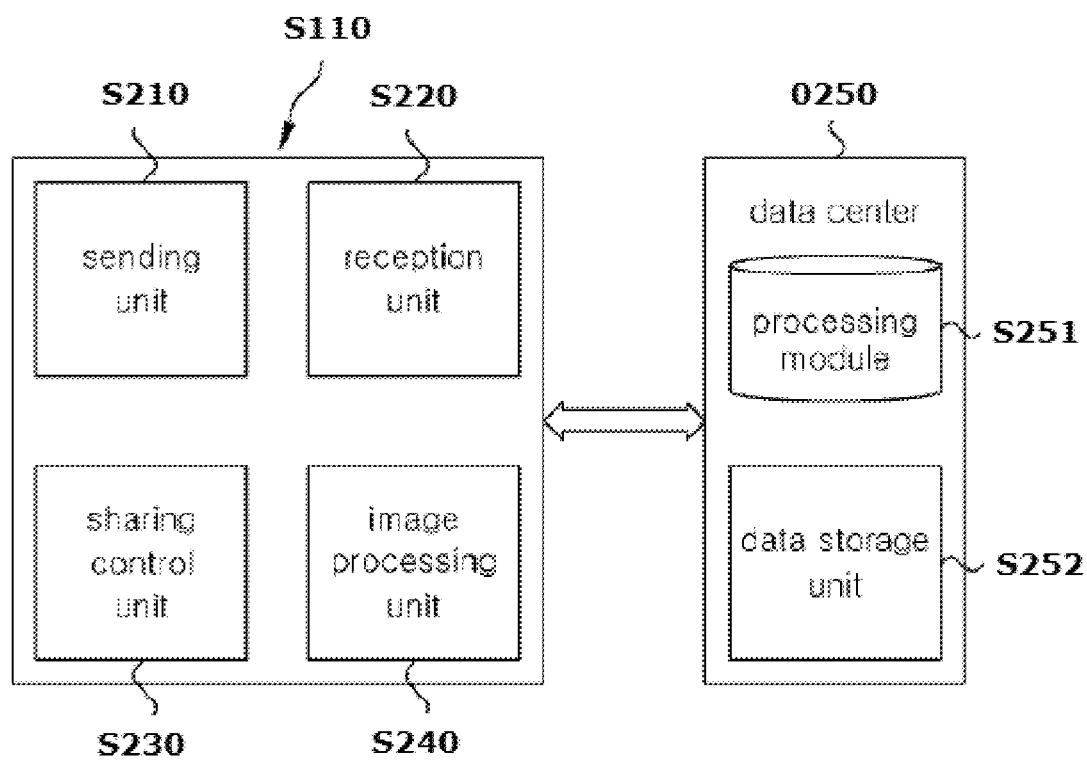
FIG. 13 is a diagram illustrating the configuration of the medical image sharing browser, application, or server illustrated in FIG. 1 according to an embodiment of the present invention.

FIG. 13 is a diagram illustrating the configuration of the medical image sharing and 3D/4D rendering browser, application, or server illustrated in FIG. 12 according to an embodiment of the present invention.

Referring to FIG. 13, the medical image sharing and 3D/4D rendering browser, application, or server S110 optionally includes a sending unit S210, a reception unit S220, a sharing control unit S230, and a image processing unit S240, and can further include a data center S250 in some situations. The sending unit S210 optionally provides a first medical image requested by the first user of the first user to the first user. The sending unit S210 can be configured to be under control of a processor sub-module (not shown) included in the browser, application, or server S110.

In this case, the sending unit S210 can provide information about a plurality of users to the first user in order to enable the second user to be selected.

As an example, the sending unit S210 can check the previously stored characteristic information of the first medical image requested by the first user, can search for a plurality of users corresponding to the characteristic information of the first medical image from among previously stored users, and can provide information about the plurality of retrieved users to the first user.

In this case, the characteristic information of the medical image can include the type of medical imaging apparatus that has captured the medical image, for example, a CT scanner, a MRI scanner, a PET scanner or an X-ray machine, a captured bodily region, a region of interest in the sharing-target medical image, a field related to the sharing-target medical image, etc.

As another example, the sending unit S210 can search for a plurality of users corresponding to information about the first user of the first user from among previously stored users based on the information about the first user, and can provide information about the plurality of users to the first user.

In this case, the information about the first user can include the department, professional field (for example, specialized cancer treatment) and/or the like of the first user, and can also include all user information that can be applied in connection with a collaborative diagnosis. Furthermore, the information about the first user can further include history information indicating that the first user has selected users in order to make collaborative diagnoses. The history information can include the characteristic information of sharing-target medical images, information about the selected users, and collaborative diagnoses-related information.

As another example, the sending unit S210 can provide information about a corresponding group requested by the first user and selected from among information about a plurality of user groups including a plurality of users to the first user.

In this case, the request from the first user can be received via a user interface provided in the first user or messenger.

In this case, the information about a user group can be classified according to its professional field (a medical department), in which case the information about a user group optionally includes users in a corresponding field. Furthermore, the information about a user group can include information about a basic group set by the first user.

As described above, the sending unit S210 can search for a plurality of users corresponding to a specific criterion from among previously stored users, and can provide information about the plurality of retrieved users to the first user. The information about the users stored in the medical image sharing and 3D/4D rendering browser, application, or server S110 can be updated at regular time intervals. The information about the retrieved users provided to the first user 1S20 can include information about the priorities of users in each related field.

The reception unit S220 receives information about a second user who will make a collaborative diagnosis while sharing the first medical image with the first user. The reception unit S220 can be configured to be under control of the processor sub-module (not shown) included in the browser, application, or server 110.

In this case, the reception unit S220 can receive the information about a second user from the first user or from the second user. The reception unit S220 can receive the information about a second user when the first and second users are synchronized with each other via the messengers provided in the respective users. The information about a second user received by the reception unit S220 refers to information about a user who is selected by the first user from among the plurality of users that are provided by the sending unit S210 to the first user.

Furthermore, the reception unit S220 can receive information about the sharing of the first medical image set by the first user of the first user. The information about the sharing of the first medical image can include information about first medical image-related information that is allowed to be provided to the second user and information about the allowed operations of the second user.

The reception unit S220 can receive an annotation, text, voice, etc. input by any one of the first and second users in the state in which the first medical image has been shared between the two users, and can provide the received information to the user of the other user via the sharing control unit S230. The sharing control unit S230 controls the sending unit S210 to provide the first medical image to the second user of the second user based on the information about the second user received from the reception unit S220. That is, the sharing control unit S230 enables the medical image to be shared between the first and second users that make a collaborative diagnosis. The sharing control unit S230 can be configured to be a functional sub-module of the processor (not shown) included in the browser, application, or server S110. Furthermore, the sharing control unit S230 can provide information about the sharing of the first medical image set by the first user to the second user along with the first medical image.

Furthermore, the sharing control unit S230 can provide annotation, text, and/or voice information received by the reception unit S220 to the users, thereby enabling the annotation, text, and/or voice information to be shared. Furthermore, the sharing control unit S230 can provide a second medical image generated by the image processing unit S240 in response to the user input of the first or second user to the first and second users, thereby enabling the second medical image to be shared. The image processing unit S240 can be configured to be a functional sub-module of the processor (not shown) included in the browser, application, or server S110.

When user input related to the manipulation of the first medical image is received from any one of the first and second users, the image processing unit S240 can process the first medical image based on the received user input, can generate a second medical image related to the first medical image, and can provide the second medical image to the first and second users via the sharing control unit S230.

In this case, the processing of the medical image performed by the image processing unit S240 can include operations, such as rotation, expansion, and reduction, can include an operation of overlaying an annotation on a screen, and can include 3D rendering, a region of interest (ROI) such as a tumor, segmentation related to the ROI or, CAD results.

The data center S250 optionally includes a processing module S251 and a data storage unit S252, and can be viewed as an element that is used to centralize data therein in order to construct a thin-client environment. The data center S250 can be configured to be included in the medical image sharing and 3D/4D rendering browser, application, or server S110, and can be implemented as a separate means.

The data storage unit S252 is a means that stores all information related to the present invention, for example, a medical image, user information, and medical image-related information.

The processing module S251 can include an image processing module for processing rendering and the like, and can process a sharing-target medical image in response to a request from the image processing unit S240. It will be apparent that the processing module S251 can be configured to be included in the image processing unit S240.

Figure 16:
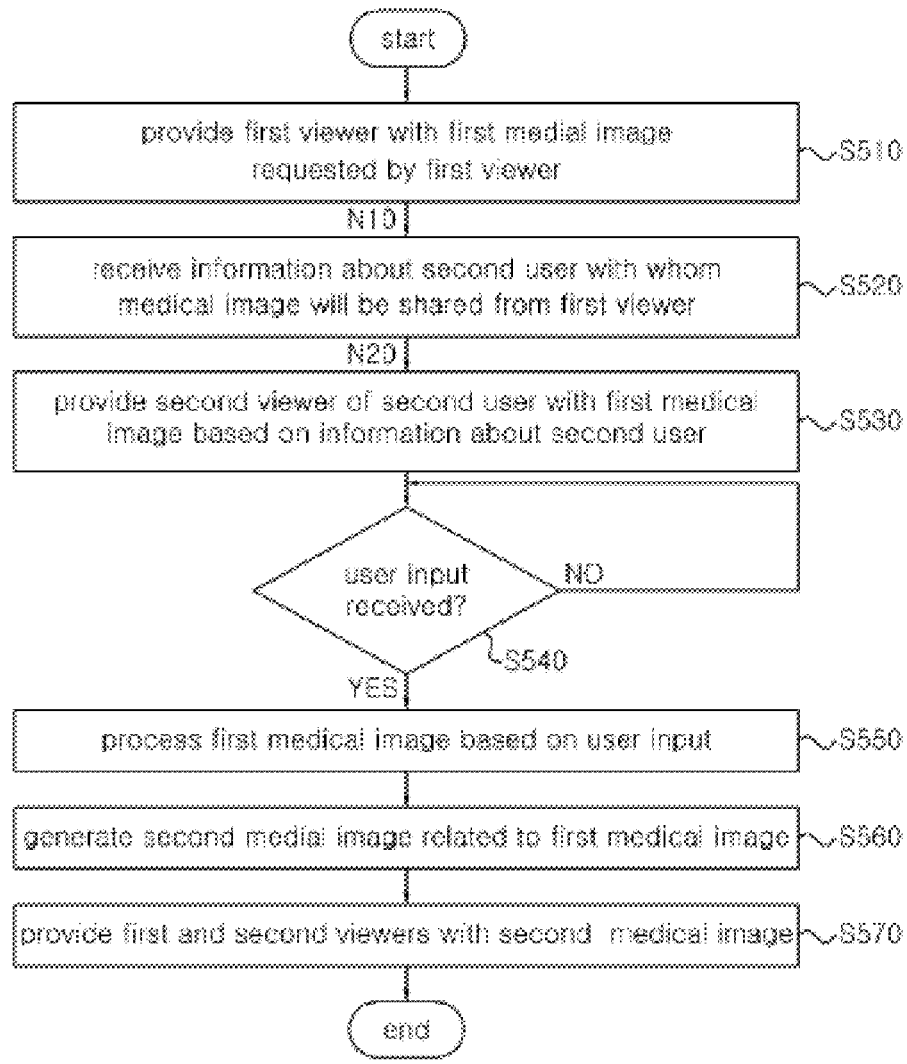
FIG. 16 is a flowchart illustrating the process of a cloud, internet, and/or browser, application, or server based medical image sharing method according to an embodiment of the present invention.

FIG. 16 is a flowchart illustrating the process of a cloud, internet, and/or browser, application, or server based medical image sharing and 3D/4D rendering method according to an embodiment of the present invention. That is, FIG. 16 illustrates the operation of the medical image sharing and 3D/4D rendering browser, application, or server illustrated in FIG. 12.

Referring to FIG. 16, in the cloud, internet, and/or browser, application, or server based medical image sharing and 3D/4D rendering method according to the present invention, a sharing-target medical image (first medical image), the sharing of which is requested by the first user, is searched for and is provided to the first user at step S510.

Once the first medical image has been provided to the first user and a second user along with whom a collaborative diagnosis will be made has been selected by the first user of the first user, information about the second user is received from the first or second user at step S520.

In this case, at step S520, the information about a second user can be received when synchronization is achieved via the messengers provided in the first and second users, or the information about a second user can be received at the time at which the second user is selected by the first user.

Furthermore, at step S520, not only the information about the second user but also information about the sharing of the first medical image set by the first user can be received.

Once the information about the second user has been received at step S520, the first medical image is provided to the second user of the second user based on the received information about a second user at step S530.

In this case, the medical image sharing and 3D/4D rendering browser, application, or server can provide information about a link to the first medical image to the second user, and the first medical image can be provided to the second user based on the information about a link. The information about a link can be provided directly from the medical image sharing and 3D/4D rendering browser, application, or server to the second user, and can be provided from the first user to the second user via the messengers. Then the second user can access the first medical image via the shared link Depending on one of example of the invention, the second user can access the first medical image only via the shared link. In this case, the access permission of second user to the first medical image can be partially limited by the medical image sharing and 3D/4D rendering browser, application, or server.

Furthermore, at step S530, the information about the sharing of the first medical image received from the first user can be provided to the second user along with the first medical image.

Once the first medical image has been shared between the first and second users, it is determined whether user input is received from the first user of the first user or the second user of the second user at step S540.

In this case, at step S540, if it is determined based on the information about sharing set by the first user of the first user that the information about the sharing of the first medical image has been set such that the second user cannot perform an operation and/or editing, second user input can be disregarded even when the second user input is received.

When a user input is received from user any one user, the first medical image is processed based on the received user input at step S550, and then a second medical image related to the first medical image is generated at step S560.

In this case, step S550 can include both the case where the information about the sharing of the first medical image allows an operation and/or editing to be performed by the second user and the case where the information about the sharing of the first medical image does not allow an operation and/or editing to be performed by the second user. The second medical image can refer to a medical image that is generated by applying rotation, expansion, reduction, rendering, the addition of an annotation, and/or the addition of CAD results to the first medical image based on user input.

Once the second medical image has been generated, the generated second medical image is provided to the first and second user at step S570.

Figure 17:
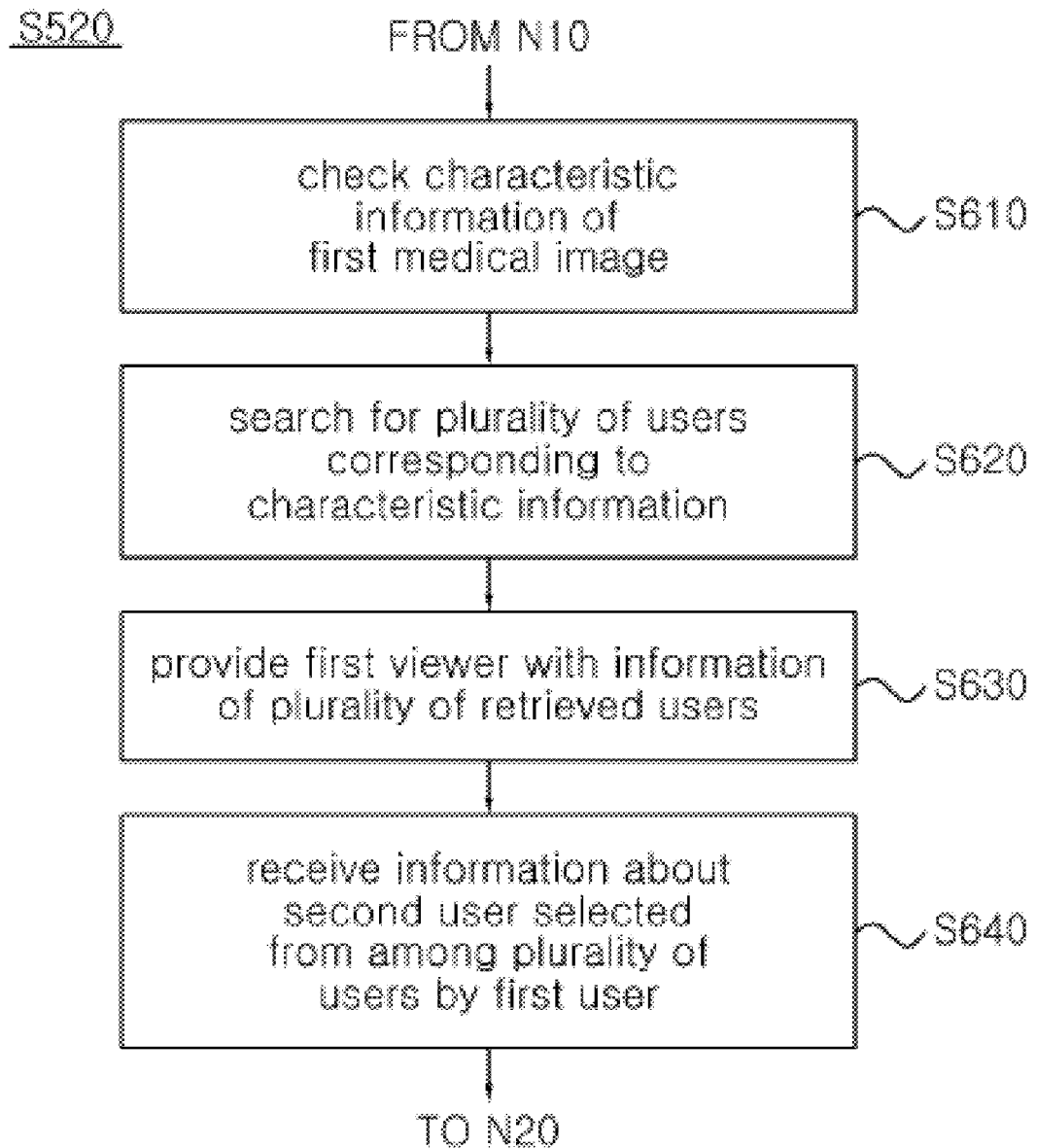
FIG. 17 is a flowchart illustrating the detailed process of step S520 illustrated in FIG. 5 according to an embodiment of the present invention.

Although not illustrated in the drawings, when an annotation, text, voice and/or the like are received from any one user in a state in which the first medical image has been shared between the two users, the received annotation, text, voice and/or the like to the other user, thereby enabling them to be shared. FIG. 17 is a flowchart illustrating the detailed process of step S520 illustrated in FIG. 16 according to an embodiment of the present invention.

Referring to FIG. 17, in step S520 of receiving information about the second user, the characteristic information of the first medical image requested by the first user is checked at step S610, and a plurality of users corresponding to the characteristic information of the first medical image are searched for from among previously stored users at step S620.

In this case, the characteristic information of the medical image can include the type of medical imaging apparatus that has captured the medical image, for example, a CT scanner, a MRI scanner, a PET scanner or an X-ray machine, a captured bodily region, a region of interest in the sharing-target medical image, a field related to the sharing-target medical image, etc.

Once the plurality of users has been retrieved, information about the plurality of retrieved users is provided to the first user at step S630, and, when a second user is selected from among the plurality of users by the first user of the first user, information about the selected second user is received at step S640. Although the information about the second user can be received from the first user, the present invention is not necessarily limited thereto.

Figure 18:
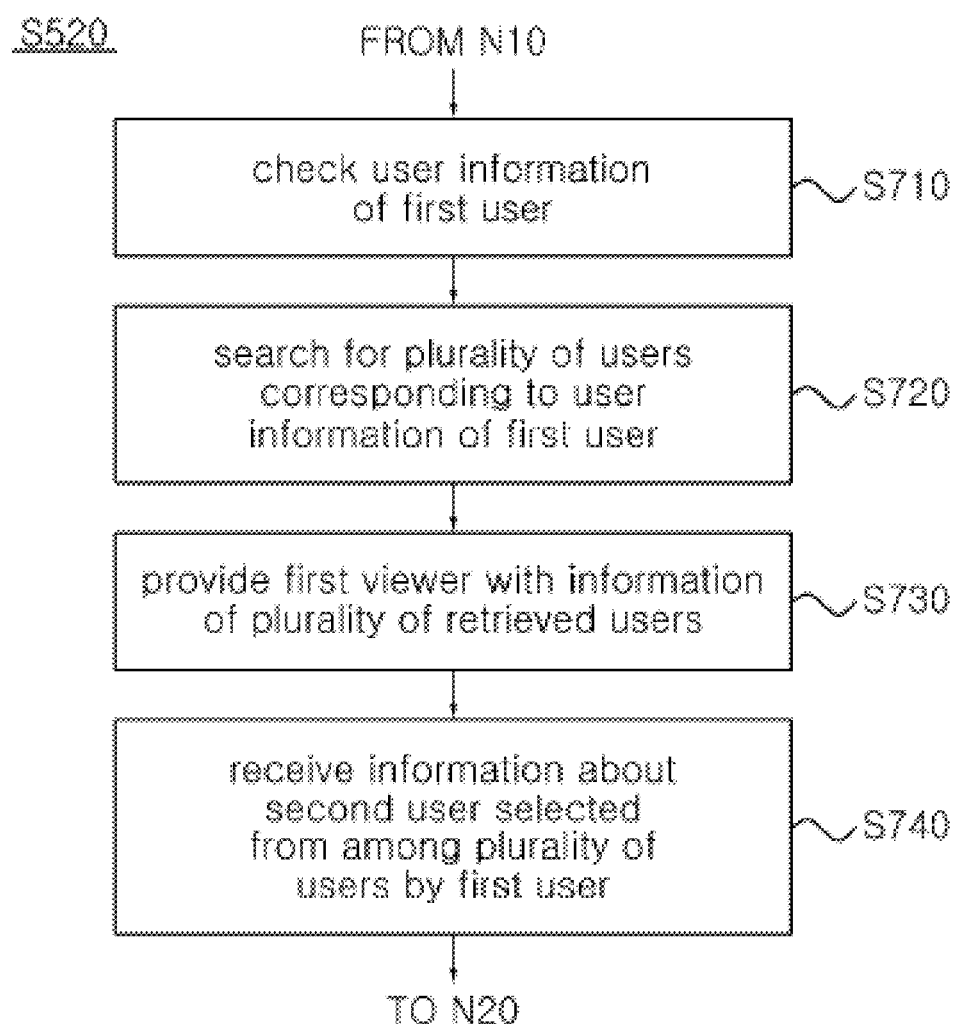
FIG. 18 is a flowchart illustrating the detailed process of step S520 illustrated in FIG. 5 according to another embodiment of the present invention.
Figure 19:
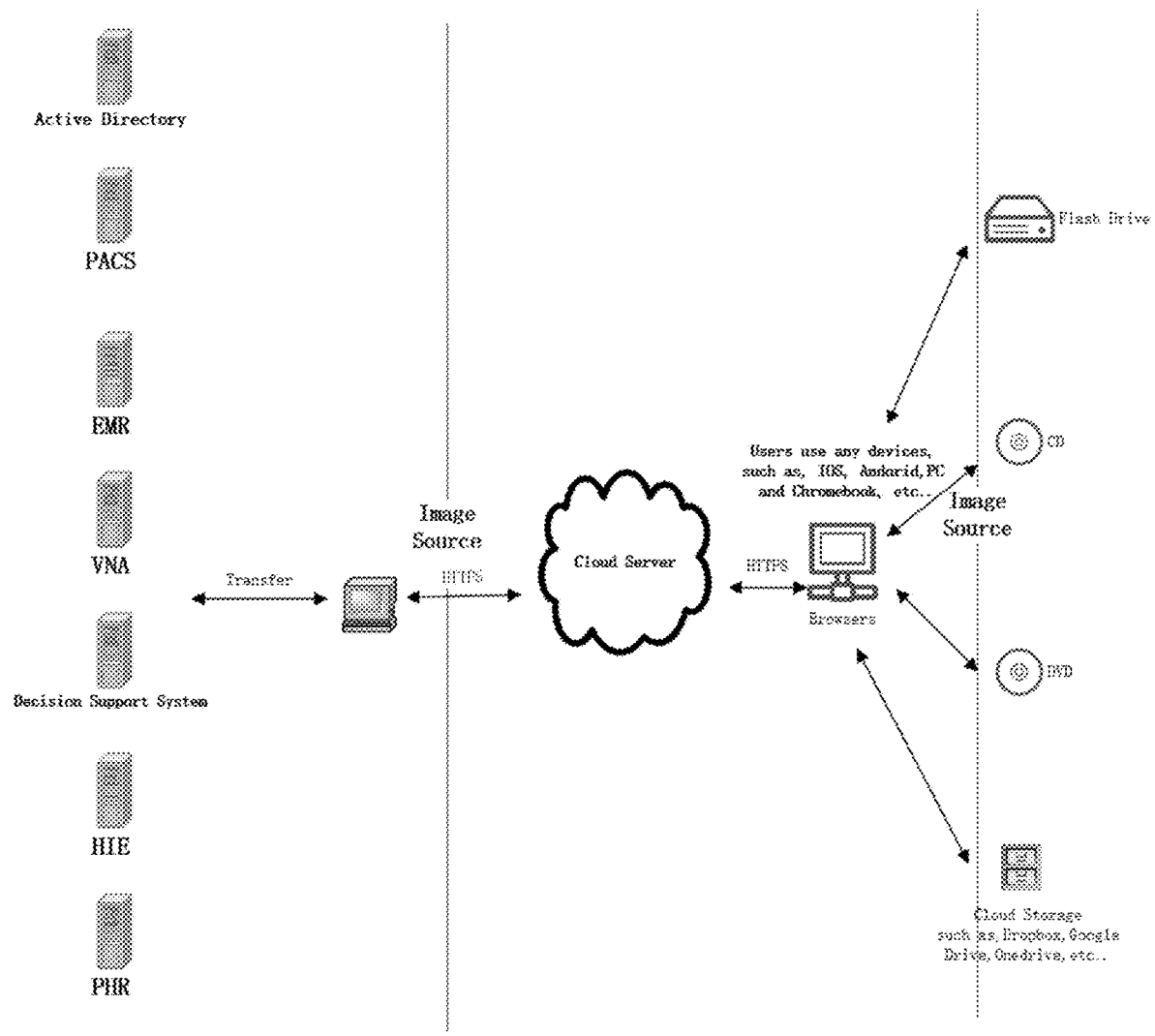
FIG. 19 is a schematic diagram showing public cloud deployment of an image sharing method, system, and apparatus of non-limiting embodiments of the invention.
Figure 20:
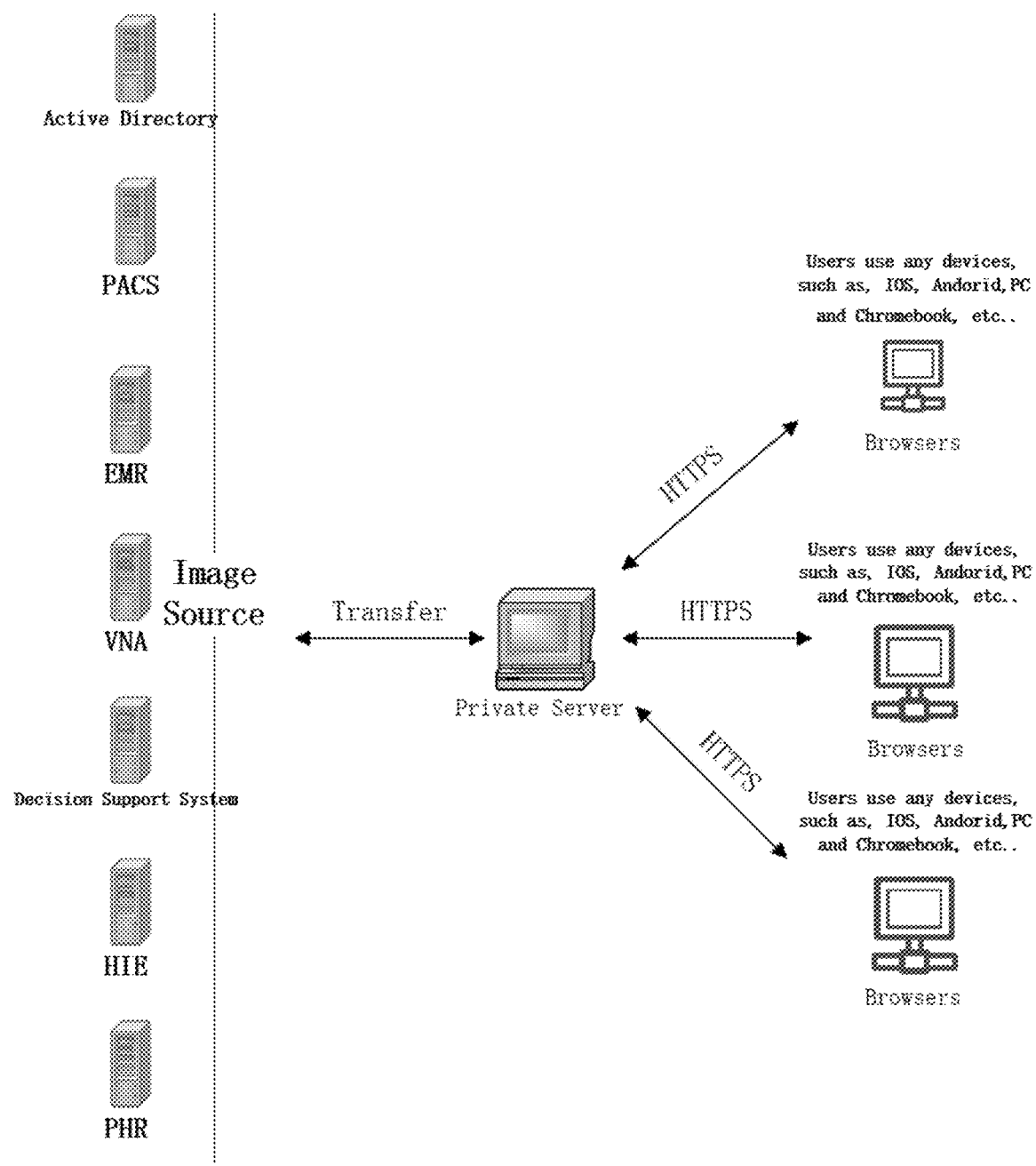
FIG. 20 is a schematic diagram showing private cloud deployment of an image sharing method, system, and apparatus of non-limiting embodiments of the invention
Figure 21:
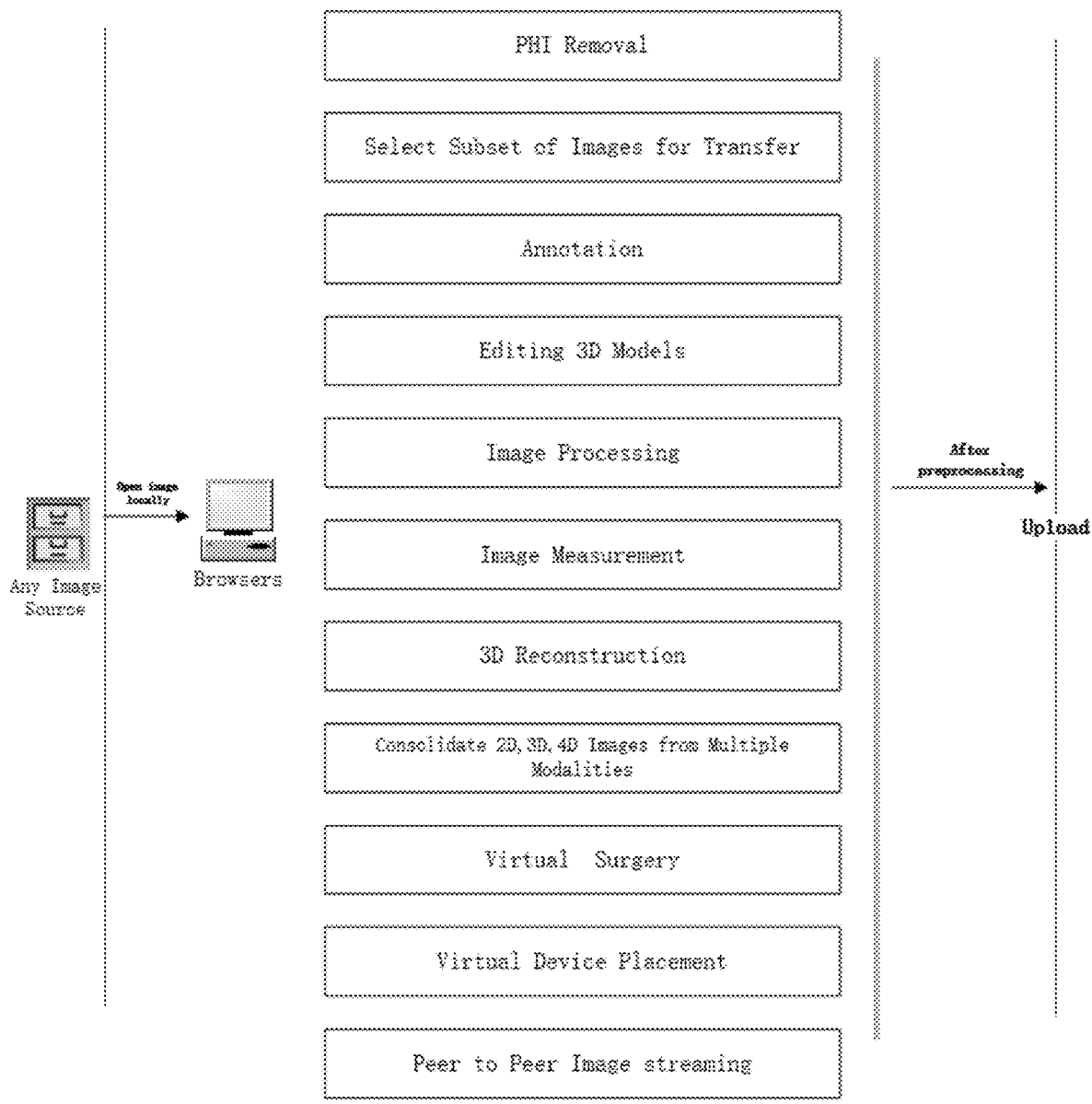
FIG. 21 is a schematic diagram showing image preprocessing before uploading of an image sharing method, system, and apparatus of non-limiting embodiments of the invention.
Figure 22:
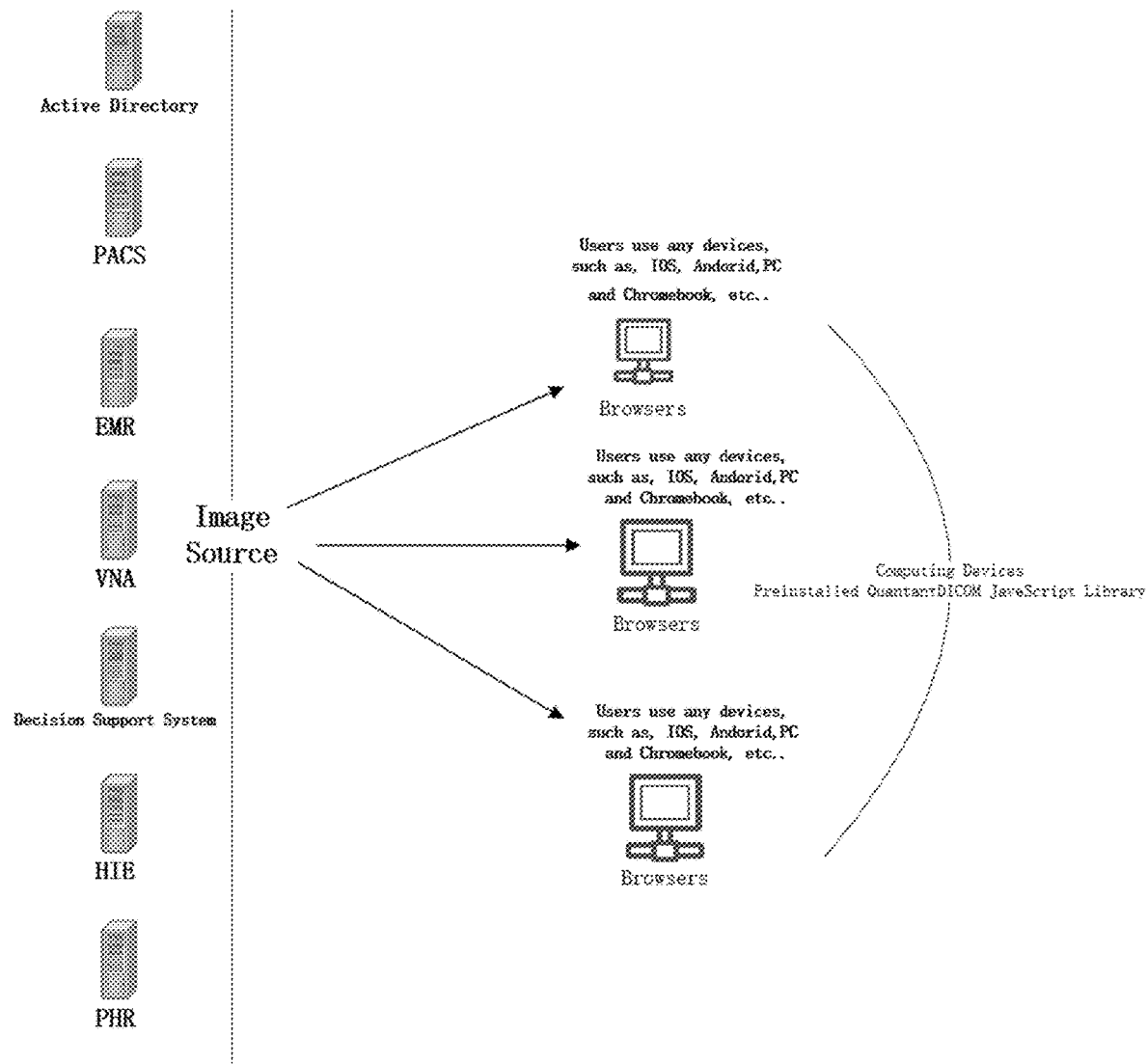
FIG. 22 is a schematic diagram showing browser, application, or server-less deployment (JavaScript library is pre-installed on computing devices) of an image sharing method, system, and apparatus of non-limiting embodiments of the invention.

FIG. 18 is a flowchart illustrating the detailed process of step S520 illustrated in FIG. 16 according to another embodiment of the present invention.

Referring to FIG. 18, in step S520 of receiving information about the second user, information about the first user who has requested the first medical image is checked at step S710, and a plurality of users corresponding to the information about the first user are searched for from among previously stored users at step S720.

In this case, the information about the first user can include the department, professional field (for example, specialized cancer treatment) and/or the like of the first user, can further include history information indicating that the first user has selected users in order to make collaborative diagnoses, and can further include all user information that can be applied in connection with a collaborative diagnosis. The history information can include the characteristic information of sharing-target medical images, information about the selected users, and collaborative diagnoses-related information.

Once the plurality of users has been retrieved, information about the plurality of retrieved users is provided to the first user at step S730, and, when the second user is selected from among the plurality of users by the first user of the first user, information about the selected second user is received at step S740.

Furthermore, although not illustrated in the drawings, in step S520 of receiving information about the second user, information about a group corresponding to a request from the first user can be selected from previously stored information about a plurality of groups, the selected information about a group can be provided to the first user, and information about a second user selected by the first user from among a plurality of users included in the information about a group can be received from the first user.

In this case, the request from the first user can be received from the first user by the selection of the first user using the first user or the user interface provided in the messenger.

The 2D/3D/4D imaging can optionally be viewed and further modified by users AFTER receiving the data without the need for special hardware and/or systems, wherein the receiving party of 2D/3D/4D imaging data also can optionally view those contents on any internet-enabled devices or computers without the need to install any extra plug-in. By calling quantantShare.JS library and other server-side software, the receiver can optionally visualize and modify the same contents shared by other parties.

The invention can optionally include one or more aspects of methodology of viewing and/or editing 2D/3D/4D medical image data optionally without the need for special hardware and/or systems that are specific to the type of file being use, e.g., using a web browser without added plugins, such as but not limited to: MS™ Explorer™ or Edge™, Apple™ Safari™, Mozilla™ Firefox™, and the like.

In traditional imaging sharing approaches, special hardware and/or systems are necessary for viewing and editing 2D/3D/4D medical images. For example, one or more of the following can be necessary for viewing and/or editing such files:

Special servers developed to decode 2D/3D/4D medical images (e.g. DICOM images). For parties who would like to view or edit those medical images, he/she needs to make sure that the images are transmitted to these special servers before they can be viewed and/or edited. For example, he/she would need to first send the medical image data to a cloud server, a PACS system or an archiving system before viewing or editing the images.

Alternatively, the parties who would like to view or edit one or more 2D/3D/4D medical images would require the use of specialized software (e.g. a DICOM viewer) installed on a desktop or a mobile device.

Alternatively, the parties who would like to view or edit 2D/3D/4D medical images would need to install specialized browser plugins (e.g. ActiveX, Flash, Java, Silverlight, Chrome Extensions, etc.) in their browsers in order to view or edit the images.

However, according to the present invention, 2D/3D/4D medical image data can be viewed or edited without the need for special hardware and/or system. In other words, browsers would now have the capabilities to decode 2D/3D/4D medical image formats (e.g. DICOM images), a capability that was traditionally possessed only by servers, specialized software or browser plugins.

Such aspects of the invention can optionally include one or more of the following.

Figure 23:
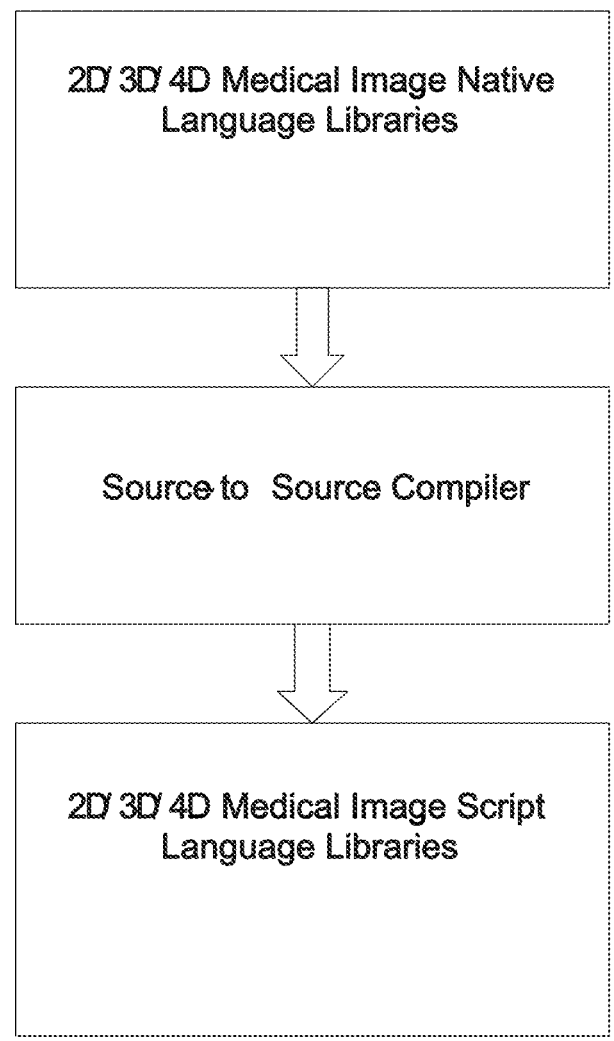
FIG. 23 is a flow diagram describing optional methodology for viewing and/or editing images according to optional embodiments of the invention.

As shown in FIG. 23, 2D/3D/4D medical image formats (e.g. DICOM images) according to the invention can optionally be decoded using known software libraries (for example, GDCM, DCMTK, etc.) accessible directly from the internet on a standard browser with or without any visual display plugins, e.g., where known types of software libraries can optionally include native or known programming languages such as, but not limited to C, Fortran (e.g., Fortran 2003, 2008, and 2015), ESPOL (short for Executive Systems Problem Oriented Language), PL/I, PL/S, PL/8, PL-6, BLISS, SYMPL, Ada, D, Go (Google™) Tust (Mozilla Research™); PL/360, Algol, and C++ (A programming language is a formal constructed language designed to communicate instructions to a machine, particularly a computer. Programming languages can be used to create programs to control the behavior of a machine or to express algorithms. A system programming language usually refers to a programming language used for system programming; such languages are designed for writing system software, which usually requires different development approaches when compared with application software), wherein such software libraries can be accessed and display and editing can be accomplished using browsers with or without display or rendering plugins, optionally without the use of one or more of a cloud server, a PACS system, an archiving system, a specialized desktop/mobile application or one or more browser plugin, where the present invention optionally can edit or display such medical images consistently inside browsers even with limited native language support, as provided in known browsers. This aspect of the present invention optionally provides an unexpected advantage of allowing easy and universally accessible 2D, 3D, and/or 4D medical images or imaging without the use of additional software, hardware, plugins, servers, and/or imaging software or hardware.

As shown in FIG. 23, Imaging viewing, display, and/or editing can optionally include one or more of source-to-source compiler, transcompiler or transpiler techniques, including but not limited to, Low Level Virtual Machine (LLVM), Emscripten, PACL, NACL, the ROSE compiler framework, DMS Software Reengineering Toolkit, and Haxe, A source-to-source compiler, transcompiler or transpiler is a type of compiler that takes the source code of a program written in one programming language as its input and produces the equivalent source code in another programming language. A source-to-source compiler translates between programming languages that operate at approximately the same level of abstraction, while a traditional compiler translates from a higher level programming language to a lower level programming language. Source-to-source compilers can optionally be used to compile native or other software libraries (for example, GDCM, DCMTK, etc.) into an ECMA Script engine (e.g., JavaScript™, TypeScript™, CoffeeScript™, etc.) so that the resulting script library could decode and edit 2D/3D/4D medical images directly inside a browser environment with or without additional plugins or software. An ECMAScript engine is a program that executes source code written in a version of the ECMAScript language standard. ECMAScript engines are used for web browsers, all implementing just-in-time compilation (JIT) or variations of that idea, and which can optionally include one or more of Carakan™ (Opera Software ASA™) (Internet Explorer™ and Edge™); SpiderMonkey™ (Mozilla Research™) (Firefox™); Tamarin™ (Adobe Flash™); V8™ (Google Chrome™); Nashorn™ (Oracle Java Development Kit (JDK)™); Futhark™ (Opera™ web browser versions 9.50 to 10.10); JScript™ (Internet Explorer™ up to IE9); Linear B™ (Opera™ web browser versions 7.0 to 9.50); QtScript™ (Digia™) (QObject™ integration with JavaScriptCore™); Rhino™ (Mozilla™); YAJI™ (Java™ platform, currently being developed to support the latest standards); Jsish™ (JavaScript™ interpreter with builtin SQLite™, JSON™, WebSocket™, and ZVFS™ support); Websocket™.js (embeddable Javascript™ engine with HTTP/Websocket™ support); JerryScript™ (Samsung™ for microcontrollers with less than 64 KB RAM). The performance benefits for just-in-time compilation make it much more suitable for web applications written in JavaScriptSince JavaScript™ is a programming language that is supported by all current browsers, the present invention unexpectedly provide viewing and editing of one or more of 2D, 3D and/or 4D medical image data including 2D, 3D, and or 4D display on any browser or web browser control (e.g. WebView) without needing to send the medical image data first to a cloud server, a PACS system or an archiving system and without needing to install special software or browser plugins.

Once the 2D/3D/4D medical images are uploaded to a server environment, they can optionally be further viewed/edited/processed/shared by different parties using the browser. The server-side software could can optionally and/or additionally exchange data with the native software libraries providing or comprising medical image data files, the generated script library, or both in order to decode the 2D/3D/4D formats correctly and consistently.

The cloud, internet, and/or browser, application, or server based medical image sharing and 3D/4D rendering method according to the embodiment of the present invention can be implemented in the form of program instructions that are executable by various types of computer means, and can be recorded in a computer-readable storage medium. The computer-readable storage medium can include program instructions, data files, and data structures either independently or in combination.

The program instructions stored in the medium can be designed and configured especially for the present invention or can be known to and usable by those skilled in the art of computer software. Examples of the computer-readable storage medium can include a magnetic medium, such as a hard disk, a floppy disk, or magnetic tape, an optical medium, such as CD-ROM or a DVD, a magneto-optical medium, such as a floptical disk, and a hardware apparatus, such as ROM, RAM, or flash memory which is especially configured to store and execute the program instructions. Examples of the program instructions include not only such machine language code that is created by a compiler, but also such high-level language code that is executable by a computer using an interpreter or the like. The hardware apparatus can be configured to function as one or more software modules so as to perform the operation of the present invention, and vice versa.

The remote collaborative diagnosis method and system using a cloud, internet, and/or browser, application, or server based medical image sharing and 3D/4D rendering scheme according to the present invention have the advantages of sharing medical images between the users using information about links to the medical images via the browser, application, or server for providing medical images, facilitating remote collaborative diagnoses through the sharing of the medical images, and sharing medical images through the transmission and reception of information about links corresponding to the medical images via the messengers, thereby reducing data traffic between users and improving the security of medical images.

More specifically, the remote collaborative diagnosis method and system using a cloud, internet, and/or browser, application, or server based medical image sharing and 3D/4D rendering scheme according to the present invention have the advantages of transmitting only information about a link to a medical image to be shared to the users of users who make a collaborative diagnosis via messengers, and receiving the sharing-target medical image corresponding to the information about a link from the medical image sharing and 3D/4D rendering browser, application, or server for providing medical images, thereby reducing traffic between users, and improving the security of medical images and protecting private information.

Furthermore, the present invention has the advantages of constructing an interface for sharing medical images in the messenger and enabling users with whom medical images will be shared to be easily selected via the interface, thereby facilitating the sharing of medical images and the making of remote collaborative diagnoses.

Moreover, the present invention has the advantage of enabling a plurality of users participating in a collaborative diagnosis in a remote environment to conveniently share the operation, such as expansion, reduction and the changing of direction, of a medical image displayed to the users in common, annotation, the selection of a medical image of interest from a set of various medical images, switching between a plurality of medical images displayed at the same time, 3D rendering, the results of additional processing, such as a computer aided diagnosis (CAD), and/or the like.

Examples about how the System is Set Up, Transported, and Used for PCI in a Remote Setting The present embodiments of the invention comprise of cloud servers that reside inside data centers operated by commercial cloud hosting providers. One such an example of cloud hosting providers is Amazon, who offers Elastic Compute Cloud (Amazon EC2), which delivers scalable, pay-as-you-go compute capability in the cloud. Using web services and administration tools offered by the cloud computing platform (e.g. Amazon Web Services, or AWS), software modules, such as Anatomy Reconstruction Cloud Service, Procedure Simulation Cloud Service and Patient Record Cloud Service, can be configured and deployed onto "virtual machines". Those services can be configured to allow for best performance for certain geographical locations.

In order to consume the aforementioned cloud services, hospitals should preferably be equipped with high-speed internet to ensure fast access between the hospital and the cloud data center. At least one dedicated workstation is required for each hospital who subscribes to the cloud services. The workstation will have at least one image display device, preferably a 3D projector. According to one embodiment of the present invention, the workstation is also connected to a picture archiving communication system (PACS) in the hospital. The workstation will be configured as a DICOM node inside the local area network, allowing imaging devices (e.g. X-ray machines) to transmit raw patient images to the workstation.

The workstation is preferably connected to a haptics device, which allows users to rehearse a medical procedure using real medical equipment. For hospitals who lack the resources to purchase high-fidelity simulators, the physicians can still use alternative input devices like mouse or keyboard to simulate insertion of catheters/balloons/stents.

In one embodiment, a physician takes X-ray images from three standard projection angles, and the images are submitted to the cloud center for the purpose of seeking decision support in regards of medical device selection, best viewing angle and procedure rehearsal. Preferably, the physician or his/her designee would also upload additional data fields: symptom status, presence or absence of acute coronary syndrome, history of bypass surgery, extent of ischemia on noninvasive imaging, CAD burden from angiography, and degree of anti-anginal medical therapy.

Upon receiving the raw patient data, the Anatomy Reconstruction Cloud Service will launch a series of algorithms, including projection algorithm, composition algorithm and extraction algorithm (FIG. 10) to build volumetric & polygonal mesh representation of the patient 3D model. The mesh-based 3D model is then sent back to the user for real-time display.

If a physician has requested procedure rehearsal service for the incoming patient, the Procedure Simulation Cloud Service will also be launched to compute interactions between input devices and the 3D/4D patient model.

The outputs from the cloud services will be transmitted back to the workstation in the hospital. The physician will receive specific suggestions about the device choices and severity of the case. The physician can choose to perform a simulation based on those suggestions, and also try out different devices on the virtual patient to investigate best treatment strategies for the patient.

Once the real medical intervention has been started, physicians might consider submitting more X-ray images to the cloud center for more decision supports in the middle of the procedure. One such an example is Chronic Total Occlusion (CTO) intervention, a commonly encountered complex lesions identified in 15% of all patients referred for coronary angiography. As the intervention progresses further, additional blood vessels are illuminated through contrast injection, thus it could be beneficial to evaluate blood vessel's 3D characteristics with the updated X-ray images. Preferably, physicians should consider submitting X-ray images at the end of each intervention too so that the patient's post procedure images can be recorded for future references.

The reconstructed patient 3D/4D models will be archived through the Patient Record Cloud Service, providing training and credentialing opportunities for medical school students and physicians at different geographic locations who have access to the simulation network.

Quantitative information incorporated into three-dimensional volumetric images in various configurations of aspects of the invention adds significant diagnostic value to a reconstructed volumetric image while also providing collateral constraints to aid in management of reconstruction artifacts. Furthermore, in some medical applications, a reconstructed three-dimensional volumetric image of an imaged part of anatomy relevant for treatment and/or surgery and/or other structure can be expressed in terms of its constituent material classes and/or tissue types. As a result, reconstructed volumetric images are completely independent of a technique used to acquire a corresponding 2D image dataset. X-ray technique-independent volumetric images can be used for making comparisons between volumetric images reconstructed from datasets acquired on different dates, for example.

The present invention is not limited to configurations involving part of anatomy relevant for treatment and/or surgery image reconstruction and/or even to medical applications, but rather can be used for quantitative reconstruction of an image of any object that is hypothesized to have a limited number of constituent compositions.

While an invention has been described in terms of various specific embodiments, those skilled in an art will recognize that an invention can be practiced with modification within a spirit and/or scope of a claims.

What is claimed is:

1. A computer and internet browser based 2D image sharing and 3D or 4D rendering and display method, comprising:
   (a) electronically transferring, on a computer data network browser, application, or server and through a peer to peer (PTP) or public cloud network or transfer protocol or file attachment, at least one first 2D medical image computer data file to at least one data storage device provided as part of at least one first mobile device or personal computer of at least one first user;
   (b) electronically accessing by the at least one first user the at least one first 2D image computer data file in a browser on the first mobile device or personal computer; and
   (c) electronically rendering on at least one first visual display connected to or included in the at least one first mobile device or personal computer, as controlled in real time by the first user accessing through the browser, at least one real time and manipulatable 3D or 4D image generated from the at least one first 2D image, which at least 3D or 4D image can be stored as a 3D or 4D medical image computer data file and shared and viewed on at least one second visual display via at least one second browser by at least one second user accessing the 2D, 3D, or 4D image on the second browser displayed on at least one second users of at least one second mobile device or personal computer;
   wherein the at least one first 2D medical image computer data file is stored and rendered on said 3D or 4D real time and manipulatable image display using the first or second browser without further processing by additional software or browser plugin on the first or second users' first or second mobile device or personal computer;
   wherein the at least one first 2D medical image computer data file is decoded from, or is generated from, a DICOM-format medical image file;
   wherein the decoded DICOM-format medical image file format does not preserve the original resolution of the DICOM data and includes partial DICOM data or annotation data and wherein the decoded DICOM-format medical image file is less than 50, 40, 30, 20, 10, or 5% of the file size of the original undecoded DICOM-format medical image file;
   wherein the DICOM-format medical image file is preprocessed in a JavaScript™-based library as locally-opened DICOM data prior to said transferring step,
   wherein protected or private patient information is removed from the DICOM-format medical image file; and
   wherein the transferring of the at least one 2D medical image computer data file further includes searching for a plurality of second users with whom the 2D, 3D, or 4D medical image will be shared, based on user information data previously stored via the first browser by the first user.

2. A method of claim 1, wherein the protected or private patient information is PHI BEFORE data in the DICOM-format medical image file, to protect confidential or private patient information, and wherein the patient information removal is completed without any extra private data removal processing software.

3. A method of claim 1, wherein the 2D medical image computer data file are 2D x-ray image files and said rendering generates 3D and 4D x-ray images that are rotatable on said at least one first or second visual displays.

4. A method of claim 1, wherein said at least one first or second visual display further displays at least one of the at least one first or second mobile device or personal computer's device: entry point, entry direction, type, 3D mesh, image anatomy 3D mesh, physics attributes, rendered image analytic data, or rendering related data.

5. A method of claim 1, wherein the rendered 3D or 4D image data file formats include at least one selected from OBJ formats, 3D printer formats, CAD software file formats.

6. A method of claim 1, wherein the 3D or 4D image displays of the at least one first and second users are synchronized.

7. A method of claim 1, further comprising providing at least one of an annotation, text, and voice information between the first and second users that is transmitted to the other user's visual display in real time as inputted by the first or second user via the first or second browser.

8. A method of claim 1, wherein said at least one first 2D medical image computer data file, and/or said 3D or 4D medical image computer data file, is decoded by a medical image library including native programming language coding with source-to-source compiled, transcomiled, or transpiled, script language, such that the rendering step (c) further comprises decoding and/or editing said 2D and 3D or 4D medical images directly inside the first or second browser's control environment without additional plugins or software and without prior uploading of the 2D and the 3D or 4D medical images to a server other than a server used to transfer the first 2D medical image file, or the shared 3D or 4D image, to or from the first or second browser.

9. A method of claim 8, wherein one or more of:
(i) the source to source compiled script language is selected from Low Level Virtual Machine (LLVM), Emscripten, PACL, NACL, the ROSE compiler framework, DMS Software Reengineering Toolkit™, and Haxe;
(ii) the native programming language is selected from C, Fortran, Ada, D, Go™, Tust™; PL/360, Algol, or C++;
(iii) the script language is selected from one or more ECMA Script engines selected from JavaScript™, TypeScript™, CoffeeScript™, Carakan™ SpiderMonkey™, Tamarin™, V8™, Nashorn™, Futhark™, JScript™, Linear B™, QtScript™, QObject™, Rhino™, and YAJ™;
(iv) said medical image library is selected from GDCM, DCMTK, imebra DICOM, USDMC toolkit, and LEADTOOLS medical imaging SDK; and
(v) said 2D, 3D or 4D image or computer data file encoding said image is selected from an x-ray image, a CT image, an MIll image, an ultrasound image, and a PET scan image.

* * * * *